(12) United States Patent
Hazan et al.

(10) Patent No.: US 11,207,333 B2
(45) Date of Patent: *Dec. 28, 2021

(54) COMPOSITIONS COMPRISING TRITERPENOIDS AND USES THEREOF FOR TREATING OPTIC NEUROPATHY

(71) Applicant: REGENERA PHARMA LTD., Ness Ziona (IL)

(72) Inventors: Zadik Hazan, Zichron Yaakov (IL); Andre C. B. Lucassen, Rehovot (IL); Konstantin Adamsky, Gedera (IL)

(73) Assignee: REGENERA PHARMA LTD., Ness Ziona (IL)

( * ) Notice: Subject to any disclaimer, the term of this patent is extended or adjusted under 35 U.S.C. 154(b) by 264 days.

This patent is subject to a terminal disclaimer.

(21) Appl. No.: 16/330,486

(22) PCT Filed: Sep. 7, 2017

(86) PCT No.: PCT/IL2017/051007
§ 371 (c)(1),
(2) Date: Mar. 5, 2019

(87) PCT Pub. No.: WO2018/047175
PCT Pub. Date: Mar. 15, 2018

(65) Prior Publication Data
US 2019/0224217 A1    Jul. 25, 2019

Related U.S. Application Data

(60) Provisional application No. 62/384,717, filed on Sep. 8, 2016.

(51) Int. Cl.
*A61K 31/575* (2006.01)
*A61K 31/047* (2006.01)
*A61K 31/19* (2006.01)
*A61K 36/22* (2006.01)
*A61K 31/56* (2006.01)
*A61P 25/00* (2006.01)
*A61K 31/045* (2006.01)
*A61P 27/06* (2006.01)
*A61K 47/44* (2017.01)
*A61K 9/00* (2006.01)

(52) U.S. Cl.
CPC .......... *A61K 31/575* (2013.01); *A61K 31/045* (2013.01); *A61K 31/047* (2013.01); *A61K 31/19* (2013.01); *A61K 31/56* (2013.01); *A61K 36/22* (2013.01); *A61K 47/44* (2013.01); *A61P 25/00* (2018.01); *A61P 27/06* (2018.01); *A61K 9/0019* (2013.01)

(58) Field of Classification Search
CPC .... A61K 31/575; A61K 31/047; A61K 31/19; A61K 36/22; A61K 31/56; A61K 31/045; A61K 47/44; A61K 9/0019; A61P 25/00; A61P 27/06
See application file for complete search history.

(56) References Cited

U.S. PATENT DOCUMENTS

| 7,048,943 B2 | 5/2006 | Barenholz et al. |
| 9,770,456 B2 | 9/2017 | Hazan et al. |
| 2005/0238740 A1 | 10/2005 | Fotinos et al. |
| 2011/0281955 A1 | 11/2011 | Meyer et al. |
| 2012/0003175 A1 | 1/2012 | Hazan |
| 2018/0071351 A1 | 3/2018 | Hazan et al. |
| 2019/0192594 A1 | 6/2019 | Hazan |

FOREIGN PATENT DOCUMENTS

| CN | 103656290 A | 3/2014 |
| EP | 1520585 A1 | 4/2005 |
| WO | 03092712 A1 | 11/2003 |
| WO | 2005094837 A1 | 10/2005 |
| WO | 2005112967 A2 | 12/2005 |
| WO | 2010100650 A2 | 9/2010 |
| WO | 2010100651 A2 | 9/2010 |
| WO | 2012032523 A2 | 3/2012 |
| WO | 2013186766 A1 | 12/2013 |
| WO | 2015121441 A1 | 8/2015 |
| WO | 2015138773 A2 | 9/2015 |

OTHER PUBLICATIONS

Aalami-Harandi et al., (2008) Efficacy of Memantine in Acute Non-Arteritic Ischemic Optic Neuropathy. Iranian Journal of Ophthalmology 20(3): 39-44.
Al-Habbal et al., (1984) A Double-Blind Controlled Clinical Trial of Mastic and Placebo in the Treatment of Duodenal Ulcer. Clinical and Experimental Pharmacology and Physiology 11(5): 541-544.
Allcutt et al., (1984) A qualitative comparison of the reactions of retinal ganglion cell axons to optic nerve crush in neonatal and adult mice. Developmental Brain Research 16(2): 231-240.
Allcutt et al., (1984) A quantitative comparison of the reactions of retinal ganglion cells to optic nerve crush in neonatal and adult mice. Developmental Brain Research 16(2): 219-230.
Al-Said et al., (1986) Evaluation of mastic, a crude drug obtained from Pistacia lentiscus for gastric and duodenal anti-ulcer activity. Journal of Ethnopharmacology 15(3): 271-278.
Barton and Seoane (1956) 801. Triterpenoids Part XXII. The constitution and stereochemistry of masticadienonic acid. J Chem Soc 0: 4150-4157.
Cioffi et al., (1995) An in vivo model of chronic optic nerve ischemia: The dose-dependent effects of endothelin-I on the optic nerve microvasculature. Current Eye Research 14(12): 1147-1153.
Cone et al., (2012) The effects of anesthesia, mouse strain and age on intraocular pressure and an improved murine model of experimental glaucoma. Exp Eye Res 99: 27-35.
Domingo et al., (2009) Enantioselective total synthesis of the potent anti-inflammatory (+)-myrrhanol A. J Org Chem 74(16): 6151-6156.

(Continued)

*Primary Examiner* — Shirley V Gembeh

(74) *Attorney, Agent, or Firm* — Rothwell, Figg, Ernst & Manbeck, P.C.

(57) ABSTRACT

The invention relates to compositions and formulations comprising at least one triterpenoic acid and at least one neutral triterpenoid and uses thereof for treating optic neuropathy conditions.

20 Claims, 2 Drawing Sheets

(56) References Cited

OTHER PUBLICATIONS

Domingo et al., (2013) First synthesis of (+)-myrrhanol C, an anti-prostate cancer lead. Org Biomol Chem 11(4): 559-562.

Giner-Larza et al., (2002) Anti-inflammatory triterpenes from Pistacia terebinthus galls. Planta Med 68(4): 311-315.

Justicia et al., (2004) Titanocene-catalyzed cascade cyclization of epoxypolyprenes: straightforward synthesis of terpenoids by free-radical chemistry. Chem. Eur. J. 10(7): 1778-1788.

Kalesnykas et al., (2007) The expression of heat shock protein 27 in retinal ganglion and glial cells in a rat glaucoma model. Neuroscience 150(3): 692-704.

Kawasaki et al., (2002) Protective effect of arachidonic acid on glutamate neurotoxicity in rat retinal ganglion cells. Investigative Ophthalmology & Visual Science 43(6): 1835-1842.

Orgül et al., (1996) An endothelin-1-induced model of chronic optic nerve ischemia in rhesus monkeys. Journal of Glaucoma 5(2): 135-138.

Marner et al., (1991) Triterpenoids from gum mastic, the resin of Pistacia lentiscus. Phytochemistry 30(11): 3709-3712.

Otori (2008) Use of purified retinal ganglion cells for an in vitro model to study glaucoma. Mechanisms of the Glaucomas: 601-607.

Paraschos et al., (2007) In vitro and in vivo activities of Chios mastic gum extracts and constituents against Helicobacter pylori. Antimicrob Agents Chemother 51(2): 551-559.

Ragauskas et al., (2014) Early retinal function deficit without prominent morphological changes in the R6/2 mouse model of Huntington's disease. PLoS One 9(12): e113317; 24 pages.

Sappington et al., (2010) The microbead occlusion model: a paradigm for induced ocular hypertension in rats and mice. Investigative Ophthalmology & Visual science 51(1): 207-216.

Seoane (1956) 802. Further crystalline constituents of gum mastic. J Chem Soc 0: 4158-4160.

Matsuda et al., (1999) Antidiabetic principles of natural medicines. IV. Aldose reductase and qlpha-glucosidase inhibitors from the roots of Salacia oblonga Wall. (*Celastraceae*): structure of a new friedelane-type triterpene, kotalagenin 16-acetate. Chem Pharm Bull (Tokyo) 47(12): 1725-1729.

Morimoto (2013) A new strategy for the treatment of various intractable optic nerve diseases. Neuro-Ophthalmology Japan. 30(1): 43-52. Abstract.

Shimazawa (2014) Pathophysiology of glaucoma, drug treatment and future prospects. Pharmacia 50(3): 207-211. With machine translation.

COMPOSITIONS COMPRISING TRITERPENOIDS AND USES THEREOF FOR TREATING OPTIC NEUROPATHY

CROSS REFERENCE TO RELATED APPLICATION

This application is a 35 U.S.C. 371 National Phase Entry Application from PCT/IL2017/051007, filed Sep. 7, 2017, which claims the benefit of U.S. Provisional Patent Application No. 62/384,717 filed on Sep. 8, 2016, the disclosures of which are incorporated herein in their entirety by reference.

FIELD OF THE INVENTION

The invention relates to compositions comprising triterpenoids, and uses thereof, in particular for treating optic neuropathy related conditions.

BACKGROUND OF THE INVENTION

The optic nerve contains axons of nerve cells that emerge from the retina, leave the eye at the optic disc, and go to the visual cortex where input from the eye is processed into vision. Optic neuropathy refers to damage to the optic nerve due to any cause. Damage and death of these nerve cells, leads to characteristic features of optic neuropathy. The main symptom is loss of vision, with colors appearing subtly washed out in the affected eye. On medical examination, the optic nerve head can be visualized by an ophthalmoscope. A pale disc is characteristic of long-standing optic neuropathy. In many cases, only one eye is affected and patients may not be aware of the loss of color vision until the doctor asks them to cover the healthy eye.

Optic neuropathy can result from various reasons, such as, Ischemic optic neuropathy, Optic neuritis, Compressive optic neuropathy, Infiltrative optic neuropathy, Traumatic optic neuropathy, mitochondrial optic neuropathy, Nutritional optic neuropathies, toxic optic neuropathies, hereditary optic neuropathies, and the like. Very few treatments of optical neuropathy are currently used, and most have a limited effect on specific type of optic neuropathy.

Glaucoma is one of the leading cause of blindness in the world. There are a variety of different types of glaucoma, all sharing the same pathophysiology of retinal ganglion cells (RGCs) loss. The most common forms of glaucoma are primary open angle glaucoma (POAG), Primary close angle glaucoma (PCAG), primary congenital glaucoma (PCG). Glaucoma can also arise as a secondary complication of other pathophysiological conditions. Examples for secondary glaucomas are pigmentary, steroid-induced, exfoliation, angle recession, phacolytic and vascular glaucoma. The common mechanism of the disease is the elevated intraocular pressure (IOP) that induces stress on the RGCs and consequentially leads to their gradual loss. Therapeutic approaches that delay or halt RGCs loss have been recognized to be potentially beneficial to preserve vision in glaucoma. Currently available treatments focus on intraocular pressure (IOP) reduction, either by drugs or surgical intervention. Additionally, neuroregenerative therapies may have the potential to halt RGC loss through cell survival mechanisms. However, such interventions do not always halt progression of the glaucoma and loss of vision in patients.

Various drug entities derived from plants and plant products have been disclosed over the years, for various therapeutic applications.

For example, Paraschos et al disclose preparation of a total mastic extract without polymer (TMEWP) by polar solvent extraction of crude mastic, removal of the insoluble polymer poly-β-myrcene therefrom, and separation of acidic and neutral fractions from TMEWP (Paraschos et al (2007) Antimicrob. Agents Chemother. 51(2):551-559).

International Patent Application Publication No. WO 2005/112967 is directed to the anticancer activity of mastic gum.

International Patent Application Publication No. WO 2010/100650 of some of the inventors of the present invention, is directed to therapeutic uses of mastic gum fractions.

International Patent Application Publication No. WO 2010/100651 of some of the inventors of the present invention, is directed to compositions of polymeric myrcene.

International Patent application Publication NO. WO 2012/032523 of some of the inventors of the present invention, is directed to acidic compositions of mastic gum.

International Patent Application Publication No. WO 2005/094837 is directed to Use of masticadienonic acid as inhibitor of DNA polymerase-beta, used for treating cancers, tumors and neurodegenerative diseases.

Marner et al (1991) disclose identification of various triterpenoids from gum mastic of *P. lentiscus* (Marner et al (1991) Phytochemistry, 30, 3709-3712).

Giner-Larza et al (2002) disclose anti-inflammatory triterpenes from *pistacia terebinthus* galls (Planta Med (2002), 68, 311-315).

There is a need in the art for compositions that are useful and effective in treating conditions of optical neuropathy, resulting from various reasons. The art does not provide any teaching that isolated acidic fractions of mastic gum can be used for treating optical neuropathy conditions.

SUMMARY OF THE INVENTION

The following embodiments and aspects thereof are described and illustrated in conjunction with systems, tools and methods, which are meant to be exemplary and illustrative, not limiting in scope.

In some embodiments, there are provided combinations of triterpenoid compounds, compositions comprising the same and uses thereof for the treatment of optical neuropathy conditions.

In some embodiments, there is provided a composition comprising a combination of at least one triterpenoic acid and at least one neutral triterpenoid; and a pharmaceutically acceptable carrier for use in treating an optic neuropathy condition.

In some embodiments, there is provided a composition comprising a combination of a triterpenoic acid and a neutral triterpenoid; and a pharmaceutically acceptable carrier, for use in treating an optic neuropathy condition.

In some embodiments, the compositions and/or combinations of compounds, as disclosed herein, unexpectedly exhibit a variety of beneficial biological activities, which are exploited for treating optic neuropathy in a surprisingly efficient manner. More specifically, the compositions and combinations disclosed herein are shown to be active and useful in treating optic neuropathy conditions, which may include any condition in which the optic nerve is damaged. In some embodiments, the optic neuropathy condition may be selected from such conditions as, but not limited to: traumatic neuropathy (that may result from any type of trauma to the optic nerve); ischemic neuropathy (such as, for example, Nonarteritic Anterior Ischemic Optic neuropathy (NAION)), Anterior ischemic optic neuropathy (AION), Posterior ischemic optic neuropathy); Radiation optic neuropathy (RON)), Glaucoma, Optic neuritis, Compressive optic neuropathy, Infiltrative optic neuropathy, Mitochondrial optic neuropathy, Nutritional optic neuropathies, toxic optic neuropathies, Hereditary optic neuropathy and the like; or combinations thereof. Each possibility is a separate embodiment.

In some embodiments, the optic neuropathy condition is resulting from or associated with damage to the optical nerve as a result of deposition of lipoproteinaceous substances in the optic nerve.

In some embodiments, the optic neuropathy condition is resulting from or associated with damage to the optical nerve as a result of deposition of lipoproteinaceous substances in the optic nerve, wherein the deposition of lipoproteinaceous substances is the result of a storage disease.

In some embodiments, the optic neuropathy condition is resulting from or associated with damage to the optical nerve as a result of deposition of lipoproteinaceous substances in the optic nerve, wherein the deposition of lipoproteinaceous substances is the result of a storage disease, and wherein the lipoproteinaceous substance is lipofuscin.

According to some embodiments, there is provided use of a composition comprising a combination of at least one triterpenoic acid and at least one neutral triterpenoid and a pharmaceutically acceptable carrier; for treating an optic neuropathy condition.

According to some embodiments, there is provided a method of treating an optic neuropathy condition in a subject in need thereof, the method comprising administering a composition comprising a combination of at least one triterpenoic acid and at least one neutral triterpenoid and a pharmaceutically acceptable carrier.

In some embodiments, the triterpenoic acid is selected from masticadienonic acid (MDA), isomasticadienonic acid (IMDA), masticadienolic acid (MLA), isomasticadienolic acid (IMLA), 3-O-acetyl-masticadienolic acid, 3-O-acetyl-epimasticadienolic acid, 3-O-acetyl-isomasticadienolic acid, 3-O-acetyl-epi-isomasticadienolic acid, oleanonic acid (OA) and moronic acid (MA).

In some embodiments, at least one of said triterpenoic acids is selected from MDA, IMDA, MLA and IMLA. In some embodiments, at least one of said triterpenoic acids is selected from MDA, IMDA, 3-O-acetyl-MLA and 3-O-acetyl-IMLA.

In some embodiments, the neutral triterpenoid is selected from (8R)-3-beta, 8-dihydroxypolypoda-13E,17E,21-triene (NF-1), (8R)-3-Oxo-8-hydroxypolypoda-13E,17E,21-triene (NF-2), Oleanonic aldehyde (NF-3), Tirucallol (NF-4), 28-hydroxylup-20(29)-en-3-one (NF-A), 28-hydroxy-beta-amyrone (NF-B), and 20-hydroxydammar-24-en-3-one (NF-P).

In some embodiments, at least one of said neutral triterpenoids is selected from NF-1, NF-2, NF-3 and NF-4.

In some embodiments, the composition comprises at least two triterpenoic acids

In some embodiments, the composition comprises at least four neutral triterpenoids.

In some embodiments, the neutral triterpenoid comprises at least (8R)-3-beta, 8-dihydroxypolypoda-13E,17E,21-triene (NF-1).

In some embodiments, the neutral triterpenoid comprises at least (8R)-3-Oxo-8-hydroxypolypoda-13E,17E,21-triene (NF-2).

In some embodiments, the triterpenoid comprises at least (8R)-3-beta, 8-dihydroxypolypoda-13E,17E,21-triene (NF-1) and (8R)-3-Oxo-8-hydroxypolypoda-13E,17E,21-triene (NF-2).

In some embodiments, the neutral triterpenoid comprises at least Tirucallol (NF-4).

In some embodiments, the neutral triterpenoid comprises at least Oleanonic aldehyde (NF-3).

In some embodiments, the composition is substantially devoid of essential oils.

In some embodiments, at least one triterpenoic acid is obtained from a plant source. In some embodiments, at least one neutral triterpenoid is obtained from a plant source. In some embodiments, at least one neutral triterpenoid is isolated.

In some embodiments, pharmaceutically acceptable carrier comprises a hydrophobic carrier. In some embodiments, the hydrophobic carrier comprises at least one oil.

In some embodiments, the optic neuropathy condition is selected from traumatic neuropathy, ischemic neuropathy; Radiation optic neuropathy (RON), Glaucoma, Optic neuritis, Compressive optic neuropathy, Infiltrative optic neuropathy, Mitochondrial optic neuropathy, Nutritional optic neuropathies, toxic optic neuropathies, Hereditary optic neuropathy and combinations thereof.

In some embodiments, the ischemic optic neuropathy is selected from: Nonarteritic Ischemic Optic neuropathy (NAION), Anterior ischemic optic neuropathy (AION) and Posterior ischemic optic neuropathy.

In some embodiments, the optic neuropathy condition resulted from a storage disease. In some embodiments, the storage disease caused the deposition of lipoprotenaceous substances in the optical nerve.

In some embodiments, the composition may be administered by parenteral route. In some embodiments, the parenteral route may be selected from the group consisting of intravenous, intramuscular, subcutaneous, intradermal, intraperitoneal, intraarterial, intrauterine, intraurethral, intracardial, intracerebral, intracerebroventricular, intrarenal, intrahepatic, intratendon, intraosseous, intraocular and intrathecal.

According to some embodiments, there is provided a pharmaceutical composition comprising pharmaceutically active ingredients consisting essentially of MA, OA, MDA, IMDA, 3-O-acetyl-masticadienolic acid, 3-O-acetyl-isomasticadienolic acid, MLA, IMLA, NF-1, NF-2, NF-3 and NF-4; and a pharmaceutically acceptable carrier, for use in treating an optic neuropathy condition.

According to some embodiments, there is provided a pharmaceutical composition comprising pharmaceutically active ingredients consisting essentially of MDA, IMDA, MLA, IMLA, NF-1, NF-2, NF-3, NF-4, NF-P, NF-A and NF-B; and a pharmaceutically acceptable carrier, for use in treating an optic neuropathy condition.

According to some embodiments, there is provided a pharmaceutical composition comprising pharmaceutically active ingredients consisting essentially of MDA, IMDA, NF-1, NF-2, NF-3 and NF-4; and a pharmaceutically acceptable carrier, for use in treating an optic neuropathy condition.

According to some embodiments, there is provided a pharmaceutical composition comprising pharmaceutically active ingredients consisting essentially of MDA, IMDA, NF-1, NF-2; and a pharmaceutically acceptable carrier, for use in treating an optic neuropathy condition.

According to some embodiments, there is provided a pharmaceutical composition comprising pharmaceutically active ingredients consisting essentially of MDA, IMDA, NF-3, NF-4; and a pharmaceutically acceptable carrier, for use in treating an optic neuropathy condition.

According to some embodiments, there is provided a pharmaceutical composition comprising pharmaceutically active ingredients consisting essentially of MDA, IMDA and NF-4; and a pharmaceutically acceptable carrier, for use in treating an optic neuropathy condition.

According to some embodiments, there is provided a pharmaceutical composition comprising pharmaceutically active ingredients consisting essentially of MA, OA, MDA, IMDA, 3-O-acetyl masticadienolic acid, 3-O-acetyl isomasticadienolic acid, MLA, IMLA, NF-1, NF-2, NF-3, NF-4, NF-P, NF-A and NF-B as the sole pharmaceutically active ingredients; and a pharmaceutically acceptable carrier, for use in treating an optic neuropathy condition.

According to some embodiments, there is provided a pharmaceutical composition comprising pharmaceutically active ingredients consisting essentially of MDA, IMDA, NF-1, NF-2, NF-3, NF-4, NF-P, NF-A and NF-B as the sole pharmaceutically active ingredients; and a pharmaceutically acceptable carrier, for use in treating an optic neuropathy condition.

According to some embodiments, there is provided a pharmaceutical composition comprising pharmaceutically active ingredients consisting essentially of MDA, IMDA, NF-1, NF-2, NF-3, NF-4, NF-A and NF-B as the sole pharmaceutically active ingredients; and a pharmaceutically acceptable carrier, for use in treating an optic neuropathy condition.

According to some embodiments, there is provided a pharmaceutical composition comprising pharmaceutically active ingredients consisting essentially of MDA, IMDA, NF-3 and NF-4 as the sole pharmaceutically active ingredients; and a pharmaceutically acceptable carrier, for use in treating an optic neuropathy condition.

According to some embodiments, there is provided a pharmaceutical composition comprising pharmaceutically active ingredients consisting essentially of MDA, IMDA, NF-1, and NF-2 as the sole pharmaceutically active ingredients; and a pharmaceutically acceptable carrier, for use in treating an optic neuropathy condition.

According to some embodiments, there is provided a pharmaceutical composition comprising pharmaceutically active ingredients consisting essentially of MDA, IMDA and NF-4 as the sole pharmaceutically active ingredients; and a pharmaceutically acceptable carrier, for use in treating an optic neuropathy condition.

According to some embodiments, there is provided a pharmaceutical composition comprising pharmaceutically active ingredients consisting essentially of MDA, IMDA and NF-3 as the sole pharmaceutically active ingredients; and a pharmaceutically acceptable carrier, for use in treating an optic neuropathy condition.

According to some embodiments, there is provided a method of treating an optic neuropathy condition, comprising administering to a subject a composition as disclosed herein.

According to some embodiments, there is provided a method of treating an optic neuropathy condition in a subject in need thereof, the method comprising administering to a subject a therapeutically effective amount of a composition as disclosed herein.

According to some embodiments, there is provided a method of treating an optic neuropathy condition in a subject in need thereof, the method comprising administering a pharmaceutical composition comprising pharmaceutically active ingredients consisting essentially of MA, OA, MDA, IMDA, 3-O-acetyl-masticadienolic acid, 3-O-acetyl-isomasticadienolic acid, MLA, IMLA, NF-1, NF-2, NF-3 and NF-4.

According to some embodiments, there is provided a method of treating an optic neuropathy condition in a subject in need thereof, the method comprising administering a pharmaceutical composition comprising pharmaceutically active ingredients consisting essentially of MDA, IMDA, MLA, IMLA, NF-1, NF-2, NF-3, NF-4, NF-P, NF-A and NF-B; and a pharmaceutically acceptable carrier.

According to some embodiments, there is provided a method of treating an optic neuropathy condition in a subject in need thereof, the method comprising administering a pharmaceutical composition comprising pharmaceutically active ingredients consisting essentially of MDA, IMDA, NF-1, NF-2, NF-3 and NF-4; and a pharmaceutically acceptable carrier.

According to some embodiments, there is provided a method of treating an optic neuropathy condition in a subject in need thereof, the method comprising administering a pharmaceutical composition comprising pharmaceutically active ingredients consisting essentially of MDA, IMDA, NF-1, NF-2; and a pharmaceutically acceptable carrier.

According to some embodiments, there is provided a method of treating an optic neuropathy condition in a subject in need thereof, the method comprising administering a pharmaceutical composition comprising pharmaceutically active ingredients consisting essentially of MDA, IMDA, NF-3, NF-4; and a pharmaceutically acceptable carrier.

According to some embodiments, there is provided a method of treating an optic neuropathy condition in a subject in need thereof, the method comprising administering a pharmaceutical composition comprising pharmaceutically active ingredients consisting essentially of MDA, IMDA and NF-4; and a pharmaceutically acceptable carrier.

According to some embodiments, there is provided a method of treating an optic neuropathy condition in a subject in need thereof, the method comprising administering a pharmaceutical composition comprising pharmaceutically active ingredients consisting essentially of MA, OA, MDA, IMDA, 3-O-acetyl-masticadienolic acid, 3-O-acetyl-isomasticadienolic acid, MLA, IMLA, NF-1, NF-2, NF-3, NF-4, NF-P, NF-A and NF-B as the sole pharmaceutically active ingredients.

According to some embodiments, there is provided a method of treating an optic neuropathy condition in a subject in need thereof, the method comprising administering a pharmaceutical composition comprising pharmaceutically active ingredients consisting essentially of MDA, IMDA, NF-1, NF-2, NF-3, NF-4, NF-P, NF-A and NF-B as the sole pharmaceutically active ingredients; and a pharmaceutically acceptable carrier.

According to some embodiments, there is provided a method of treating an optic neuropathy condition in a subject in need thereof, the method comprising administering a pharmaceutical composition comprising pharmaceutically active ingredients consisting essentially of MDA, IMDA, NF-1, NF-2, NF-3, NF-4, NF-A and NF-B as the sole pharmaceutically active ingredients; and a pharmaceutically acceptable carrier.

According to some embodiments, there is provided a method of treating an optic neuropathy condition in a subject in need thereof, the method comprising administering pharmaceutical composition comprising pharmaceutically active ingredients consisting essentially of MDA, IMDA, NF-3 and NF-4 as the sole pharmaceutically active ingredients; and a pharmaceutically acceptable carrier.

According to some embodiments, there is provided a method of treating an optic neuropathy condition in a subject in need thereof, the method comprising administering a pharmaceutical composition comprising pharmaceutically active ingredients consisting essentially of MDA, IMDA, NF-1, and NF-2 as the sole pharmaceutically active ingredients; and a pharmaceutically acceptable carrier.

According to some embodiments, there is provided a method of treating an optic neuropathy condition in a subject in need thereof, the method comprising administering a pharmaceutical composition comprising pharmaceutically active ingredients consisting essentially of MDA, IMDA and NF-4 as the sole pharmaceutically active ingredients; and a pharmaceutically acceptable carrier.

According to some embodiments, there is provided a method of treating an optic neuropathy condition in a subject in need thereof, the method comprising administering a pharmaceutical composition comprising pharmaceutically active ingredients consisting essentially of MDA, IMDA and NF-3 as the sole pharmaceutically active ingredients; and a pharmaceutically acceptable carrier.

According to some embodiments, there is provided a kit comprising a pharmaceutical composition as disclosed herein for treating an optic neuropathy condition in a subject in need thereof.

According to some embodiments, there is provided a kit comprising: (a) a pharmaceutical composition comprising at least one triterpenoic acid and a pharmaceutically acceptable carrier; (b) a pharmaceutical composition comprising at least one neutral triterpenoid and a pharmaceutically acceptable carrier; wherein the kit is for treating an optic neuropathy condition in a subject in need thereof.

In some embodiments, the kit may further include instructions for use of the first and second pharmaceutical compositions together in treating an optic neuropathy condition of a subject in need thereof.

According to some embodiments, there is provided at least one triterpenoic acid and at least one neutral triterpenoid in the preparation of a composition for use in treating an optic neuropathy condition.

In some embodiments, there is provided a kit comprising a pharmaceutical composition as disclosed herein.

In some embodiments, there is provided a kit comprising: (a) a pharmaceutical composition comprising at least one triterpenoic acid and a pharmaceutically acceptable carrier; (b) a pharmaceutical composition comprising at least one neutral triterpenoid and a pharmaceutically acceptable carrier.

In some embodiments, there is provided a use of at least one triterpenoic acid and at least one neutral triterpenoid in the preparation of a composition for treating an optic neuropathy condition.

In some embodiments, combinations of triterpenoic acids and neutral triterpenoids may be substantially devoid of essential oils.

In some embodiments, the composition may be in a form suitable for administration by a route selected from the group consisting of parenteral, transdermal, oral and topical. In various embodiments, the composition may be administered by parenteral route. According to some embodiments, the route of administration may be via parenteral injection. In various embodiments, the step of administering is carried out by a parenteral route selected from the group consisting of intravenous (i.v.), intramuscular, subcutaneous (sc), intradermal, intraperitoneal, intraarterial, intracerebral, intracerebroventricular, intraosseous, intraocular, intravitreal, and intrathecal.

In some embodiments, the subject to be treated with the compositions disclosed herein may be selected from the group of humans, and non-human mammals.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION OF THE INVENTION

Figure 1:
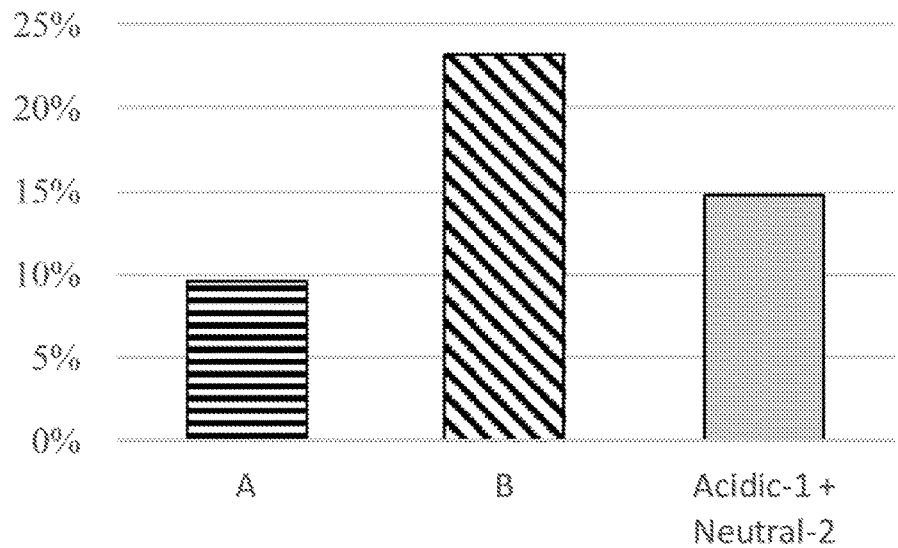
FIG. 1—Bar graphs showing pERG measurements relative change in mean amplitude in treated rats (Eye-laser irradiated) performed at follow-up day 28 as compared to control vehicle-treated group.

As disclosed herein, it has been surprisingly found that combinations of triterpenoic acids and neutral triterpenoid compounds show high activity in treating various optic neuropathy condition, selected from such conditions as, but not limited to: traumatic neuropathy (that may result from any type of trauma to the optic nerve); ischemic neuropathy (such as, for example, Nonarteritic Anterior Ischemic Optic neuropathy (NAION), Anterior ischemic optic neuropathy (AION), Posterior ischemic optic neuropathy); Radiation optic neuropathy (RON)), Glaucoma of various kinds, Optic neuritis, Compressive optic neuropathy, Infiltrative optic neuropathy, Mitochondrial optic neuropathy, Nutritional optic neuropathies, toxic optic neuropathies, Hereditary optic neuropathy and the like; or combinations thereof.

Specific combinations of triterpenoic acids and neutral terpenoid compounds surprisingly show enhanced therapeutic efficacy.

Definitions

As used herein the term "plurality" refers to more than one, preferably more than two. As used herein the term "synergistic" means more than additive.

As used herein, the term "acid-base extraction" refers to a procedure in which an organic solvent solution containing organic acidic (typically, organic carboxylic acids) and organic non-acidic components is treated/extracted with one or more basic aqueous solution(s). As a result of this, the organic acidic components are deprotonated and thus converted into their corresponding deprotonated ionic salt forms (typically, organic anionic carboxylates) and as a result will dissolve in the said basic aqueous solution. The non-acidic organic components will not deprotonate, thus will stay behind in the original organic solution phase. The deprotonated acids may also form an intermediate oily and/or emulsion layer, especially when multigram amounts are being extracted. The basic aqueous solution containing the deprotonated salt forms of the acidic components, together with the oily and/or emulsion layer (if present), is acidified, resulting in the reformation of the protonated acid forms of the organic acidic components. These protonated acid forms (acidic fraction) can be removed from the acidified aqueous solution in several ways depending on the properties of the acidic compounds. One option for removing the acidic fraction from the acidified solution is by reextraction into a suitable organic solvent. Example 1 describe non-limiting example of an acid-base extraction as described above. Depending on the solubility and physical form of the acidic compounds (e.g. if the acidic fraction typically comprises a separated/precipitated solid) in the acidified aqueous solution, the acidic fraction may be isolated via filtration of the acidified aqueous solution.

As stated above, the original organic solution phase remaining after extraction with basic aqueous solution(s) contains the non-acidic organic components. In the case of mastic gum these non-acidic components consist of neutral triterpenoids and the mixture is referred to as a neutral fraction. Example describe particular (but non-limiting) methods for the isolation of a certain acidic and a certain neutral fraction from mastic gum.

From the isolated acidic fraction and neutral fraction, the individual triterpenoic acids and neutral triterpenoids can be isolated using methods known in the art such as column chromatography and HPLC. Several references presented in the introduction of the current application contain examples of separation methods for triterpenoic acids and neutral triterpenoids from mastic gum. It is to be understood, and it is clear to a person skilled in the art, that there are other possible synthesis routes to any of the disclosed compounds as well as other compounds that are part of compositions of this invention.

Instead of using a basic aqueous solution for the acid-base extraction, basic forms of ion-exchange resins can be used as well. In these cases, upon contact with the ion-exchange resin the acidic organic components (acidic fraction—typically, organic carboxylic acids) are captured in their deprotonated anionic form (typically, organic anionic carboxylates) by the resin. The resin is subsequently removed from the initial solution, leaving non-acidic components behind. The acidic components (acidic fraction) are subsequently released from the resin by treatment of the resin with a suitable acidic solution. The use of ion-exchange resins for acid-base extractions is especially suitable for process scale up and can be used for the development of (semi)continuous extraction processes.

Examples of the above acid-base extractions and other variations can be found in many textbooks and other publications, and are considered common knowledge to those skilled in the art. An example of a useful textbook is "Vogel's Textbook of Practical Organic Chemistry", $5^{th}$ Edition, 1989, (p. 162-163).

As used herein, the term "degree of purity" refers to the content of a specified chemical compound in a preparation, expressed as a percentage on a weight per weight basis of the specified chemical compound relative to other chemical compounds in the preparation.

As used herein, "terpene compounds" refers to isoprene-containing hydrocarbons, having isoprene units ($CH_2C(CH_3)CHCH_2$) in a head-to-tail orientation. Terpene hydrocarbons in general, have the molecular formula $(C_5H_8)_n$, and include hemiterpenes, (C5), monoterpenes (C10), sesquiterpenes (C15), diterpenes (C20), triterpenes (C30), and tetraterpenes (C40) which respectively have 1, 2, 3, 4, 6 and 8 isoprene units. Terpenes may be further classified as acyclic or cyclic.

As used herein, "terpenoids" and "terpenoid compounds" interchangeably refer to terpene-related compounds which contain at least one oxygen atom in addition to isoprene units, and thus include alcohols, aldehydes, ketones, ethers, such as but not limited to, carboxylic acids derivatives thereof, such as esters. Terpenoids are subdivided according to the number of carbon atoms in a manner similar to terpene and thus include hemiterpenoids, (C5), monoterpenoids (C10), sesquiterpenoids (C15), diterpenoids (C20), triterpenoids (C30), and tetraterpenoids (C40) which respectively have 1, 2, 3, 4, 6 and 8 isoprene units. The skeleton of terpenoids may differ from strict additivity of isoprene units by the loss or shift of a fragment, commonly a methyl group. Examples of monoterpenoids include camphor, eugenol, menthol and borneol. Examples of diterpenoids include phytol, retinol and taxol. Examples of triterpenoids include betulinic acid and lanosterol. Terpenoids may be acyclic or may contain one or more ring-structures. Triterpenoids may be acyclic or may contain one or more ring-structures. The rings may contain only carbon atoms, or alternatively may contain one or more oxygen atoms besides carbon atoms. Common ring-sizes range from three-membered rings to ten-membered rings. Larger ring sizes of up to at least twenty-membered rings are possible. More than one ring and more than one ring-size maybe present in a single triterpenoid. In case a triterpenoid contains more than one ring, the rings may be present and separated by one or more acyclic bonds; alternatively the rings may be directly connected via connections of the annealed type, the bridged type, the spiro-type or combinations of any of these types. Multiply annealed, fused, bridged, or spiro-type ringsystems are possible. Combinations of singly and multiply annealed, bridged, fused, spiro-type rings are possible. Combinations of isolated rings and connected rings in the same triterpenoid are possible.

As used herein, "terpenoic acids" refer to terpenoid compounds containing at least one carboxylic acid functional group (COOH). The terpenoic acids may additionally contain one or more other oxygen-containing functional groups, for example, but not limited to hydroxyl, keto, aldehyde, ether (cyclic and non-cyclic), ester (cyclic and non-cyclic). They also may contain one or more C=C double bond, each double bond may be of the cis, trans, E-type, Z-type, as well as mono-substituted, di-substituted, tri-substituted or tetra-substituted (meaning no vinylic H-substituent), independently from other C=C bonds. The carboxylic acid group may be present in the protonated form (COOH) or in deprotonated anionic form (COO$^-$).

As used herein, "triterpenoic acids" refer to triterpenoid compounds containing at least one carboxylic acid group. The triterpenoic acids may additionally contain one or more other oxygen-containing functional groups for example, but not limited to, hydroxyl, keto, aldehyde, ether (cyclic and non-cyclic) and ester (cyclic and non-cyclic). They also may contain one or more C=C double bond, each double bond may be of the cis, trans, E- or Z-type, as well as monosubstituted, disubstituted, trisubstituted or tetrasubstituted (meaning no vinylic H-substituent), independently from other C=C bonds. The carboxylic acid group may be present in the protonated form (COOH) or in deprotonated anionic form (COO$^-$).

As used herein, "neutral terpenoids" refer to terpenoid compounds lacking a carboxylic acid group. The neutral triterpenoids may contain one or more other oxygen-containing functional groups for example, but not limited to, hydroxyl, keto, aldehyde, ether (cyclic and non-cyclic) and ester (cyclic and non-cyclic). They also may contain one or more C=C double bond, each double bond may be of the cis, trans, E- or Z-type, as well as monosubstituted, disubstituted, trisubstituted or tetrasubstituted (meaning no vinylic H-substituent), independently from other C=C bonds.

As used herein, "neutral triterpenoids" refer to triterpenoid compounds lacking a carboxylic acid group. The neutral triterpenoids may contain one or more other oxygen-containing functional groups for example, but not limited to, hydroxyl, keto, aldehyde, ether (cyclic and non-cyclic) and ester (cyclic and non-cyclic). They also may contain one or more C=C double bond, each double bond may be of the cis, trans, E- or Z-type, as well as monosubstituted, disubstituted, trisubstituted or tetrasubstituted (meaning no vinylic H-substituent), independently from other C=C bonds.

As used herein, "an oligomeric form of a terpenoic acid" refers to an oligomeric terpenoid acid in which the monomeric units are either of the same terpenoic acid or of different terpenoic acids, and are joined in any possible arrangements, and are connected one to another through any possible bond or functional group, such as a C—C bond, but not limited to, an ester group or an ether group.

As used herein, "an oligomeric form of a triterpenoic acid" refers to an oligomeric triterpenoid acid in which the monomeric units are either of the same triterpenoic acid or of different triterpenoic acids, and are joined in any possible arrangements, and are connected one to another through any possible bond or functional group, such as, but not limited to, a C—C bond, an ester group or an ether group.

As used herein, the terms "mastic", "mastic resin", "gum mastic" and "mastic gum", are used interchangeably to refer to a tree resin (also known as an oleoresin) obtained as an exudate from any tree classified in the family Anacardiaceae. Trees in the genus *Pistacia*, most notably *Pistacia lentiscus* L., and in particular the cultivar *P. lentiscus* L. cv. *Chia* (cultivated on the Greek island of Chios), are known for their high yield of gum mastic. Other varieties include *P. lentiscus* L. var. *emarginate* Engl., and *P. lentiscus* L. var. *latifolia* Coss. Additional species of *Pistacia* include for example, *P. atlantica, P. palestina, P. saportae, P. terebinthus, P. vera* and *P. integerrima*.

As used herein, the terms "masticadienoic acid", "masticadienonic acid", "masticadienoic" and "masticadienonic" may interchangeably be used.

As used herein, the terms "isomasticadienoic acid", "isomasticadienonic acid", "isomasticadienoic" and "isomasticadienonic" may interchangeably be used.

In order to provide clarity with respect to the molecular structure of compounds frequently mentioned and referred to in this application, a list of structures with names and acronyms used in this application is presented below.

Masticadienonic acid refers to 24-Z-masticadienonic acid, the acronym MDA used in the current application refers to this compound. The chemical structure of 24-Z-masticadienonic acid is as follows:

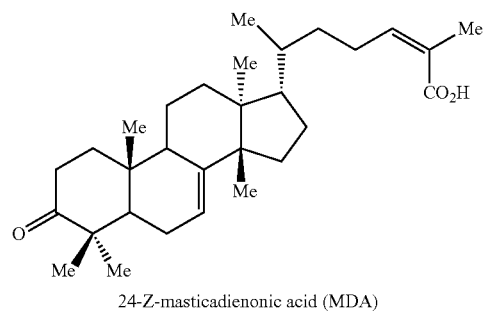
24-Z-masticadienonic acid (MDA)

Isomasticadienonic acid refers to 24-Z-isomasticadienonic acid, the acronym IMDA used in the current application refers to this compound. The chemical structure of 24-Z-isomasticadienonic acid is as follows:

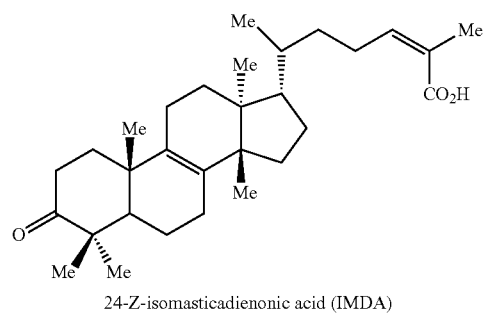
24-Z-isomasticadienonic acid (IMDA)

Oleanonic acid (OLN or OA) has the following molecular structure:

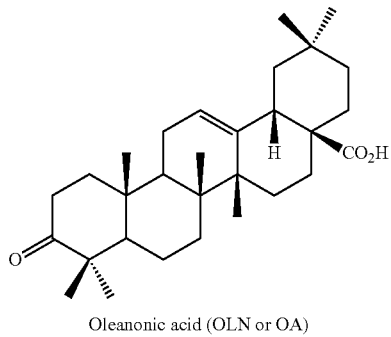
Oleanonic acid (OLN or OA)

Moronic acid (MO or MA) has the following molecular structure:

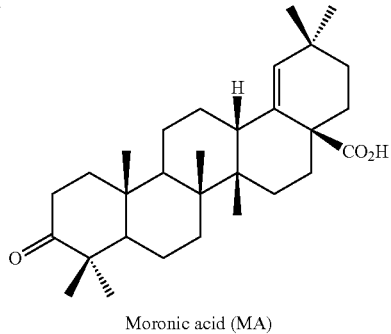
Moronic acid (MA)

24-Z-masticadienolic acid (MLA) has the following structure, the 3-hydroxyl group has the beta-configuration:

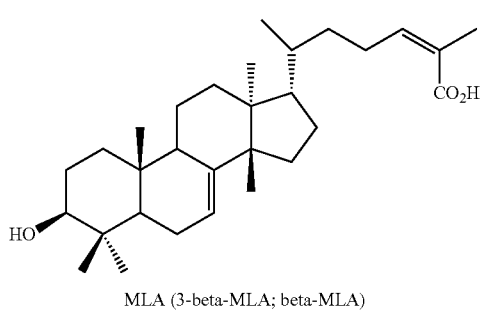

MLA (3-beta-MLA; beta-MLA)

24-Z-epimasticadienolic acid (epi-MLA) has the following structure, the 3-hydroxyl group has the alpha-configuration:

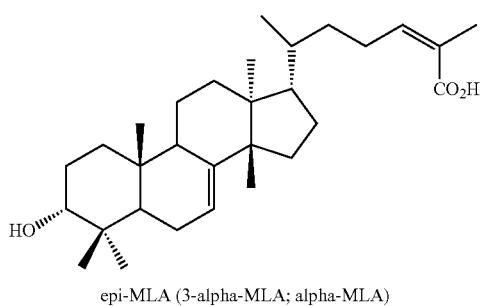

epi-MLA (3-alpha-MLA; alpha-MLA)

24-Z-isomasticadienolic acid (IMLA) has the following structure, the 3-hydroxyl group has the beta-configuration:

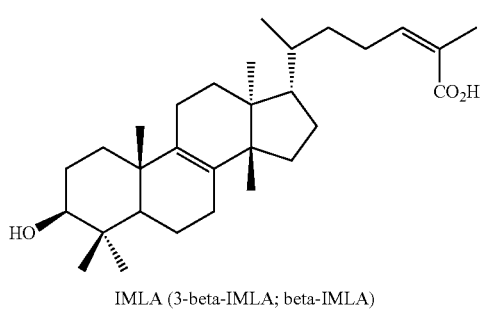

IMLA (3-beta-IMLA; beta-IMLA)

24-Z-epi-isomasticadienolic acid (epi-IMLA) has the following structure, the 3-hydroxyl group has the beta-configuration:

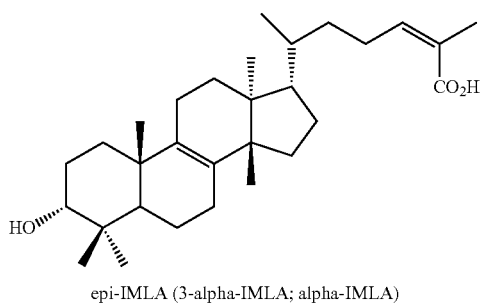

epi-IMLA (3-alpha-IMLA; alpha-IMLA)

24-Z-3-O-acetyl-masticadienolic acid has the following molecular structure:

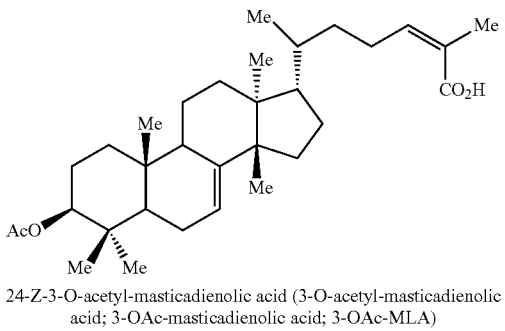

24-Z-3-O-acetyl-masticadienolic acid (3-O-acetyl-masticadienolic acid; 3-OAc-masticadienolic acid; 3-OAc-MLA)

24-Z-3-O-acetyl-epimasticadienolic acid has the following molecular structure:

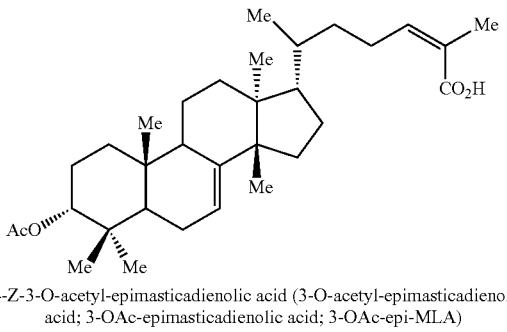

24-Z-3-O-acetyl-epimasticadienolic acid (3-O-acetyl-epimasticadienolic acid; 3-OAc-epimasticadienolic acid; 3-OAc-epi-MLA)

24-Z-3-O-acetyl-isomasticadienolic acid has the following molecular structure:

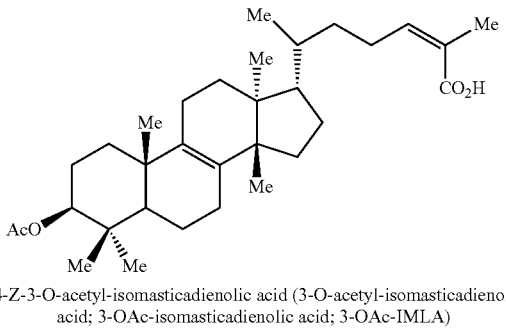

24-Z-3-O-acetyl-isomasticadienolic acid (3-O-acetyl-isomasticadienolic acid; 3-OAc-isomasticadienolic acid; 3-OAc-IMLA)

24-Z-3-O-acetyl-epiisomasticadienolic acid has the following molecular structure:

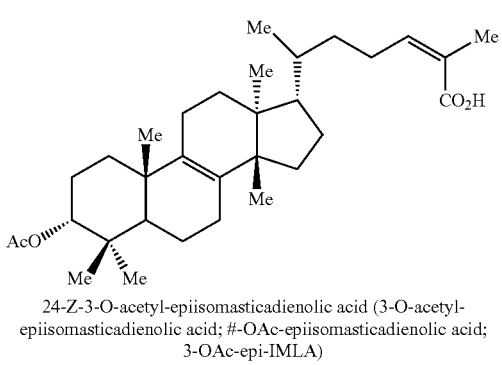

24-Z-3-O-acetyl-epiisomasticadienolic acid (3-O-acetyl-epiisomasticadienolic acid; #-OAc-epiisomasticadienolic acid; 3-OAc-epi-IMLA)

The term "NF-1" is directed to the neutral triterpenoid compound (8R)-3-beta, 8-dihydroxypolypoda-13E,17E,21-triene (also referred to as Myrrhanol C), having the structure as set forth in scheme I:

Scheme I

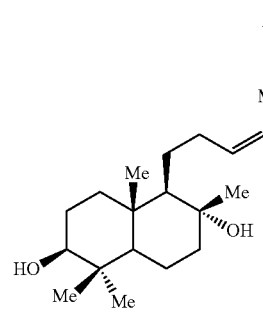

The term "NF-2" is directed to the neutral triterpenoid compound ((8R)-3-Oxo-8-hydroxypolypoda-13E,17E,21-triene, having the structure as set forth in scheme II:

Scheme II

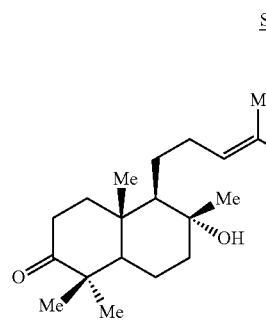

The term "NF-3" is directed to the neutral triterpenoid compound Oleanonic aldehyde, having the structure as set forth in scheme III:

Scheme III

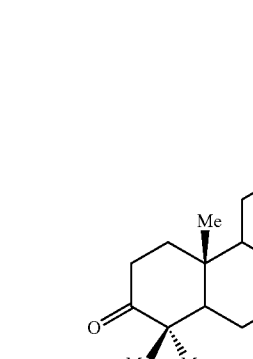

The term "NF-4" is directed to the neutral triterpenoid compound Tirucallol (C-20 Epimer of Euphol), having the structure as set forth in scheme IV:

Scheme IV

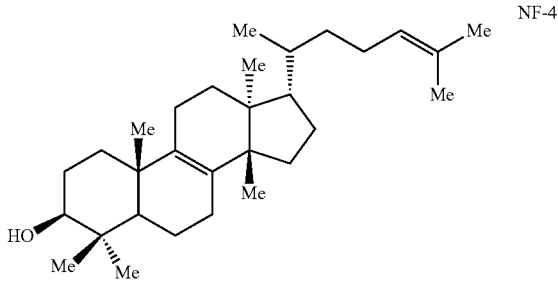

The term "NF-A" is directed to the neutral triterpenoid compound 28-hydroxylup-20(29)-en-3-one (also referred to as Betulon), having the structure as set forth in scheme V:

Scheme V

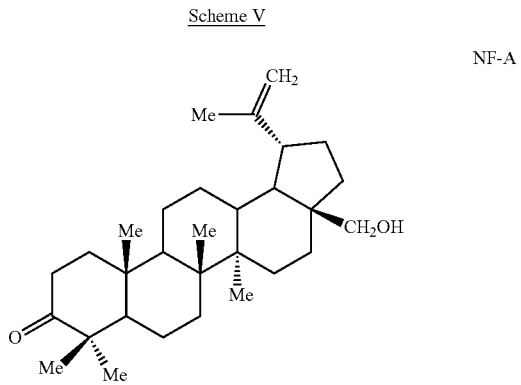

The term "NF-B" is directed to the neutral triterpenoid compound 28-hydroxy-beta-amyrone (also referred to as Oleanonic alcohol), having the structure as set forth in scheme VI:

Scheme VI

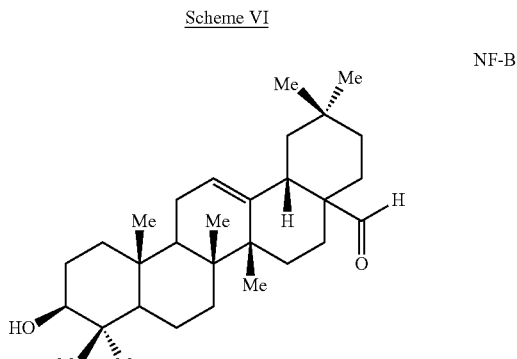

The term "NF-P" is directed to the neutral triterpenoid compound 20-hydroxydammar-24-en-3-one (also referred to as Dipterocarpol), having the structure as set

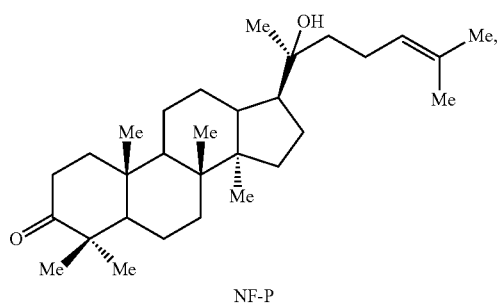

20-hydroxydammar-24-en-3-one (NF-P; Dipterocarpol)

Additional neutral triterpenoids isolated from mastic gum neutral fraction are the following:

Name: 3-beta-20-dihydroxylupane

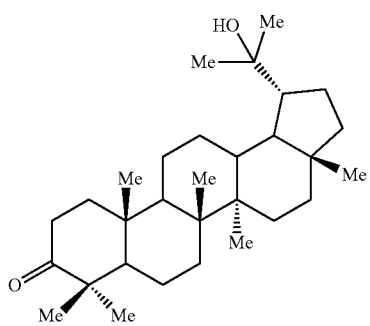

Name: 3-beta-hydroxy-13-alpha-malabarica-14(26), 17E, 21-triene

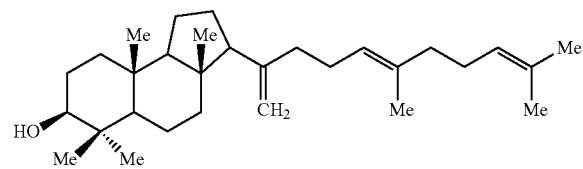

Name: 3-oxo-malabarica-14(26), 17E, 21-triene

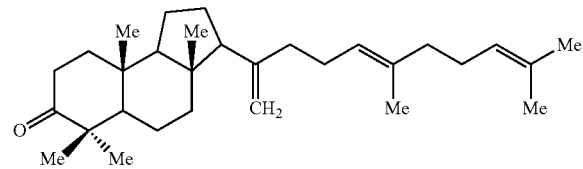

Name: Isomasticadienediol

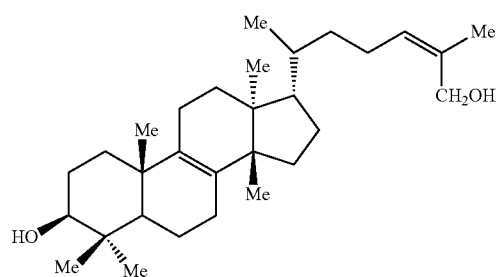

Name: Maticadienediol

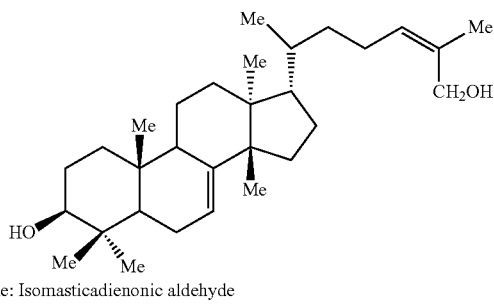

Name: Isomasticadienonic aldehyde

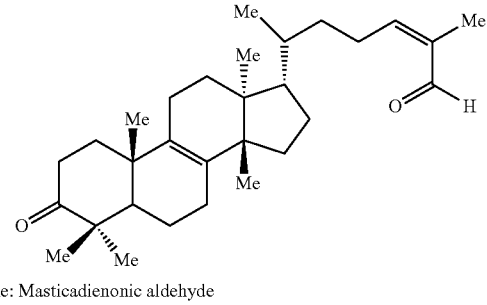

Name: Masticadienonic aldehyde

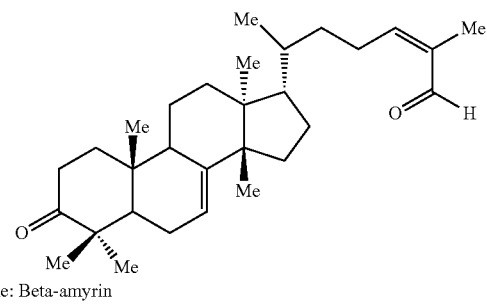

Name: Beta-amyrin

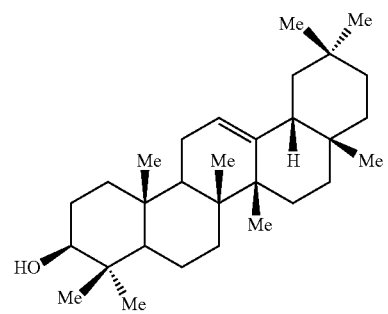

Beta-amyrin

Name: Beta-amyrone

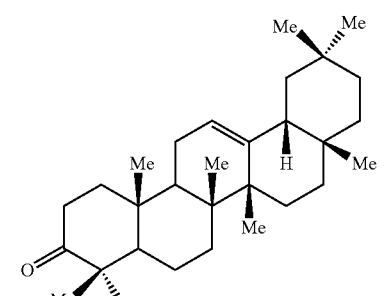

Beta-amyrone

-continued

Name: Germanicol

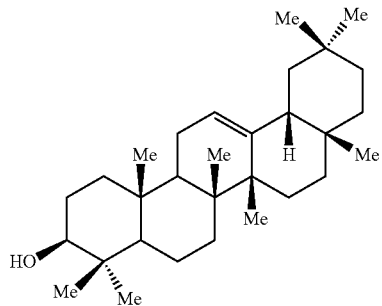
Germanicol

Name: 28-nor-beta-amyrin

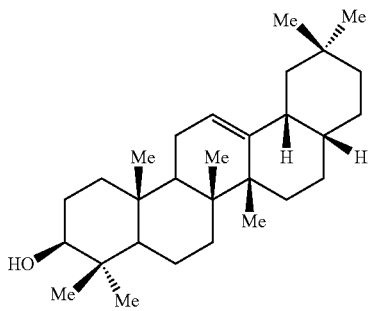
28-nor-beta-amyrin

Name: 28-nor-beta-amyrone

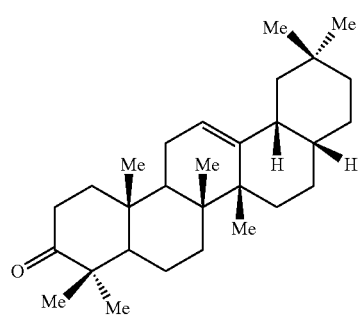
28-nor-beta-amyrone

Name: 3-oxo-28-norlup-20(29)-ene (28-nor-betulone)

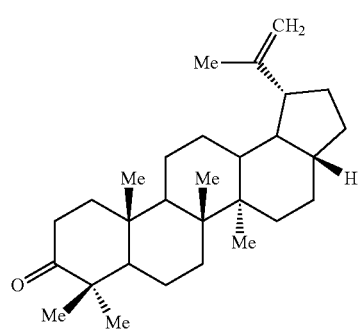

Name: 3-oxo-28-nor-17-hydroxy-20(29)-ene (28-nor-17-hydroxybetulone)

-continued

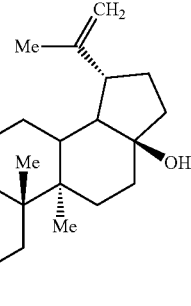

As used herein, the term "essential oil" means a volatile oil derived from the leaves, stem, flower or twigs of plants or synthetically-made compounds that have the same chemical attributes. The essential oil usually carries the odor or flavor of the plant. Each plant essential oil or derivative thereof may be extracted from natural sources or synthetically made. Chemically essential oils generally contain mixtures of mono- and sesquiterpenes or corresponding mixtures of such terpenoids as major constituents, which have lower molecular weights in comparison with triterpenes and titerpenoids. Particularly, this group comprise saturated and unsaturated acyclic monoterpenes or sesquiterpenes including alcohol or aldehyde moieties, benzenoid aromatic compounds containing at least one oxygenated substituent or side chain, or a monocarbocyclic terpene generally having a six-membered ring bearing one or more oxygenated substituents. The mastic resin contains about 2-4% of such compounds. As used herein, "essential oil" further includes derivatives thereof, including racemic mixtures, enantiomers, diastereomers, hydrates, salts, solvates, metabolites, analogs, and homologs.

As used herein, "substantially devoid" means that a preparation or pharmaceutical composition according to the invention that generally contains less than about 5% of the stated substance. For example, less than about 3%, less than 1%, less than 0.5%, less than 0.1%.

As used herein, the term "consisting essentially of" means that the only active pharmaceutical ingredient in the formulation or method that treats a specified condition is the specifically recited therapeutic ingredient in the particular embodiment or claim. The presence of other ingredients, e.g., excipients and/or lubricants, etc., is not precluded. The presence of additional other pharmaceutically active agents is also not precluded, as long as the latter do not have actual effect on said condition.

As used herein, "therapeutically effective amount" refers to that amount of a pharmaceutical ingredient which substantially induces, promotes or results in a desired therapeutic effect.

As used herein, "pharmaceutically acceptable carrier" refers to a diluent or vehicle, which is used to enhance the delivery and/or pharmacokinetic properties of a pharmaceutical ingredient with which it is formulated, but has no therapeutic effect of its own, nor does it induce or cause any undesirable or untoward effect or adverse reaction in the subject.

As used herein, "pharmaceutically acceptable hydrophobic carrier" refers to a hydrophobic non-polar diluent or vehicle in which a composition is dissolved or suspended.

As used herein, the terms "optic neuropathy" and "optic atrophy" may interchangeably be used. The terms refer to damage to the optic nerve due to any cause. The terms further encompass any condition or disorder resulting from or related to optic neuropathy, such as, ischemic optic neuropathy (including nonarteritic Anterior Ischemic Optic neuropathy (NAION), Anterior ischemic optic neuropathy (AION), Posterior ischemic optic neuropathy); Radiation optic neuropathy (RON)); Traumatic optic neuropathy, Glaucoma, Optic neuritis, Compressive optic neuropathy, Infiltrative optic neuropathy, Mitochondrial optic neuropathy, Nutritional optic neuropathies, toxic optic neuropathies, Hereditary optic neuropathy, damage resulting from storage disease, and the like; or combinations thereof. Each possibility is a separate embodiment.

As used herein, the term "storage disease" refers to any type of metabolic disorder that lead to excessive accumulation of substances such as lipids, proteins, lipoproteins, carbohydrates and others, of normal or abnormal nature. Of particular importance is the accumulation of lipofuscin associated with pathological damage to the optic nerve.

Numerical values stated herein are to be understood as the stated value +/−10%.

As used herein the term "about" in reference to a numerical value stated herein is to be understood as the stated value +/−10%.

Compositions Comprising Triterpenoic Acids and Neutral Triterpenoids

In some embodiments, the present invention provides compositions comprising or consisting of specific triterpenoic acids and neutral triterpenoids, these compositions are shown to have an unexpected synergetic therapeutic effect in the treatment of optic neuropathy conditions.

The triterpenoic acids and neutral triterpenoid compounds may be obtained from a plant source, such as for example mastic gum, or may be the products of chemical synthesis reactions. In some embodiments, any one of the triterpenoic acids and neutral triterpenoids may be the product of a biochemical reaction or a product produced by a microbial organism. In some embodiments, any one of the triterpenoic acids and neutral triterpenoids may be the product of a fermentation process. In some embodiments, any one of the triterpenoic acids and neutral triterpenoids may be produced by a combination of a chemical synthesis and a biochemical reaction. In some embodiments, any one of the triterpenoic acids and neutral triterpenoids may be produced by a combination of a chemical synthesis and a fermentation process. In some embodiments, any one of the triterpenoic acids and neutral triterpenoids may be produced by a combination of any of the above indicated options. In case of a biochemical reaction or microbial process, the biochemical agent and the microbial agent may be a naturally occurring agent or may be a modified agent not naturally occurring. Modification of these agents may have been achieved using modern biochemical methods such as for example genetic engineering. Said biochemical agents and microbial agents not occurring naturally may also have been created using synthetic biology methods.

The current invention relates to the unexpected biological and pharmaceutical properties of the disclosed pharmaceutical compositions comprising triterpenoic acid(s) and neutral triterpenoid(s). The combination of triterpenoic acid(s) and neutral triterpenoid(s) results in an overall pharmaceutical activity which cannot be obtained by using only the triterpenoic acids or only the neutral triterpenoids.

In some embodiments, the compositions may correspond to combinations of compounds in which some are chemically synthesized and some are derived from plant sources.

In some embodiments, the compositions may correspond to combinations of compounds in which each compound may independently have been derived from a plant source, or may be the product of a chemical synthesis, a biochemical reaction, or a microbial process (e.g. fermentation) as indicated above.

In some embodiments, the present invention provides compositions comprising combinations comprising at least one triterpenoic acid and at least one neutral triterpenoid having therapeutic activity, as detailed herein. In some embodiments, the present invention provides compositions comprising combinations comprising at least one triterpenoic acid and at least one neutral triterpenoid having therapeutic activity, and a pharmaceutically acceptable carrier. In some embodiments, there is provided a composition comprising at least one triterpenoic acid, at least one neutral triterpenoid and a pharmaceutically acceptable carrier.

In some embodiments, there is provided a composition comprising or consisting of at least one triterpenoic acid, at least one neutral triterpenoid and a pharmaceutically acceptable carrier.

In some embodiments, the triterpenoic acid may be selected from at least one of masticadienonic acid (MDA), isomasticadienonic acid (IMDA), masticadienolic acid (MLA), isomasticadienolic acid (IMLA), 3-O-acetyl-masticadienolic acid, 3-O-acetyl-epimasticadienolic acid, 3-O-acetyl-isomasticadienolic acid, 3-O-acetyl-epi-isomasticadienolic acid, oleanonic acid (OA) and moronic acid (MA), or any combination thereof. Each possibility is a separate embodiment. In some embodiments, the triterpenoic acid comprises or consists of at least one of masticadienonic acid (MDA), isomasticadienonic acid (IMDA), masticadienolic acid (MLA), isomasticadienolic acid (IMLA), 3-O-acetyl-masticadienolic acid, 3-O-acetyl-epimasticadienolic acid, 3-O-acetyl-isomasticadienolic acid, 3-O-acetyl-epi-isomasticadienolic acid, oleanonic acid (OA) and moronic acid (MA), or any combination thereof.

In some embodiments, the composition comprises or consists of at least two triterpenoic acids. In some embodiments, the composition comprises or consists of at least three triterpenoic acids. In some embodiments, the composition comprises or consists of at least four triterpenoic acids. In some embodiments, the composition comprises or consists of at least five triterpenoic acids. In some embodiments, the composition comprises or consists of at least six triterpenoic acids. In some embodiments, the composition comprises or consists of at least seven triterpenoic acids. In some embodiments, the composition comprises or consists of at least eight triterpenoic acids. In some embodiments, the composition comprises or consists of at least nine triterpenoic acids. In some embodiments, the composition comprises or consists of at least ten triterpenoic acids. In some embodiments, the composition comprises or consists of not more than two triterpenoic acids. In some embodiments, the composition comprises or consists of not more than three triterpenoic acids. In some embodiments, the composition comprises or consists of not more than four triterpenoic acids. In some embodiments, the composition comprises or consists of not more than five triterpenoic acids. In some embodiments, the composition comprises or consists of not more than six triterpenoic acids. In some embodiments, the composition comprises or consists of not more than seven triterpenoic acids. In some embodiments, the composition comprises or consists of not more than eight triterpenoic acids. In some embodiments, the composition comprises or consists of not more than nine triterpenoic acids. In some embodiments, the composition comprises or consists not more than ten triterpenoic acids.

In some embodiments, the at least one triterpenoic acid(s) comprises or consists of at least one of MDA, IMDA, MLA, IMLA, 3-O-acetyl-masticadienolic acid, 3-O-acetyl-epimasticadienolic acid, 3-O-acetyl-isomasticadienolic acid, 3-O-acetyl-epi-isomasticadienolic acid, OA and MA. Each possibility is a separate embodiment. In some embodiments, the triterpenoic acid(s) comprises or consists of at least MDA, IMDA, MLA, IMLA, 3-O-acetyl-masticadienolic acid, 3-O-acetyl-isomasticadienolic acid, OA and MA. In some embodiments, the triterpenoic acid(s) comprises or consists of at least MDA, IMDA, MLA and IMLA. In some embodiments, the triterpenoic acid comprises or consists of at least MDA and IMDA. In some embodiments, the triterpenoic acid comprises or consists of at least MDA. In some embodiments, the triterpenoic acid comprises at least IMDA.

In some embodiments, the triterpenoic acid is selected from MDA, IMDA, MLA, IMLA, 3-O-acetyl-masticadienolic acid, 3-O-acetyl-epimasticadienolic acid, 3-O-acetyl-isomasticadienolic acid, 3-O-acetyl-epi-isomasticadienolic acid, OA and MA. Each possibility is a separate embodiment. In some embodiments, the triterpenoic acid is selected from MDA, IMDA, MLA, IMLA, 3-O-acetyl-masticadienolic acid, 3-O-acetyl-isomasticadienolic acid, OA and MA. In some embodiments, the triterpenoic acid is selected from MDA, IMDA, MLA and IMLA. In some embodiments, the triterpenoic acid is selected from MDA and IMDA.

In some embodiments, the triterpenoic acid consists of MDA, IMDA, MLA, IMLA, 3-O-acetyl-masticadienolic acid, 3-O-acetyl-epimasticadienolic acid, 3-O-acetyl-isomasticadienolic acid, 3-O-acetyl-epi-isomasticadienolic acid, OA and MA. Each possibility is a separate embodiment. In some embodiments, the triterpenoic acid consists of MDA, IMDA, MLA, IMLA, 3-O-acetyl-masticadienolic acid, 3-O-acetyl-isomasticadienolic acid, OA and MA. In some embodiments, the triterpenoic acid consists of MDA, IMDA, MLA and IMLA. In some embodiments, the triterpenoic acid consists of MDA and IMDA.

In some embodiments, the neutral triterpenoid may be selected from at least one of (8R)-3-beta, 8-dihydroxypolypoda-13E,17E,21-triene (8-dihydroxypolypoda-13E,17E,21-triene; NF-1), (8R)-3-Oxo-8-hydroxypolypoda-13E,17E,21-triene (NF-2), Oleanonic aldehyde (NF-3), Tirucallol (NF-4), 28-hydroxylup-20(29)-en-3-one (NF-A), 28-hydroxy-beta-amyrone (NF-B), 20-hydroxydammar-24-en-3-one (NF-P), 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin, Germanicol, or any combination thereof. Each possibility is a separate embodiment.

In some embodiments, the neutral triterpenoid may be selected from at least one of (8R)-3-beta, 8-dihydroxypolypoda-13E,17E,21-triene (8-dihydroxypolypoda-13E,17E,21-triene; NF-1), (8R)-3-Oxo-8-hydroxypolypoda-13E,17E,21-triene (NF-2), Oleanonic aldehyde (NF-3), Tirucallol (NF-4), 28-hydroxylup-20(29)-en-3-one (NF-A), 28-hydroxy-beta-amyrone (NF-B), 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin, Germanicol, or any combination thereof. Each possibility is a separate embodiment.

In some embodiments, 20-hydroxydammar-24-en-3-one (NF-P) is not present in the pharmaceutical composition.

In some embodiments, the neutral triterpenoid comprises or consists of at least one of (8R)-3-beta, 8-dihydroxypolypoda-13E,17E,21-triene (8-dihydroxypolypoda-13E,17E,21-triene; NF-1), (8R)-3-Oxo-8-hydroxypolypoda-13E,17E,21-triene (NF-2), Oleanonic aldehyde (NF-3), Tirucallol (NF-4), 28-hydroxylup-20(29)-en-3-one (NF-A), 28-hydroxy-beta-amyrone (NF-B), 20-hydroxydammar-24-en-3-one (NF-P), 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and Germanicol. Each possibility is a separate embodiment.

In some embodiments, the neutral triterpenoid comprises or consists of at least one of (8R)-3-beta, 8-dihydroxypolypoda-13E,17E,21-triene (8-dihydroxypolypoda-13E,17E,21-triene; NF-1), (8R)-3-Oxo-8-hydroxypolypoda-13E,17E,21-triene (NF-2), Oleanonic aldehyde (NF-3), Tirucallol (NF-4), 28-hydroxylup-20(29)-en-3-one (NF-A), 28-hydroxy-beta-amyrone (NF-B), 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and Germanicol. Each possibility is a separate embodiment.

In some embodiments, the neutral triterpenoid does not comprise 20-hydroxydammar-24-en-3-one (NF-P).

In some embodiments, the neutral triterpenoid does not consist of 20-hydroxydammar-24-en-3-one (NF-P).

In some embodiments, the neutral triterpenoid comprises or consists of at least two neutral triterpenoids. In some embodiments, the neutral triterpenoid comprises or consists of at least three neutral triterpenoids. In some embodiments, the neutral triterpenoid comprises or consists of at least four neutral triterpenoids. In some embodiments, the neutral triterpenoid comprises or consists of at least five neutral triterpenoids. In some embodiments, the neutral triterpenoid comprises or consists of at least six neutral triterpenoids. In some embodiments, the neutral triterpenoid comprises or consists of at least seven neutral triterpenoids. In some embodiments, the neutral triterpenoid comprises or consists of not more than two neutral triterpenoids. In some embodiments, the neutral triterpenoid comprises or consists of not more than three neutral triterpenoids. In some embodiments, the neutral triterpenoid comprises or consists of not more than four neutral triterpenoids. In some embodiments, the neutral triterpenoid comprises or consists of not more than five neutral triterpenoids. In some embodiments, the neutral triterpenoid comprises or consists of not more than six neutral triterpenoids. In some embodiments, the neutral triterpenoid comprises or consists of not more than seven neutral triterpenoids.

In some embodiments, the neutral triterpenoid comprises at least NF-1, NF-2, NF-3, NF-4, NF-A, NF-B, NF-P, 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and Germanicol. Each possibility is a separate embodiment. In some embodiments, the neutral triterpenoid comprises at least NF-1, NF-2, NF-3, NF-4, NF-A, NF-B and NF-P. In some embodiments, the neutral triterpenoid comprises at least NF-1, NF-2, NF-3, NF-4, NF-A and NF-B. In some embodiments, the neutral triterpenoid comprises at least NF-1, NF-2, NF-3 and NF-4. In some embodiments, the neutral triterpenoid comprises at least NF-1, NF-2 and NF-3. In some embodiments, the neutral triterpenoid comprises at least NF-1, NF-2 and NF-4. In some embodiments, the neutral triterpenoid comprises at least NF-1, NF-3 and NF-4. In some embodiments, the neutral triterpenoid comprises at least NF-2, NF-3 and NF-4. In some embodiments, the neutral triterpenoid comprises at least NF-1 and NF-2. In some embodiments, the neutral triterpenoid comprises at least NF-1. In some embodiments, the neutral triterpenoid comprises at least NF-2. In some embodiments, the neutral triterpenoid comprises at least NF-3. In some embodiments, the neutral triterpenoid comprises at least NF-4. In some embodiments, the neutral triterpenoid comprises at least NF-A. In some embodiments, the neutral triterpenoid comprises at least NF-B.

In some embodiments, the neutral triterpenoid is selected from NF-1, NF-2, NF-3, NF-4, NF-A, NF-B, NF-P, 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and Germanicol. Each possibility is a separate embodiment.

In some embodiments, the neutral triterpenoid is selected from NF-1, NF-2, NF-3, NF-4, NF-A, NF-B and NF-P. In some embodiments, the neutral triterpenoid is selected from NF-1, NF-2, NF-3, NF-4, NF-A and NF-B. In some embodiments, the neutral triterpenoid is selected from NF-1, NF-2, NF-3 and NF-4. In some embodiments, the neutral triterpenoid is selected from NF-1, NF-2 and NF-3. In some embodiments, the neutral triterpenoid is selected from NF-1, NF-2 and NF-4. In some embodiments, the neutral triterpenoid is selected from NF-1 and NF-2.

In some embodiments, the neutral triterpenoid consists of NF-1, NF-2, NF-3, NF-4, NF-A, NF-B, NF-P, 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and Germanicol. Each possibility is a separate embodiment. In some embodiments, the neutral triterpenoid consists of NF-1, NF-2, NF-3, NF-4, NF-A, NF-B and NF-P. In some embodiments, the neutral triterpenoid consists of NF-1, NF-2, NF-3 and NF-4.

In some embodiments, the neutral triterpenoid consists of NF-3 and NF-4. In some embodiments, the neutral triterpenoid consists of NF-1 and NF-2.

In some embodiments, there is provided a pharmaceutical composition comprising pharmaceutically active ingredients comprising or consisting essentially of MA, OA, MDA, IMDA 3-O-acetyl masticadienolic acid, 3-O-acetyl isomasticadienolic acid, MLA, IMLA, NF-1, NF-2, NF-3 and NF-4; and a pharmaceutically acceptable carrier.

In some embodiments, there is provided a pharmaceutical composition comprising pharmaceutically active ingredients comprising or consisting essentially of MDA, IMDA, MLA, IMLA, NF-1, NF-2, NF-3, NF-4, NF-A and NF-B; and a pharmaceutically acceptable carrier.

In some embodiments, there is provided a pharmaceutical composition comprising pharmaceutically active ingredients comprising or consisting essentially of MDA, IMDA, MLA, IMLA, NF-1, NF-2, NF-3, NF-4, NF-P, NF-A and NF-B; and a pharmaceutically acceptable carrier.

In some embodiments, there is provided a pharmaceutical composition comprising pharmaceutically active ingredients comprising or consisting essentially of MDA, IMDA, NF-1, NF-2, NF-3 and NF-4; and a pharmaceutically acceptable carrier.

In some embodiments, there is provided a pharmaceutical composition comprising pharmaceutically active ingredients comprising or consisting essentially of MA, OA, MDA, IMDA, 3-O-acetyl masticadienolic acid, 3-O-acetyl isomasticadienolic acid, MLA, IMLA, NF-1, NF-2, NF-3, NF-4, NF-P, NF-A and NF-B as the sole pharmaceutically active ingredients; and a pharmaceutically acceptable carrier.

In some embodiments, there is provided a pharmaceutical composition comprising pharmaceutically active ingredients comprising or consisting essentially of MA, OA, MDA, IMDA, 3-O-acetyl masticadienolic acid, 3-O-acetyl isomasticadienolic acid, MLA, IMLA, NF-1, NF-2, NF-3, NF-4, NF-A and NF-B as the sole pharmaceutically active ingredients; and a pharmaceutically acceptable carrier.

In some embodiments, there is provided a pharmaceutical composition comprising pharmaceutically active ingredients comprising or consisting essentially of MDA, IMDA, NF-1, NF-2, NF-3, NF-4, NF-P, NF-A and NF-B as the sole pharmaceutically active ingredients; and a pharmaceutically acceptable carrier.

In some embodiments, there is provided a pharmaceutical composition comprising pharmaceutically active ingredients comprising or consisting essentially of MDA, IMDA, NF-1, NF-2, NF-3, NF-4, NF-A and NF-B as the sole pharmaceutically active ingredients; and a pharmaceutically acceptable carrier.

In some embodiments, the triterpenoic acid(s) may be obtained from a plant source. In some embodiments, any one of the triterpenoic acids may be obtained from a plant source. In some embodiments, at least one triterpenoic acid may be obtained from a plant source. In some embodiments, the neutral triterpenoid(s) may be obtained from a plant source. In some embodiments, the neutral triterpenoid(s) may be isolated. In some embodiments, any one of the neutral triterpenoids may be obtained from a plant source. In some embodiments, at least one neutral triterpenoid may be obtained from a plant source. In some embodiments, the plant source may include mastic gum.

In some embodiments, the triterpenoic acid(s) may be obtained via a chemical synthesis. In some embodiments, any one of the triterpenoic acids may be obtained via a chemical synthesis. In some embodiments, at least one triterpenoic acid may be obtained via a chemical synthesis. In some embodiments, the neutral triterpenoid(s) may be obtained via a chemical synthesis. In some embodiments, any one of the neutral triterpenoids may be obtained via a chemical synthesis. In some embodiments, at least one neutral triterpenoid may be obtained via a chemical synthesis.

In some embodiments, the triterpenoic acid may be selected from at least one of masticadienonic acid (MDA), isomasticadienonic acid (IMDA), masticadienolic acid (MLA), isomasticadienolic acid (IMLA), 3-O-acetyl-masticadienolic acid, 3-O-acetyl-epimasticadienolic acid, 3-O-acetyl-isomasticadienolic acid, 3-O-acetyl-epi-isomasticadienolic acid, oleanonic acid (OA or OLN) and moronic acid (MA), or any combination thereof. Each possibility is a separate embodiment.

As designated herein, "Oleanonic acid" may interchangeably be referred to by the abbreviations OA or OLN.

As designated herein, "Moronic acid" may interchangeably be referred to by the abbreviations MA or MO.

In some embodiments, when MDA is one of the triterpenoic acids, MDA may comprise about 2-80% of the total weight of the triterpenoic acids. In some embodiments, MDA may comprise about 10-70% of the total weight of the triterpenoic acids. In some embodiments, MDA may comprise about 15-60% of the total weight of the triterpenoic acids. In some embodiments, MDA may comprise about 20-50% of the total weight of the triterpenoic acids. In some embodiments, MDA may comprise about 20-40% of the total weight of the triterpenoic acids. In some embodiments, MDA may comprise about 40-50% of the total weight of the triterpenoic acids. In some embodiments, MDA may comprise about 50% of the total weight of the triterpenoic acids.

In some embodiments, when IMDA is one of the triterpenoic acids, IMDA may comprise about 2-80% of the total weight of the triterpenoic acids. In some embodiments, IMDA may comprise about 10-70% of the total weight of the triterpenoic acids. In some embodiments, IMDA may comprise about 15-60% of the total weight of the triterpenoic acids. In some embodiments, IMDA may comprise about 20-50% of the total weight of the triterpenoic acids. In some embodiments, IMDA may comprise about 20-40% of the total weight of the triterpenoic acids. In some embodiments, IMDA may comprise about 40-50% of the total weight of the triterpenoic acids. In some embodiments, IMDA may comprise about 50% of the total weight of the triterpenoic acids.

In some embodiments, when MLA is one of the triterpenoic acids, MLA may comprise about 0-80% of the total weight of the triterpenoic acids. In some embodiments, MLA may comprise about 0-70% of the total weight of the triterpenoic acids. In some embodiments, MLA may comprise about 0-25% of the total weight of the triterpenoic acids. In some embodiments, MLA may comprise about 0-15% of the total weight of the triterpenoic acids. In some embodiments, MLA may comprise about 8% of the total weight of the triterpenoic acids.

In some embodiments, when IMLA is one of the triterpenoic acids, IMLA may comprise about 0-80% of the total weight of the triterpenoic acids. In some embodiments, IMLA may comprise about 0-70% of the total weight of the triterpenoic acids. In some embodiments, IMLA may comprise about 0-25% of the total weight of the triterpenoic acids. In some embodiments, IMLA may comprise about 0-15% of the total weight of the triterpenoic acids. In some embodiments, IMLA may comprise about 8% of the total weight of the triterpenoic acids.

In some embodiments, when MA is one of the triterpenoic acids, MA may comprise about 0-80% of the total weight of the triterpenoic acids. In some embodiments, MA may comprise about 0-70% of the total weight of the triterpenoic acids. In some embodiments, MA may comprise about 0-40% of the total weight of the triterpenoic acids. In some embodiments, MA may comprise about 0-30% of the total weight of the triterpenoic acids. In some embodiments, MA may comprise about 5-20% of the total weight of the triterpenoic acids. In some embodiments, MA may comprise about 12-15% of the total weight of the triterpenoic acids.

In some embodiments, when OA is one of the triterpenoic acids, OA may comprise about 0-80% of the total weight of the triterpenoic acids. In some embodiments, OA may comprise about 0-70% of the total weight of the triterpenoic acids. In some embodiments, OA may comprise about 0-50% of the total weight of the triterpenoic acids. In some embodiments, OA may comprise about 5-35% of the total weight of the triterpenoic acids. In some embodiments, OA may comprise about 10-25% of the total weight of the triterpenoic acids. In some embodiments, MA may comprise about 18-20% of the total weight of the triterpenoic acids.

In some embodiments, when 3-O-acetyl-masticadienolic acid is one of the triterpenoic acids, 3-O-acetyl-masticadienolic acid may comprise about 0-80% of the total weight of the triterpenoic acids. In some embodiments, 3-O-acetyl-masticadienolic acid may comprise about 0-70% of the total weight of the triterpenoic acids. In some embodiments, 3-O-acetyl-masticadienolic acid may comprise about 0-25% of the total weight of the triterpenoic acids. In some embodiments, 3-O-acetyl-masticadienolic acid may comprise about 0-15% of the total weight of the triterpenoic acids. In some embodiments, 3-O-acetyl-masticadienolic acid may comprise about 4-7% of the total weight of the triterpenoic acids.

In some embodiments, when 3-O-acetyl-isomasticadienolic acid is one of the triterpenoic acids, 3-O-acetyl-isomasticadienolic acid may comprise about 0-80% of the total weight of the triterpenoic acids. In some embodiments, 3-O-acetyl-isomasticadienolic acid may comprise about 0-70% of the total weight of the triterpenoic acids. In some embodiments, 3-O-acetyl-isomasticadienolic acid may comprise about 0-25% of the total weight of the triterpenoic acids. In some embodiments, 3-O-acetyl-isomasticadienolic acid may comprise about 0-15% of the total weight of the triterpenoic acids. In some embodiments, 3-O-acetyl-isomasticadienolic acid may comprise about 4-7% of the total weight of the triterpenoic acids.

In some embodiments, the neutral triterpenoid may be selected from at least one of (8R)-3-beta, 8-dihydroxypolypoda-13E,17E,21-triene (8-dihydroxypolypoda-13E,17E,21-triene; NF-1), (8R)-3-Oxo-8-hydroxypolypoda-13E,17E,21-triene (NF-2), Oleanonic aldehyde (NF-3), Tirucallol (NF-4), 28-hydroxylup-20(29)-en-3-one (NF-A), 28-hydroxy-beta-amyrone (NF-B), 20-hydroxydammar-24-en-3-one (NF-P), 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin, Germanicol, or any combination thereof. Each possibility is a separate embodiment.

In some embodiments, the neutral triterpenoid may be selected from at least one of (8R)-3-beta, 8-dihydroxypolypoda-13E,17E,21-triene (8-dihydroxypolypoda-13E,17E,21-triene; NF-1), (8R)-3-Oxo-8-hydroxypolypoda-13E,17E,21-triene (NF-2), Oleanonic aldehyde (NF-3), Tirucallol (NF-4), 28-hydroxylup-20(29)-en-3-one (NF-A), 28-hydroxy-beta-amyrone (NF-B), 20-hydroxydammar-24-en-3-one (NF-P), 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin, Germanicol, or any combination thereof. Each possibility is a separate embodiment.

In some embodiments, the neutral triterpenoid may be selected from at least one of (8R)-3-beta, 8-dihydroxypolypoda-13E,17E,21-triene (8-dihydroxypolypoda-13E,17E, 21-triene; NF-1), (8R)-3-Oxo-8-hydroxypolypoda-13E,17E, 21-triene (NF-2), Oleanonic aldehyde (NF-3), Tirucallol (NF-4), 28-hydroxylup-20(29)-en-3-one (NF-A), 28-hydroxy-beta-amyrone (NF-B), 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin, Germanicol, or any combination thereof. Each possibility is a separate embodiment.

In some embodiments, the neutral triterpenoid may be selected from at least one of (8R)-3-beta, 8-dihydroxypolypoda-13E,17E,21-triene (8-dihydroxypolypoda-13E,17E, 21-triene; NF-1), (8R)-3-Oxo-8-hydroxypolypoda-13E,17E, 21-triene (NF-2), Oleanonic aldehyde (NF-3), Tirucallol (NF-4), 28-hydroxylup-20(29)-en-3-one (NF-A), 28-hydroxy-beta-amyrone (NF-B), 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin, Germanicol, or any combination thereof. Each possibility is a separate embodiment.

In some embodiments, when NF-1 is one of the neutral triterpenoids, the amount of the NF-1 of the total amount of neutral triterpenoids may be in the range of about 0% to about 80%. In some embodiments, the amount of the NF-1 of the total amount of neutral triterpenoids may be in the range of about 0% to about 50%. In some embodiments, the amount of the NF-1 of the total amount of neutral triterpenoids may be in the range of about 5% to about 25%. In some embodiments, the amount of the NF-1 of the total amount of neutral triterpenoids may be in the range of about 9% to about 13%.

In some embodiments, when NF-2 is one of the neutral triterpenoids, the amount of the NF-2 of the total amount of neutral triterpenoids may be in the range of about 0% to about 80%. In some embodiments, the amount of the NF-2 of the total amount of neutral triterpenoids may be in the range of about 0% to about 50%. In some embodiments, the amount of the NF-2 of the total amount of neutral triterpenoids may be in the range of about 5% to about 25%. In some embodiments, the amount of the NF-2 of the total amount of neutral triterpenoids may be in the range of about 9% to about 13%.

In some embodiments, when NF-3 is one of the neutral triterpenoids, the amount of the NF-3 of the total amount of neutral triterpenoids may be in the range of about 0% to about 80%. In some embodiments, the amount of the NF-3 of the total amount of neutral triterpenoids may be in the range of about 0% to about 50%. In some embodiments, the amount of the NF-3 of the total amount of neutral triterpenoids may be in the range of about 5% to about 25%. In some embodiments, the amount of the NF-3 of the total amount of neutral triterpenoids may be in the range of about 9% to about 13%.

In some embodiments, when NF-4 is one of the neutral triterpenoids, the amount of the NF-4 of the total amount of neutral triterpenoids may be in the range of about 0% to about 80%. In some embodiments, the amount of the NF-4 of the total amount of neutral triterpenoids may be in the range of about 0% to about 50%. In some embodiments, the amount of the NF-4 of the total amount of neutral triterpenoids may be in the range of about 5% to about 25%. In some embodiments, the amount of the NF-4 of the total amount of neutral triterpenoids may be in the range of about 9% to about 13%.

In some embodiments, when NF-P is one of the neutral triterpenoids, the amount of the NF-P of the total amount of neutral triterpenoids may be in the range of about 0% to about 50%. In some embodiments, the amount of the NF-P of the total amount of neutral triterpenoids may be in the range of about 0% to about 25%. In some embodiments, the amount of the NF-P of the total amount of neutral triterpenoids may be in the range of about 0% to about 7%. In some embodiments, the amount of the NF-P of the total amount of neutral triterpenoids may be in the range of about 6% to about 7%.

In some embodiments, when NF-A is one of the neutral triterpenoids, the amount of the NF-A of the total amount of neutral triterpenoids may be in the range of about 0% to about 25%. In some embodiments, the amount of the NF-A of the total amount of neutral triterpenoids may be in the range of about 0% to about 15%. In some embodiments, the amount of the NF-A of the total amount of neutral triterpenoids may be in the range of about 0% to about 6%. In some embodiments, the amount of the NF-A of the total amount of neutral triterpenoids may be in the range of about 4% to about 6%.

In some embodiments, when NF-B is one of the neutral triterpenoids, the amount of the NF-B of the total amount of neutral triterpenoids may be in the range of about 0% to about 25%. In some embodiments, the amount of the NF-B of the total amount of neutral triterpenoids may be in the range of about 0% to about 15%. In some embodiments, the amount of the NF-B of the total amount of neutral triterpenoids may be in the range of about 0% to about 6%. In some embodiments, the amount of the NF-B of the total amount of neutral triterpenoids may be in the range of about 4% to about 6%.

In some embodiments, the triterpenoic acids may comprise from about 1% to about 80% of the total active ingredients of the composition. In some embodiments, the triterpenoic acids may comprise from about 10% to about 80% of the total active ingredients of the composition. In some embodiments, the triterpenoic acids may comprise from about 20% to about 80% of the total active ingredients of the composition. In some embodiments, the triterpenoic acids may comprise from about 30% to about 70% of the total active ingredients of the composition. In some embodiments, the triterpenoic acids may comprise from about 35% to about 65% of the total active ingredients of the composition. In some embodiments, the triterpenoic acids may comprise from about 40% to about 60% of the total active ingredients of the composition.

In some embodiments, the triterpenoic acids may comprise from about 0.01% to about 80% of the total composition. In some embodiments, the triterpenoic acids may comprise from about 0.01% to about 50% of the total composition. In some embodiments, the triterpenoic acids may comprise from about 0.01% to about 10% of the total composition. In some embodiments, the triterpenoic acids may comprise from about 0.1% to about 10% of the total composition. In some embodiments, the triterpenoic acids may comprise from about 0.5% to about 4% of the total composition. In some embodiments, the triterpenoic acids may comprise from about 1% to about 3.5% of the total composition. In some embodiments, the triterpenoic acids may comprise from about 1.5% to about 3% of the total composition. In some embodiments, the triterpenoic acids may comprise from about 1.75% to about 2.75% of the total composition. In some embodiments, the triterpenoic acids may comprise from about 2% to about 2.5% of the total composition.

In some embodiments, the neutral triterpenoids may comprise from about 1% to about 80% of the total active ingredients of the composition. In some embodiments, the neutral triterpenoids may comprise from about 10% to about 80% of the total active ingredients of the composition. In some embodiments, the neutral triterpenoids may comprise from about 20% to about 80% of the total active ingredients of the composition. In some embodiments, the neutral triterpenoids may comprise from about 30% to about 70% of the total active ingredients of the composition. In some embodiments, the neutral triterpenoids may comprise from about 35% to about 65% of the total active ingredients of the composition. In some embodiments, the neutral triterpenoids may comprise from about 40% to about 60% of the total active ingredients of the composition.

In some embodiments, the neutral triterpenoids may comprise from about 0.01% to about 80% of the total composition. In some embodiments, the neutral triterpenoids may comprise from about 0.01% to about 50% of the total composition. In some embodiments, the neutral triterpenoids may comprise from about 0.01% to about 10% of the total composition. In some embodiments, the neutral triterpenoids may comprise from about 0.1% to about 10% of the total composition. In some embodiments, the neutral triterpenoids may comprise from about 0.5% to about 4% of the total composition. In some embodiments, the neutral triterpenoids may comprise from about 1% to about 3.5% of the total composition. In some embodiments, the neutral triterpenoids may comprise from about 1.5% to about 3% of the total composition. In some embodiments, the neutral triterpenoids may comprise from about 1.75% to about 2.75% of the total composition. In some embodiments, the neutral triterpenoids may comprise from about 2% to about 2.5% of the total composition.

In some embodiments, the combinations may include at least MDA and IMDA as the triterpenoic acids and at least NF-1, NF-2, NF-3 and NF-4 as the neutral triterpenoids. In some embodiments, the combinations may include at least MDA and IMDA as the triterpenoic acids and at least NF-1, NF-2, NF-3, NF-4, NF-A, NF-B, NF-P as the neutral triterpenoids. In some embodiments, the combinations may include at least MDA and IMDA as the triterpenoic acids and at least NF-1, NF-2, NF-3, NF-4, NF-A, and NF-B as the neutral triterpenoids. In some embodiments, the combinations may include at least MDA, MLA, IMDA and IMLA as the triterpenoic acids and at least NF-1, NF-2, NF-3 and NF-4 as the neutral triterpenoids. In some embodiments, the combinations may include at least MDA, MLA, IMDA and IMLA as the triterpenoic acids and at least NF-1, NF-2, NF-3, NF-4, NF-A, NF-B and NF-P as the neutral triterpenoids. In some embodiments, the combinations may include at least MDA, MLA, IMDA and IMLA as the triterpenoic acids and at least NF-1, NF-2, NF-3, NF-4, NF-A and NF-B as the neutral triterpenoids. Such compositions unexpectedly exhibit a synergistic effect, whereby the combination of compounds exhibit a markedly improved therapeutic effect in the treatment of optic neuropathy conditions.

In some embodiments, the neutral triterpenoid comprises at least NF-1 and at least one additional neutral triterpenoid. In some embodiments, the neutral triterpenoid comprises at least NF-2 and at least one additional neutral triterpenoid. In some embodiments, the neutral triterpenoid comprises at least NF-1, NF-2 and at least one additional neutral triterpenoid. In some embodiments, the additional neutral triterpenoid is selected from the group consisting of NF-1, NF-2, NF-3, NF-4, NF-A, NF-B and NF-P. In some embodiments, the additional neutral triterpenoid is selected from the group consisting of NF-1, NF-2, NF-3, NF-4, NF-A and NF-B. Each possibility is a separate embodiment. In some embodiments, the additional neutral triterpenoid is selected from the group consisting of NF-2, NF-3, NF-4, NF-A, NF-B, and NF-P. In some embodiments, the additional neutral triterpenoid is selected from the group consisting of NF-2, NF-3, NF-4, NF-A and NF-B. In some embodiments, the additional neutral triterpenoid is selected from the group consisting of NF-1, NF-3, NF-4, NF-A, NF-B and NF-P. In some embodiments, the additional neutral triterpenoid is selected from the group consisting of NF-1, NF-3, NF-4, NF-A and NF-B. In some embodiments, the additional neutral triterpenoid is selected from the group consisting of NF-3, NF-4, NF-A, NF-B and NF-P. In some embodiments, the additional neutral triterpenoid is selected from the group consisting of NF-3, NF-4, NF-A and NF-B. In some embodiments, the additional neutral triterpenoid is selected from NF-3 and NF-4 (tirucallol). Various combinations of some of these compounds exhibit an unexpected synergistic effect in the treatment of optic neuropathy conditions.

In some embodiments, there is provided a composition comprising at least one of MDA, IMDA, MLA, IMLA, 3-O-acetyl-masticadienolic acid, 3-O-acetyl-epimasticadienolic acid, 3-O-acetyl-isomasticadienolic acid, 3-O-acetyl-epi-isomasticadienolic acid, OA and MA, in addition to at least one of NF-1, NF-2, NF-3, NF-4, NF-A, NF-B and NF-P. Each possibility is a separate embodiment of the invention.

In some embodiments, there is provided a composition comprising at least one of MDA, IMDA, MLA, IMLA, 3-O-acetyl-masticadienolic acid, 3-O-acetyl-epimasticadienolic acid, 3-O-acetyl-isomasticadienolic acid, 3-O-acetyl-epi-isomasticadienolic acid, OA and MA, in addition to at least one of NF-1, NF-2, NF-3, NF-4, NF-A and NF-B. Each possibility is a separate embodiment of the invention.

In some embodiments, the composition comprises at least one of masticadienonic acid MDA, IMDA, MLA, IMLA, 3-O-acetyl-masticadienolic acid, 3-O-acetyl-isomasticadienolic acid, OA and MA; in addition to at least one of NF-1, NF-2, NF-3 and NF-4. In some embodiments, the composition comprises at least one of MDA and IMDA; in addition to at least one of NF-1, NF-2, NF-3 and NF-4. In some embodiments, the composition comprises at least one of MDA and IMDA; in addition to at least one of NF-1, NF-2, NF-3, NF-4, NF-A, NF-B and NF-P. In some embodiments, the composition comprises at least one of MDA and IMDA; in addition to at least one of NF-1, NF-2, NF-3, NF-4, NF-A and NF-B. In some embodiments, the composition may further include a pharmaceutically acceptable carrier.

In some embodiments, there is provided a composition comprising at least one of NF-1 and NF-2, in addition to at least one of MDA, IMDA, MLA, IMLA, 3-O-acetyl-masticadienolic acid, 3-O-acetyl-epimasticadienolic acid, 3-O- acetyl-isomasticadienolic acid, 3-O-acetyl-epi-isomasticadienolic acid, OA and MA; and at least one of NF-3, NF-4, NF-A, NF-B and NF-P.

In some embodiments, there is provided a composition comprising at least one of NF-1 and NF-2, in addition to at least one of MDA, IMDA, MLA, IMLA, 3-O-acetyl-masticadienolic acid, 3-O-acetyl-epimasticadienolic acid, 3-O-acetyl-isomasticadienolic acid, 3-O-acetyl-epi-isomasticadienolic acid, OA and MA; and at least one of NF-3, NF-4, NF-A and NF-B.

In some embodiments, there is provided a composition comprising NF-1, NF-2, at least one of MDA, IMDA, MLA, IMLA, 3-O-acetyl-masticadienolic acid, 3-O-acetyl-epimasticadienolic acid, 3-O-acetyl-isomasticadienolic acid, 3-O-acetyl-epi-isomasticadienolic acid; OA, MA, and at least one of NF-3, NF-4, NF-A, NF-B and NF-P.

In some embodiments, there is provided a composition comprising NF-1, NF-2, at least one of MDA, IMDA, MLA, IMLA, 3-O-acetyl-masticadienolic acid, 3-O-acetyl-epimasticadienolic acid, 3-O-acetyl-isomasticadienolic acid, 3-O-acetyl-epi-isomasticadienolic acid; OA, MA, and at least one of NF-3, NF-4, NF-A and NF-B.

In some embodiments, there is provided a composition comprising at least one of NF-1 and NF-2, in addition to at least one of MDA, IMDA, MLA, IMLA, 3-O-acetyl-masticadienolic acid, 3-O-acetyl-isomasticadienolic acid, OA and MA, and at least one of NF-3 and NF-4.

In some embodiments, there is provided a composition comprising NF-1 and NF-2, in addition to at least one of masticadienonic acid MDA, IMDA, MLA, IMLA, 3-O-acetyl-masticadienolic acid, 3-O-acetyl-isomasticadienolic acid, OA and MA, and at least one of NF-3 and NF-4.

In some embodiments, there is provided a composition comprising at least one of NF-1 and NF-2 in addition to at least one of MDA, IMDA, MLA and IMLA, and at least one of NF-3, NF-4, NF-A, NF-B and NF-P.

In some embodiments, there is provided a composition comprising at least one of NF-1 and NF-2 in addition to at least one of MDA, IMDA, MLA and IMLA, and at least one of NF-3, NF-4, NF-A and NF-B.

In some embodiments, there is provided a composition comprising NF-1 and NF-2, in addition to at least one of MDA, IMDA, MLA and IMLA, and at least one of NF-3, NF-4, NF-A, NF-B and NF-P.

In some embodiments, there is provided a composition comprising NF-1 and NF-2, in addition to at least one of MDA, IMDA, MLA and IMLA, and at least one of NF-3, NF-4, NF-A and NF-B.

In some embodiments, there is provided a composition comprising at least one of NF-1 and NF-2, in addition to at least one of masticadienonic acid MDA and IMDA; and at least one of NF-3 and NF-4.

In some embodiments, there is provided a composition comprising NF-1 and NF-2, in addition to at least one of MDA and IMDA; and at least one of NF-3 and NF-4.

In some embodiments, there is provided a composition comprising at least one of NF-1 and NF-2, in addition to at least one of MDA, IMDA, MLA, IMLA, 3-O-acetyl-masticadienolic acid, 3-O-acetyl-isomasticadienolic acid, OA and MA, and at least one of NF-3, NF-4, NF-A, NF-B and NF-P.

In some embodiments, there is provided a composition comprising at least one of NF-1 and NF-2, in addition to at least one of MDA, IMDA, MLA, IMLA, 3-O-acetyl-masticadienolic acid, 3-O-acetyl-isomasticadienolic acid, OA and MA, and at least one of NF-3, NF-4, NF-A and NF-B.

In some embodiments, there is provided a composition comprising NF-1 and NF-2, in addition to at least one of MDA, IMDA, MLA, IMLA, 3-O-acetyl-masticadienolic acid, 3-O-acetyl-isomasticadienolic acid, OA and MA, and at least one of NF-3, NF-4, NF-A, NF-B and NF-P.

In some embodiments, there is provided a composition comprising NF-1 and NF-2, in addition to at least one of MDA, IMDA, MLA, IMLA, 3-O-acetyl-masticadienolic acid, 3-O-acetyl-isomasticadienolic acid, OA and MA, and at least one of NF-3, NF-4, NF-A and NF-B.

In some embodiments, there is provided a composition comprising at least one of NF-1 and NF-2, in addition to at least one of masticadienonic acid MDA and IMDA; and at least one of NF-3, NF-4, NF-A, NF-B and NF-P.

In some embodiments, there is provided a composition comprising at least one of NF-1 and NF-2, in addition to at least one of masticadienonic acid MDA and IMDA; and at least one of NF-3, NF-4, NF-A and NF-B.

In some embodiments, there is provided a composition comprising NF-1 and NF-2, in addition to at least one of MDA and IMDA and at least one of NF-3, NF-4, NF-A, NF-B and NF-P.

In some embodiments, there is provided a composition comprising NF-1 and NF-2, in addition to at least one of MDA and IMDA and at least one of NF-3, NF-4, NF-A and NF-B.

In some embodiments, the composition may include not more than 50 triterpenoids. In some embodiments, the composition may include not more than 40 triterpenoids. In some embodiments, the composition may include not more than 30 triterpenoids. In some embodiments, the composition may include not more than 25 triterpenoids. In some embodiments, the composition may include not more than 20 triterpenoids. In some embodiments, the composition may include not more than 15 triterpenoids. In some embodiments, the composition may include not more than 14 triterpenoids. In some embodiments, the composition may include not more than 13 triterpenoids. In some embodiments, the composition may include not more than 12 triterpenoids. In some embodiments, the composition may include not more than 11 triterpenoids. In some embodiments, the composition may include not more than 10 triterpenoids. In some embodiments, the composition may include not more than 9 triterpenoids. In some embodiments, the composition may include not more than 8 triterpenoids. In some embodiments, the composition may include not more than 7 triterpenoids. In some embodiments, the composition may include not more than 6 triterpenoids.

In some embodiments, there is provided a combination comprising at least one of MDA, IMDA, MLA, IMLA, 3-O-acetyl-masticadienolic acid, 3-O-acetyl-epimasticadienolic acid, 3-O-acetyl-isomasticadienolic acid, 3-O-acetyl-epi-isomasticadienolic acid; OA and MA; in addition to at least one of NF-1, NF-2, NF-3, NF-4, NF-A, NF-B and NF-P. Each possibility is a separate embodiment of the invention. In some embodiments, there is provided a combination comprising at least one of MDA, IMDA, MLA, IMLA, 3-O-acetyl-masticadienolic acid, 3-O-acetyl-epimasticadienolic acid, 3-O-acetyl-isomasticadienolic acid, 3-O-acetyl-epi-isomasticadienolic acid; OA and MA; in addition to at least one of NF-1, NF-2, NF-3, NF-4, NF-A and NF-B. Each possibility is a separate embodiment of the invention. In some embodiments, the combination comprises at least one of MDA, IMDA, MLA, IMLA, 3-O-acetyl-masticadienolic acid, 3-O-acetyl-isomasticadienolic acid, OA and MA; in addition to at least one of NF-1, NF-2, NF-3 and NF-4. In some embodiments, the combination comprises at least one of MDA and IMDA; in addition to at least one of (NF-1, NF-2, NF-3 and NF-4. In some embodiments, the combination comprises at least one of MDA and IMDA; in addition to at least one of NF-1, NF-2, NF-3, NF-4, NF-A, NF-B and NF-P. In some embodiments, the combination comprises at least one of MDA and IMDA; in addition to at least one of NF-1, NF-2, NF-3, NF-4, NF-A and NF-B. In some embodiments the combination may further include a pharmaceutically acceptable carrier.

In some embodiments, the composition further comprises at least one neutral triterpenoid selected from the group consisting of: 3-beta-hydroxy-13-alpha-malabarica-14(26), 17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Oleanolic aldehyde (28-oxo-beta-amyrin), 3-beta-20-dihydroxylupane, Masticadienonic aldehyde, 3-oxo-malabarica-14(26),17E,21-triene. Each possibility is a separate embodiment of the invention.

In some embodiments, the composition further comprises at least one neutral triterpenoid selected from the group consisting of: 3-beta-hydroxy-13-alpha-malabarica-14(26), 17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene. Each possibility is a separate embodiment of the invention.

In some embodiments, in a composition comprising more than one triterpenoic acid, if present in such composition, IMDA and MDA are present at a ratio of about 1:1 w/w.

In some embodiments, in a composition comprising more than one triterpenoic acid, if present in such composition, MDA, IMDA, MLA IMLA are present at a ratio of about 1:1:0.2:0.2 (5:5:1:1) w/w respectively.

In some embodiments, if present in such composition IMDA, MDA, NF-1, NF-2, NF-3 and NF-4 are present at a ratio of about 1:1:0.5:0.5:0.5:0.33 (6:6:3:3:2) w/w respectively.

In some embodiments, if present in such composition IMDA, MDA, NF-1, NF-2, NF-3, NF-4, NF-P, NF-A, and NF-B are present at a ratio of about 1:1:0.5:0.5:0.5:0.33:0.33:0.25:0.25 (12:12:6:6:4:4:3:3) w/w respectively.

In some embodiments, if present in such composition IMDA, MDA, NF-1, NF-2, NF-3, NF-4, NF-A, and NF-B are present at a ratio of about 1:1:0.5:0.5:0.5:0.33:0.25:0.25 (12:12:6:6:4:4:3:3) w/w respectively.

In some embodiments, if present in such composition, NF-1, NF-2, NF-3 and NF-4 present at a ratio of about 1:1:1:0.67 (3:3:3:2) w/w respectively.

In some embodiments, if present in such composition, NF-1, NF-2, NF-3, NF-4, NF-P, NF-A, and NF-B are present at a ratio of about 1:1:1:0.67:0.67:0.5:0.5 (6:6:6:4:4:3:3) respectively.

In some embodiments, if present in such composition, NF-1, NF-2, NF-3, NF-4, NF-A, and NF-B are present at a ratio of about 1:1:1:0.67:0.5:0.5 (6:6:6:4:3:3) respectively.

In some embodiments, the composition further comprises at least one neutral triterpenoid selected from the group consisting of: Beta-amyrone, Beta-amyrin and Germanicol. Each possibility is a separate embodiment of the invention.

In some embodiments, the combination may further comprise at least one triterpenoic acid selected from the group consisting of: oleanolic acid, ursonic acid and ursolic acid. Each possibility is a separate embodiment of the invention.

In some embodiments, the triterpenoic acid(s) may be obtained from a plant source. In some embodiments, any one of the triterpenoic acids may be obtained from a plant source. In some embodiments, at least one triterpenoic acid may be obtained from a plant source. In some embodiments, the neutral triterpenoid(s) may be obtained from a plant source. In some embodiments, any one of the neutral triterpenoids may be obtained from a plant source. In some embodiments, at least one neutral triterpenoid may be obtained from a plant source. In some embodiments, the plant source may include mastic gum.

In some embodiments, any one of the triterpenoic acids and/or the neutral triterpenoid may be isolated from a natural source or may be the product of a chemical synthesis. In some embodiments, the triterpenoic acids and/or the neutral triterpenoids may be isolated from a natural source or may be the product of a chemical synthesis.

In some embodiments, any one of the triterpenoic acids and neutral triterpenoids may be the product of a biochemical reaction or a product produced by a microbial organism. In some embodiments, any one of the triterpenoic acids and neutral triterpenoids may be the product of a fermentation process. In some embodiments, any one of the triterpenoic acids and neutral triterpenoids may be produced by a combination of a chemical synthesis and a biochemical reaction. In some embodiments, any one of the triterpenoic acids and neutral triterpenoids may be produced by a combination of a chemical synthesis and a fermentation process. In some embodiments, the any one of triterpenoic acids and neutral triterpenoids may be produced by a combination of any of the above indicated options. In case of a biochemical reaction or microbial process, the biochemical agent and the microbial agent may be a naturally occurring agent or may be a modified agent not naturally occurring. Modification of these agents may have been achieved using modern biochemical methods such as for example genetic engineering. Said biochemical agents and microbial agents not occurring naturally may also have been created using synthetic biology methods.

In some embodiments, obtaining from a natural source may include isolating from a natural source. In some embodiments, the isolation from the natural source may include isolation as individual compound(s) or as a group(s) of compounds. In some embodiments, the natural source may include a plant material selected from the group consisting of a resin, a gum, leaves, twigs, roots, flowers, seeds, buds, bark, nuts and roots. Each possibility is a separate embodiment. In some embodiments, the natural source may include a resin extracted from at least one plant. In some embodiments, the natural source may include mastic gum.

In some embodiments, the natural source may include at least one plant. In some embodiments, the plant may be classified in the family Anacardiaceae. In some embodiments, the plant may comprise at least one plant classified in the genus/genera *Pistacia* and/or *Schinus*. In some embodiments, *Pistacia* may include species selected from the group consisting of *P. lentiscus, P. atlantica, P. palestina, P. saportae, P. terebinthus, P. vera P. integerrima*, and *P. lentiscus* L. Each possibility is a separate embodiment. In some embodiments, *Pistacia* may include the species *Pistacia lentiscus* L. In some embodiments, *Schinus* may include the species *S. molle*. In some embodiments, the *Pistacia* may include the species *Pistacia Lentiscus* var. *Chia*. In some embodiments, the *Pistacia* may include the species *Pistacia lentiscus* L. var. *latifolius* Coss. Each possibility is a separate embodiment of the invention.

In some embodiments, the triterpenoids may be obtained by a process comprising one or more of the steps of:
(a) treating mastic gum with a polar organic solvent;
(b) isolating a fraction soluble in said polar organic solvent;
(c) optionally removing said polar organic solvent;
(d) treating the soluble fraction obtained in step (b) or (c) with a non-polar organic solvent;
(e) isolating a fraction soluble in said non-polar organic solvent;
(f) optionally removing said non-polar organic solvent;
(g) dissolving the fraction obtained in step (f) in a first organic solvent;
(h) treatment of the solution obtained in step (g) or (e) with a basic aqueous solution so as to obtain a basic aqueous fraction containing triterpenoic acids in a deprotonated salt form and an intermediate oily or emulsion phase in addition to the first organic solution containing neutral triterpenoids;
(i) separating said basic aqueous fraction and the intermediate oily/emulsion phase from the first organic solution
(j) acidifying the basic aqueous fraction and emulsion obtained in step (i) with an acid;
(k) extracting the acidified fraction obtained in step (j) with a second organic solvent;
(l) optionally contacting the organic fraction obtained in step (k) with a drying agent;
(m) removing the second organic solvent, the drying agent and/or excess acid from the fraction obtained in any of steps (j), (k) or (l) thus providing an isolated acidic fraction;
(n) taking the first organic solution from step (i), optionally contacting it with a drying agent; and
(o) removing the first organic solvent and the drying agent thus providing an isolated neutral fraction.

The individual triterpenoic acids can be obtained by chromatographic separation from the isolated acidic fraction obtained in step (m). The individual neutral triterpenoids can be obtained by chromatographic separation from the isolated neutral fraction obtained in step (o).

The individually obtained triterpenoic acids and neutral triterpenoids may then be mixed or combined as required in order to obtain the desired pharmaceutical compositions.

In some embodiments, the current invention provides a pharmaceutical composition consisting essentially of MDA, IMDA, NF-1, NF-2, NF-3 and NF-4 as the pharmaceutically active ingredients; and a pharmaceutically acceptable carrier. In some embodiments, the current invention provides a pharmaceutical composition consisting essentially of MDA, IMDA, MLA, IMLA, NF-1, NF-2, NF-3, NF-4, NF-A, NF-B and NF-P as the pharmaceutically active ingredients; and a pharmaceutically acceptable carrier. In some embodiments, the current invention provides a pharmaceutical composition consisting essentially of MDA, IMDA, MLA, IMLA, NF-1, NF-2, NF-3, NF-4, NF-A and NF-B as the pharmaceutically active ingredients; and a pharmaceutically acceptable carrier. In some embodiments, the current invention provides a pharmaceutical composition consisting essentially of MDA, IMDA, NF-1, NF-2, NF-3, NF-4, NF-A, NF-B and NF-P as the pharmaceutically active ingredients; and a pharmaceutically acceptable carrier. In some embodiments, the current invention provides a pharmaceutical composition consisting essentially of MDA, IMDA, NF-1, NF-2, NF-3, NF-4, NF-A and NF-B as the pharmaceutically active ingredients; and a pharmaceutically acceptable carrier. In some embodiments, the current invention provides a pharmaceutical composition consisting essentially of MA, OA, MDA, IMDA 3-O-acetyl-masticadienolic acid, 3-O-acetyl-isomasticadienolic acid, MLA, IMLA, NF-1, NF-2, NF-3 and NF-4 as the pharmaceutically active ingredients; and a pharmaceutically acceptable carrier. In some embodiments, the current invention provides a pharmaceutical composition consisting essentially of MA, OA, MDA, IMDA 3-O-acetyl-masticadienolic acid, 3-O-acetyl-isomasticadienolic acid, MLA, IMLA, NF-1, NF-2, NF-3, NF-4, NF-A, NF-B and NF-P as the pharmaceutically active ingredients; and a pharmaceutically acceptable carrier. In some embodiments, the current invention provides a pharmaceutical composition consisting essentially of MA, OA, MDA, IMDA, 3-O-acetyl-masticadienolic acid, 3-O-acetyl-isomasticadienolic acid, MLA, IMLA, NF-1, NF-2, NF-3, NF-4, NF-A and NF-B as the pharmaceutically active ingredients; and a pharmaceutically acceptable carrier.

Any one of the triterpenoic acids and/or the neutral triterpenoids may be isolated from a natural source such as mastic gum, or may be the product of a chemical synthesis.

In some embodiments, any one of MDA, IMDA, MLA, IMLA, 3-O-acetyl-masticadienolic acid, 3-O-acetyl-epimasticadienolic acid, 3-O-acetyl-isomasticadienolic acid, 3-O-acetyl-epi-isomasticadienolic acid, OA, MA, NF-1, NF-2, NF-3, NF-4, NF-A, NF-B), and NF-P may be a product of a chemical synthesis. In some embodiments, any one of the at least one triterpenoic acid and the at least one neutral triterpenoid may be a product of a chemical synthesis.

In some embodiments, any one of MDA, IMDA, MLA, IMLA, 3-O-acetyl-masticadienolic acid, 3-O-acetyl-epimasticadienolic acid, 3-O-acetyl-isomasticadienolic acid, 3-O-acetyl-epi-isomasticadienolic acid, OA, MA, NF-1, NF-2, NF-3, NF-4, NF-A and NF-B may be a product of a chemical synthesis. In some embodiments, any one of the at least one triterpenoic acid and the at least one neutral triterpenoid may be a product of a chemical synthesis.

Plant species useful for obtaining the compositions of the invention include without limitation, those of the genus *Pistacia*. Useful species of *Pistacia* include without limitation, *P. lentiscus, P. atlantica, P. palestina, P. saportae, P. terebinthus, P. vera* and *P. integerrima*. In some embodiments, the plant species useful for obtaining the compositions of the invention is *Pistacia lentiscus*. In some embodiments, the plant species useful for obtaining the compositions of the invention is *Pistacia vera*. In some embodiments, the species useful for obtaining the compositions of the invention is *Pistacia palestina*. In some embodiments, the species useful for obtaining the compositions of the invention is *Pistacia atlantica*. In some embodiments, the species useful for obtaining the compositions of the invention is *Pistacia terebinthus*. In some embodiments, the species useful for obtaining the compositions of the invention is *Pistacia saportae*. Each possibility is a separate embodiment of the invention.

Analytical methods for determining the precise chemical structure of the triterpenoic acids and neutral triterpenoids include nuclear magnetic resonance (for example $^{1}$H-NMR and $^{13}$C-NMR), various mass spectrometry methods (for example MALDI-TOF), HPLC, combination methods such as Liquid Chromatography-Mass spectrometry (LC-MS; LC-MS/MS, UV-VIS spectrometry, IR and FT-IR spectrometry and other methods as known in the art.

In some embodiments, the composition includes at least one triterpenoic acid and at least one neutral triterpenoid. In some embodiments, the at least one triterpenoic acid may include masticadienonic acid (MDA), isomasticadienonic acid (IMDA), masticadienolic acid (MLA), isomasticadienolic acid (IMLA), 3-O-acetyl-masticadienolic acid, 3-O-acetyl-epimasticadienolic acid, 3-O-acetyl-isomasticadienolic acid, 3-O-acetyl-epi-isomasticadienolic acid, oleanonic acid (OA), moronic acid (MA), or any combination thereof. In some embodiments, the neutral triterpenoid may include 8-dihydroxypolypoda-13E,17E,21-triene (NF-1), (8R)-3-Oxo-8-hydroxypolypoda-13E,17E,21-triene (NF-2), Oleanonic aldehyde (NF-3), Tirucallol (NF-4), 28-hydroxylup-20(29)-en-3-one (NF-A), 28-hydroxy-beta-amyrone (NF-B), 20-hydroxydammar-24-en-3-one (NF-P) or any combination thereof.

In some embodiments, the composition includes at least one triterpenoic acid and at least one neutral triterpenoid. In some embodiments, the at least one triterpenoic acid may include masticadienonic acid (MDA), isomasticadienonic acid (IMDA), masticadienolic acid (MLA), isomasticadienolic acid (IMLA), 3-O-acetyl-masticadienolic acid, 3-O-acetyl-epimasticadienolic acid, 3-O-acetyl-isomasticadienolic acid, 3-O-acetyl-epi-isomasticadienolic acid, oleanonic acid (OA), moronic acid (MA or MO), or any combination thereof. In some embodiments, the neutral triterpenoid may include 8-dihydroxypolypoda-13E,17E,21-triene (NF-1), (8R)-3-Oxo-8-hydroxypolypoda-13E,17E,21-triene (NF-2), Oleanonic aldehyde (NF-3), Tirucallol (NF-4), 28-hydroxylup-20(29)-en-3-one (NF-A), 28-hydroxy-beta-amyrone (NF-B) or any combination thereof.

In some embodiments, the triterpenoic acid may include at least masticadienonic acid (MDA). In some embodiments, the triterpenoic acid may at least include isomasticadienonic acid (IMDA). In some embodiments, the triterpenoic acid may include at least masticadienonic acid (MDA) and isomasticadienonic acid (IMDA). In some embodiments, the triterpenoic acid may include at least masticadienonic acid (MDA), isomasticadienonic acid (IMDA), masticadienolic acid (MLA) and isomasticadienolic acid (IMLA). In some embodiments, neutral triterpenoid may include at least NF-1 and NF-2. In some embodiments, the neutral triterpenoid may include at least NF-1, NF-2, NF-3 and NF-4. In some embodiments, the neutral triterpenoid may include at least NF-1, NF-2, NF-3, NF-4, NF-A, NF-B and NF-P.

In some embodiments, the triterpenoic acid may include at least masticadienonic acid (MDA) and isomasticadienonic acid (IMDA). In some embodiments, the triterpenoic acid may include at least masticadienonic acid (MDA), isomasticadienonic acid (IMDA), masticadienolic acid (MLA) and isomasticadienolic acid (IMLA). In some embodiments, neutral triterpenoid may include at least NF-1 and NF-2. In some embodiments, the neutral triterpenoid may include at least NF-1, NF-2, NF-3 and NF-4. In some embodiments, the neutral triterpenoid may include at least NF-1, NF-2, NF-3, NF-4, NF-A and NF-B.

In some embodiments, the neutral triterpenoids consist essentially of not more than seven neutral triterpenoids. In some embodiments, the neutral triterpenoids consist essentially of not more than six neutral triterpenoids. In some embodiments, the neutral triterpenoids consist essentially of not more than five neutral triterpenoids. In some embodiments, the neutral triterpenoids consist essentially of not more than four neutral triterpenoids.

In some embodiments, the additional neutral triterpenoids consist essentially of not more than six neutral triterpenoids. In some embodiments, the additional neutral triterpenoids consist essentially of not more than five neutral triterpenoids. In some embodiments, the additional neutral triterpenoids consist essentially of not more than four neutral triterpenoids. In some embodiments, the additional neutral triterpenoids consist essentially of not more than three neutral triterpenoids. In some embodiments, the additional neutral triterpenoids consist essentially of not more than two neutral triterpenoids. In some embodiments, the additional neutral triterpenoid consists essentially of one neutral triterpenoid.

In some embodiments, the triterpenoic acids consists essentially of not more than eight triterpenoic acids. In some embodiments, the triterpenoic acids consists essentially of not more than seven triterpenoic acids. In some embodiments, the triterpenoic acids consists essentially of not more than six triterpenoic acids. In some embodiments, the triterpenoic acids consists essentially of not more than five triterpenoic acids. In some embodiments, the triterpenoic acids consists essentially of not more than four triterpenoic acids. In some embodiments, the triterpenoic acids consists essentially of not more than three triterpenoic acids. In some embodiments, the triterpenoic acids consists essentially of not more than two triterpenoic acids. In some embodiments, the triterpenoic acid consists essentially of one triterpenoic acid.

In some embodiments, the composition consists essentially of not more than 15 triterpenoids. In some embodiments, the composition consists essentially of not more than 14 triterpenoids. In some embodiments, the composition consists essentially of not more than 13 triterpenoids. In some embodiments, the composition consists essentially of not more than 12 triterpenoids. In some embodiments, the composition consists essentially of not more than 11 triterpenoids. In some embodiments, the composition consists essentially of not more than 10 triterpenoids. In some embodiments, the composition consists essentially of not more than 9 triterpenoids. In some embodiments, the composition consists essentially of not more than 8 triterpenoids. In some embodiments, the composition consists essentially of not more than 7 triterpenoids. In some embodiments, the composition consists essentially of not more than 6 triterpenoids. Such compositions unexpectedly exhibit a synergistic effect, whereby the combination of compounds exhibit a markedly improved therapeutic effect in the treatment of optic neuropathy condition.

In some embodiments, the composition comprises at least one triterpenoic acid selected from MDA, IMDA, MLA, IMLA, OA, MA, 3-O-acetyl-masticadienolic acid, 3-O-acetyl-epimasticadienolic acid, 3-O-acetyl-isomasticadienolic acid and 3-O-acetyl-epi-isomasticadienolic acid. In some embodiments, the composition comprises at least one triterpenoic acid selected from MDA, IMDA, MLA, IMLA, OA, MA, 3-O-acetyl-masticadienolic acid and 3-O-acetyl-isomasticadienolic acid. In some embodiments, the composition comprises at least one triterpenoic acid selected from MDA, IMDA, MLA and IMLA. In some embodiments, the composition comprises at least one triterpenoic acid selected from MDA, IMDA, and MLA. In some embodiments, the composition comprises at least one triterpenoic acid selected from MDA, IMDA and IMLA. In some embodiments, the composition comprises at least MDA and IMDA. In some embodiments, the composition comprises at least MDA. In some embodiments, the composition comprises at least IMDA. In some embodiments, the composition comprises at least 3-O-acetyl-masticadienolic acid. In some embodiments, the composition comprises at least 3-O-acetyl-isomasticadienolic acid. In some embodiments, the composition comprises at least 3-O-acetyl-epimasticadienolic acid. In some embodiments, the composition comprises at least 3-O-acetyl-epi-isomasticadienolic acid.

In some embodiments, the composition comprises at least two triterpenoic acids selected from MDA, IMDA, MLA, IMLA, OA, MA, 3-O-acetyl-masticadienolic acid, 3-O-acetyl-epimasticadienolic acid, 3-O-acetyl-isomasticadienolic acid and 3-O-acetyl-epi-isomasticadienolic acid. In some embodiments, the composition comprises at least two triterpenoic acids selected from MDA, IMDA, MLA, IMLA, OA, MA, 3-O-acetyl-masticadienolic acid and 3-O-acetyl-isomasticadienolic acid. In some embodiments, the composition comprises at least two triterpenoic acids selected from MDA, IMDA, MLA and IMLA. In some embodiments, the composition comprises at least two triterpenoic acids selected from MDA, IMDA, and MLA. In some embodiments, the composition comprises at least two triterpenoic acids selected from MDA, IMDA and IMLA. In some embodiments, the composition comprises at least MDA and IMDA.

In some embodiments, the composition comprises at least three triterpenoic acids selected from MDA, IMDA, MLA, IMLA, OA, MA, 3-O-acetyl-masticadienolic acid, 3-O-acetyl-epimasticadienolic acid, 3-O-acetyl-isomasticadienolic acid and 3-O-acetyl-epi-isomasticadienolic acid. In some embodiments, the composition comprises at least three triterpenoic acids selected from MDA, IMDA, MLA, IMLA, OA, MA, 3-O-acetyl-masticadienolic acid and 3-O-acetyl-isomasticadienolic acid. In some embodiments, the composition comprises at least three triterpenoic acids selected from MDA, IMDA, MLA and IMLA. In some embodiments, the composition comprises at least MDA, IMDA, and MLA. In some embodiments, the composition comprises at least MDA, IMDA and IMLA.

In some embodiments, the composition comprises at least four triterpenoic acids selected from MDA, IMDA, MLA, IMLA, OA, MA, 3-O-acetyl-masticadienolic acid, 3-O-acetyl-epimasticadienolic acid, 3-O-acetyl-isomasticadienolic acid and 3-O-acetyl-epi-isomasticadienolic acid. In some embodiments, the composition comprises at least four triterpenoic acids selected from MDA, IMDA, MLA, IMLA, OA, MA, 3-O-acetyl-masticadienolic acid and 3-O-acetyl-isomasticadienolic acid. In some embodiments, the composition comprises at least MDA, IMDA, MLA and IMLA.

In some embodiments, the composition comprises at least one neutral triterpenoid selected from NF-1, NF-2, NF-3, NF-4, NF-A, NF-B, NF-P, 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and Germanicol. In some embodiments, the composition comprises at least one neutral triterpenoid selected from NF-1, NF-2, NF-3, NF-4, NF-A, NF-B, 3-beta-hydroxy-13-alpha-malabarica-14(26), 17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and Germanicol. Each possibility is a separate embodiment. In some embodiments, the composition comprises at least one neutral triterpenoid selected from NF-1, NF-2, NF-3, NF-4, NF-A, NF-B and NF-P. In some embodiments, the composition comprises at least one neutral triterpenoid selected from NF-1, NF-2, NF-3, NF-4, NF-A and NF-B. In some embodiments, the composition comprises at least one neutral triterpenoid selected from NF-1, NF-2, NF-3 and NF-4. In some embodiments, the composition comprises at least one neutral triterpenoid selected from NF-1, NF-2 and NF-3. In some embodiments, the composition comprises at least one neutral triterpenoid selected from NF-1, NF-2 and NF-4. In some embodiments, the composition comprises at least one neutral triterpenoid selected from NF-1 and NF-2. In some embodiments, the composition comprises at least NF-1. In some embodiments, the composition comprises at least NF-2. In some embodiments, the composition comprises at least NF-3. In some embodiments, the composition comprises at least NF-4.

In some embodiments, the composition comprises at least two neutral triterpenoids selected from NF-1, NF-2, NF-3, NF-4, NF-A, NF-B, NF-P, 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and Germanicol. In some embodiments, the composition comprises at least two neutral triterpenoids selected from NF-1, NF-2, NF-3, NF-4, NF-A, NF-B, 3-beta-hydroxy-13-alpha-malabarica-14(26), 17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and Germanicol. Each possibility is a separate embodiment. In some embodiments, the composition comprises at least two neutral triterpenoids selected from NF-1, NF-2, NF-3, NF-4, NF-A, NF-B and NF-P. In some embodiments, the composition comprises at least two neutral triterpenoids selected from NF-1, NF-2, NF-3, NF-4, NF-A and NF-B. In some embodiments, the composition comprises at least two neutral triterpenoids selected from NF-1, NF-2, NF-3 and NF-4. In some embodiments, the composition comprises at least two neutral triterpenoids selected from NF-1, NF-2 and NF-3. In some embodiments, the composition comprises at least two neutral triterpenoids selected from NF-1, NF-2 and NF-4. In some embodiments, the composition comprises at least NF-1 and NF-2.

In some embodiments, the composition comprises at least three neutral triterpenoids selected from NF-1, NF-2, NF-3, NF-4, NF-A, NF-B, NF-P, 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and Germanicol. In some embodiments, the composition comprises at least three neutral triterpenoids selected from NF-1, NF-2, NF-3, NF-4, NF-A, NF-B, 3-beta-hydroxy-13-alpha-malabarica-14(26), 17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and Germanicol. Each possibility is a separate embodiment. In some embodiments, the composition comprises at least three neutral triterpenoids selected from NF-1, NF-2, NF-3, NF-4, NF-A, NF-B and NF-P. In some embodiments, the composition comprises at least three neutral triterpenoids selected from NF-1, NF-2, NF-3, NF-4, NF-A and NF-B. In some embodiments, the composition comprises at least three neutral triterpenoids selected from NF-1, NF-2, NF-3 and NF-4. In some embodiments, the composition comprises at least NF-1, NF-2 and NF-3. In some embodiments, the composition comprises at least NF-1, NF-2 and NF-4. In some embodiments, the composition comprises at least NF-1, NF-3 and NF-4. In some embodiments, the composition comprises at least NF-3, NF-3 and NF-4.

In some embodiments, the composition comprises at least four neutral triterpenoids selected from NF-1, NF-2, NF-3, NF-4, NF-A, NF-B, NF-P, 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and Germanicol. Each possibility is a separate embodiment. In some embodiments, the composition comprises at least four neutral triterpenoids selected from NF-1, NF-2, NF-3, NF-4, NF-A, NF-B, 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and Germanicol. Each possibility is a separate embodiment. In some embodiments, the composition comprises at least four neutral triterpenoids selected from NF-1, NF-2, NF-3, NF-4, NF-A and NF-B. In some embodiments, the composition comprises at least four neutral triterpenoids selected from NF-1, NF-2, NF-3, NF-4, NF-A, NF-B and NF-P. In some embodiments, the composition comprises at least NF-1, NF-2, NF-3 and NF-4.

In some embodiments, combinations of triterpenoic acids and neutral triterpenoids may be substantially devoid of essential oils.

In some embodiments, the triterpenoic acids may comprise from about 1% to about 80% of the total active ingredients of the composition. In some embodiments, the triterpenoic acids may comprise up to 99% of the total active ingredients of the composition. In some embodiments, the triterpenoic acids may comprise from about 10% to about 80% of the total active ingredients of the composition. In some embodiments, the triterpenoic acids may comprise from about 20% to about 80% of the total active ingredients of the composition. In some embodiments, the triterpenoic acids may comprise from about 30% to about 70% of the total active ingredients of the composition. In some embodiments, the triterpenoic acids may comprise from about 35% to about 65% of the total active ingredients of the composition. In some embodiments, the triterpenoic acids may comprise from about 40% to about 60% of the total active ingredients of the composition.

In some embodiments, the triterpenoic acids may comprise from about 0.01% to about 80% of the total composition. In some embodiments, the triterpenoic acids may comprise from about 0.01% to about 50% of the total composition. In some embodiments, the triterpenoic acids may comprise from about 0.01% to about 10% of the total composition. In some embodiments, the triterpenoic acids may comprise from about 0.1% to about 10% of the total composition. In some embodiments, the triterpenoic acids may comprise from about 0.5% to about 4% of the total composition. In some embodiments, the triterpenoic acids may comprise from about 0.1% to about 0.5% of the total composition. In some embodiments, the triterpenoic acids may comprise from about 0.1% to about 1.0% of the total composition. In some embodiments, the triterpenoic acids may comprise from about 0.1% to about 2% of the total composition. In some embodiments, the triterpenoic acids may comprise from about 1% to about 3.5% of the total composition. In some embodiments, the triterpenoic acids may comprise from about 1.5% to about 3% of the total composition. In some embodiments, the triterpenoic acids may comprise from about 1.75% to about 2.75% of the total composition. In some embodiments, the triterpenoic acids may comprise from about 2% to about 2.5% of the total composition.

In some embodiments, the neutral triterpenoids may comprise from about 1% to about 80% of the total active ingredients of the composition. In some embodiments, the neutral triterpenoids may comprise up to 99% of the total active ingredients of the composition. In some embodiments, the neutral triterpenoids may comprise from about 10% to about 80% of the total active ingredients of the composition. In some embodiments, the neutral triterpenoids may comprise from about 20% to about 80% of the total active ingredients of the composition. In some embodiments, the neutral triterpenoids may comprise from about 30% to about 70% of the total active ingredients of the composition. In some embodiments, the neutral triterpenoids may comprise from about 35% to about 65% of the total active ingredients of the composition. In some embodiments, the neutral triterpenoids may comprise from about 40% to about 60% of the total active ingredients of the composition.

In some embodiments, the neutral triterpenoids may comprise from about 0.01% to about 80% of the total composition. In some embodiments, the neutral triterpenoids may comprise from about 0.01% to about 50% of the total composition. In some embodiments, the neutral triterpenoids may comprise from about 0.01% to about 10% of the total composition. In some embodiments, the neutral triterpenoids may comprise from about 0.1% to about 10% of the total composition. In some embodiments, the neutral triterpenoids may comprise from about 0.5% to about 4% of the total composition. In some embodiments, the neutral triterpenoid may comprise from about 0.1% to about 0.5% of the total composition. In some embodiments, the neutral triterpenoid may comprise from about 0.1% to about 1.0% of the total composition. In some embodiments, the neutral triterpenoid may comprise from about 0.1% to about 2% of the total composition. In some embodiments, the neutral triterpenoids may comprise from about 1% to about 3.5% of the total composition. In some embodiments, the neutral triterpenoids may comprise from about 1.5% to about 3% of the total composition. In some embodiments, the neutral triterpenoids may comprise from about 1.75% to about 2.75% of the total composition. In some embodiments, the neutral triterpenoids may comprise from about 2% to about 2.5% of the total composition.

In some embodiments, the triterpenoic acid portion in a combination of triterpenoic acids with neutral triterpenoids may include as the main compounds one or more of: Moronic acid, Oleanonic acid, 24-Z-Masticadienonic acid, 24-Z-Isomasticadienonic acid, 3-beta-24-Z-O-acetyl-masticadienolic acid, and/or 3-beta-24-Z-O-acetyl-isomasticadienolic acid. Each possibility is a separate embodiment.

In some embodiments, the triterpenoic acid portion in a combination of triterpenoic acids with neutral triterpenoids may include as the main compounds: Moronic acid (12-15%), Oleanonic acid (18-20%), 24-Z-Masticadienonic acid (20-22%), 24-Z-Isomasticadienonic acid (22-26%), 3-beta-24-Z-O-acetyl-masticadienolic acid (4-7%), and/or 3-beta-24-Z-O-acetyl-isomasticadienolic acid (4-7%). Each possibility is a separate embodiment.

In some embodiments, this triterpenoic acid portion may further include (in addition to the main compounds) additional other triterpenoic acids in small amounts, typically less than 5%. Such additional possible other triterpenoic acids may be selected from one or more of: MLA: 3-beta-masticadienolic acid, IMLA: 3-beta-isomasticadienolic acid, 3-beta-O-acetyl-epimasticadienolic acid, 3-beta-O-acetyl-epi-isomasticadienolic acid, Epimasticadienolic acid (3-alpha-masticadienolic acid), Epi-isomasticadienolic acid (3-alpha-isomasticadienolic acid), Dihydromasticadienonic acid and/or Dihydroisomasticadienonic acid. Each possibility is a separate embodiment.

In some embodiments, the neutral triterpenoid portion of a combination with triterpenoic acids may include as the main compounds one or more of: NF-1 ((8R)-3-beta, 8-dihydroxypolypoda-13E,17E,21-triene), NF-2 ((8R)-3-Oxo-8-hydroxypolypoda-13E,17E,21-triene), NF-3 (Oleanonic aldehyde), NF-4 (Tirucallol), NF-P (Dipterocarpol (20-hydroxydammar-24-en-3-one)), NF-A ((Betulon), 28-hydroxylup-20(29)-en-3-one), NF-B (Oleanonic alcohol; (28-hydroxy-beta-amyrone)), 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and/or Germanicol. Each possibility is a separate embodiment.

In some embodiments, the triterpenoic acids in an isolated acidic fraction of mastic gum may include as the main compounds one or more of: Moronic acid, Oleanonic acid, 24-Z-Masticadienonic acid, 24-Z-Isomasticadienonic acid, 3-beta-OAc-24-Z-masticadienolic acid, and/or 3-beta-OAc-24-Z-isomasticadienolic acid. Each possibility is a separate embodiment.

In some embodiments, the triterpenoic acids in an isolated acidic fraction of mastic gum may include as the main compounds: Moronic acid (12-15%), Oleanonic acid (18-20%), 24-Z-Masticadienonic acid (20-22%), 24-Z-Isomasticadienonic acid (22-26%), 3-beta-OAc-24-Z-masticadienolic acid (4-7%), and/or 3-beta-OAc-24-Z-isomasticadienolic acid (4-7%). Each possibility is a separate embodiment.

In some embodiments, these triterpenoic acids in an isolated acidic fraction of mastic gum may further include (in addition to the main compounds) additional other triterpenoic acids in small amounts, typically less than 5%. Such additional possible other triterpenoic acids may be selected from one or more of: MLA: 3-beta-masticadienolic acid, IMLA: 3-beta-isomasticadienolic acid, 3-beta-OAc-epimasticadienolic acid, 3-beta-OAc-epi-isomasticadienolic acid, Epimasticadienolic acid (3-alpha-masticadienolic acid), Epi-isomasticadienolic acid (3-alpha-isomasticadienolic acid), Dihydromasticadienonic acid and/or Dihydroisomasticadienonic acid. Each possibility is a separate embodiment.

In some embodiments, the neutral triterpenoids in an isolated neutral fraction of mastic gum may include as the main compounds one or more of: NF-1 ((8R)-3-beta, 8-dihydroxypolypoda-13E,17E,21-triene), NF-2 ((8R)-3-Oxo-8-hydroxypolypoda-13E,17E,21-triene), NF-3 (Oleanonic aldehyde), NF-4 (Tirucallol), NF-P (Dipterocarpol (20-hydroxydammar-24-en-3-one)), NF-A ((Betulon), 28-hydroxylup-20(29)-en-3-one), NF-B (Oleanonic alcohol; (28-hydroxy-beta-amyrone)), 3-beta-hydroxy-13-alpha-malabarica-14(26),17E,21-triene, 20-hydroxy-lupan-3-one, 28-Nor-17-hydroxylupen-3-one, 28-oxo-lupen-3-one, 28-nor-beta-amyrone, Isomasticadienonic aldehyde, Isomasticadienediol, Masticadienediol, Oleanolic aldehyde (28-oxo-beta-amyrin), 3-beta-20-dihydroxylupane, Masticadienonic aldehyde, 3-oxo-malabarica-14(26),17E,21-triene, Beta-amyrone, Beta-amyrin and/or Germanicol. Each possibility is a separate embodiment.

It is understood that when the combinations and/or isolated fractions of mastic gum are mentioned in any paragraph concern either only triterpenoic acids or only neutral triterpenoids, the intended use of such combinations and/or isolated fractions is in accordance with the invention; meaning the use of at least one triterpenoic acid together with at least one neutral triterpenoid.

In some embodiments, the composition for use in the invention comprises a therapeutically effective amount of at least one triterpenoic acid and of at least one neutral triterpenoid as described herein, and a pharmaceutically acceptable carrier. In some embodiments, the carrier is hydrophobic.

In some embodiments, the pharmaceutically acceptable carrier may include a hydrophobic carrier. In some embodiments, the hydrophobic carrier may include at least one oil. In some embodiments, the oil may be selected from the group consisting of a mineral oil, a vegetable oil and combinations thereof. In some embodiments, the vegetable oil may be selected from the group consisting of cottonseed oil, olive oil, almond oil, canola oil, coconut oil, corn oil, grape seed oil, peanut oil, saffron oil, sesame oil, soybean oil, and combinations thereof. In some embodiments, the vegetable oil is a commercially available product, which may be obtained either as a 'NF' (National Formulary) grade product or as a 'USP' (US Pharmacopoeia) grade product. In some embodiments, the mineral oil may be light mineral oil. In some embodiments, the hydrophobic carrier may include at least one wax. In some embodiments, the hydrophobic carrier may include a combination of at least one oil and at least one wax.

The term "mineral oil" refers to a clear colorless nearly odorless and tasteless liquid obtained from the distillation of petroleum. It may also be referred to as white oil, white mineral oil, liquid petrolatum, liquid paraffin or white paraffin oil. In some embodiments, the mineral oil is light mineral oil, a commercially available product which may be obtained either as a 'NF' (National Formulary) grade product or as a 'USP' (US Pharmacopoeia) grade product. For use in the invention, the mineral oil is preferably free of aromatics and other unsaturated compounds.

The pharmaceutically acceptable carrier may alternately or additionally comprise an oil replacement. Oil replacements include alkanes having at least 10 carbon atoms (e.g., isohexadecane), benzoate esters, aliphatic esters, noncomodogenic esters, volatile silicone compounds (e.g., cyclomethicone), and volatile silicone substitutes. Examples of benzoate esters include $C_{12}$-$C_{15}$ alkyl benzoate, isostearyl benzoate, 2-ethyl hexyl benzoate, dipropylene glycol benzoate, octyldodecyl benzoate, stearyl benzoate, and behenyl benzoate. Examples of aliphatic esters include $C_{12}$-$C_{15}$ alkyl octanoate and dioctyl maleate. Examples of noncomodogenic esters include isononyl isononanoate, isodecyl isononanoate, diisostearyl dimer dilinoleate, arachidyl propionate, and isotridecyl isononanoate.

The hydrophobic carrier may further comprise at least one wax. Waxes include for example, beeswax; vegetable waxes, sugar cane waxes, mineral waxes, and synthetic waxes. Vegetable waxes include for example, carnauba, candelilla, ouricury and jojoba wax. Mineral waxes include for example, paraffin wax, lignite wax, microcrystalline waxes and ozokerites. Synthetic waxes include for example, polyethylene waxes.

Various formulations of the different combinations of triterpenoic acids and neutral triterpenoids and preparation thereof are disclosed herein. The pharmaceutical compositions of the invention may be administered by any means that achieve their intended purpose. For example, administration may be by, for example, oral, parenteral, topical, transdermal routes, such as, for example, subcutaneous, intravenous, intramuscular, intradermal, intraperitoneal, intraarterial, intrauterine, intraurethral, intracardial, intracerebral, intracerebroventricular, intrarenal, intrahepatic, intratendon, intraosseous, intrathecal, dermal, vaginal, rectal, inhalation, intranasal, ocular, auricular and buccal administration routes.

The administering may in addition comprise a technique or means such as electroporation, or sonication in order to assist in their delivery, for example transdermally. Other techniques which may be employed include for example, radio frequency or pressurized spray application.

The dosage administered may be dependent upon the age, health, and weight of the subject, the use of concurrent treatment, if any, frequency of treatment, and the nature of the effect desired. The amount of triterpenoids of the present invention in any unit dosage form comprises a therapeutically effective amount which may vary depending on the recipient subject, route and frequency of administration.

In some embodiments, when MA is one of the ingredients in the composition, the amount of the MA of the total composition may be in the range of about 0% to about 25%. In some embodiments, when MA is one of the ingredients in the composition, the amount of the MA of the total composition may be in the range of about 0% to about 15%. In some embodiments, the amount of the MA of the total composition may be in the range of about 0% to about 7.5%. In some embodiments, the amount of the MA of the total composition may be in the range of about 0% to about 2.5%. In some embodiments, the amount of the MA of the total composition may be in the range of about 0% to about 1%. In some embodiments, the amount of the MA of the total composition may be in the range of about 0% to about 0.3%. In some embodiments, the amount of the MA of the total composition may about 0.3%. In some embodiments, the amount of the MA of the total amount of triterpenoids may be in the range of about 0% to about 50%. In some embodiments, the amount of the MA of the total amount of triterpenoids may be in the range of about 0% to about 25%. In some embodiments, the amount of the MA of the total amount of triterpenoids may be in the range of about 0% to about 8%. In some embodiments, the amount of the MA of the total amount of triterpenoids may be in the range of about 6% to about 8%.

In some embodiments, when OA is one of the ingredients in the composition the amount of the OA of the total composition may be in the range of about 0% to about 50%. In some embodiments, when OA is one of the ingredients in the composition the amount of the OA of the total composition may be in the range of about 0% to about 25%. In some embodiments, the amount of the OA of the total composition may be in the range of about 0% to about 10%. In some embodiments, the amount of the OA of the total composition may be in the range of about 0% to about 5%. In some embodiments, the amount of the OA of the total composition may be in the range of about 0% to about 1%. In some embodiments, the amount of the OA of the total composition may be in the range of about 0% to about 0.5%. In some embodiments, the amount of the OA of the total composition may about 0.5%. In some embodiments, the amount of the OA of the total amount of triterpenoids may be in the range of about 0% to about 50%. In some embodiments, the amount of the OA of the total amount of triterpenoids may be in the range of about 0% to about 25%. In some embodiments, the amount of the OA of the total amount of triterpenoids may be in the range of about 0% to about 11%. In some embodiments, the amount of the OA of the total amount of triterpenoids may be in the range of about 9% to about 11%.

In some embodiments, when MDA is one of the ingredients in the composition the amount of the MDA of the total composition may be in the range of about 0% to about 99%. In some embodiments, when MDA is one of the ingredients in the composition the amount of the MDA of the total composition may be in the range of about 0% to about 75%. In some embodiments, when MDA is one of the ingredients in the composition the amount of the MDA of the total composition may be in the range of about 0% to about 50%. In some embodiments, when MDA is one of the ingredients in the composition the amount of the MDA of the total composition may be in the range of about 0% to about 25%. In some embodiments, the amount of the MDA of the total composition may be in the range of about 0% to about 10%. In some embodiments, the amount of the MDA of the total composition may be in the range of about 0% to about 5%. In some embodiments, the amount of the MDA of the total composition may be in the range of about 0% to about 2.5%. In some embodiments, the amount of the MDA of the total composition may be in the range of about 0.5% to about 1%. In some embodiments, the amount of the MDA of the total amount of triterpenoids may be in the range of about 0% to about 50%. In some embodiments, the amount of the MDA of the total amount of triterpenoids may be in the range of about 5% to about 35%. In some embodiments, the amount of the MDA of the total amount of triterpenoids may be in the range of about 10% to about 26%. In some embodiments, the amount of the MDA of the total amount of triterpenoids may be in the range of about 20% to about 26%.

In some embodiments, when IMDA is one of the ingredients in the composition the amount of the IMDA of the total composition may be in the range of about 0% to about 99%. In some embodiments, when IMDA is one of the ingredients in the composition the amount of the IMDA of the total composition may be in the range of about 0% to about 75%. In some embodiments, when IMDA is one of the ingredients in the composition the amount of the IMDA of the total composition may be in the range of about 0% to about 50%. In some embodiments, when IMDA is one of the ingredients in the composition, the amount of the IMDA of the total composition may be in the range of about 0% to about 25%. In some embodiments, the amount of the IMDA of the total composition may be in the range of about 0% to about 10%. In some embodiments, the amount of the IMDA of the total composition may be in the range of about 0% to about 5%. In some embodiments, the amount of the IMDA of the total composition may be in the range of about 0% to about 2.5%. In some embodiments, the amount of the IMDA of the total composition may be in the range of about 0.6% to about 1%. In some embodiments, the amount of the IMDA of the total amount of triterpenoids may be in the range of about 0% to about 50%. In some embodiments, the amount of the IMDA of the total amount of triterpenoids may be in the range of about 5% to about 35%. In some embodiments, the amount of the IMDA of the total amount of triterpenoids may be in the range of about 12% to about 26%. In some embodiments, the amount of the IMDA of the total amount of triterpenoids may be in the range of about 20% to about 26%.

In some embodiments, when 3-OAc-masticadienolic acid is one of the ingredients in the composition the amount of the 3-OAc-masticadienolic acid of the total composition may be in the range of about 0% to about 99%. In some embodiments, when 3-OAc-masticadienolic acid is one of the ingredients in the composition the amount of the 3-OAc-masticadienolic acid of the total composition may be in the range of about 0% to about 75%. In some embodiments, when 3-OAc-masticadienolic acid is one of the ingredients in the composition the amount of the 3-OAc-masticadienolic acid of the total composition may be in the range of about 0% to about 50%. In some embodiments, when 3-OAc-masticadienolic acid is one of the ingredients in the composition the amount of the 3-OAc-masticadienolic acid of the total composition may be in the range of about 0% to about 25%. In some embodiments, the amount of the 3-OAc-masticadienolic acid of the total composition may be in the range of about 0% to about 10%. In some embodiments, the amount of the 3-OAc-masticadienolic acid of the total composition may be in the range of about 0% to about 5%. In some embodiments, the amount of the 3-OAc-masticadienolic acid of the total composition may be in the range of about 0% to about 2.5%. In some embodiments, the amount of the 3-OAc-masticadienolic acid of the total composition may be in the range of about 0.5% to about 1%. In some embodiments, the amount of the 3-OAc-masticadienolic acid of the total amount of triterpenoids may be in the range of about 0% to about 50%. In some embodiments, the amount of the 3-OAc-masticadienolic acid of the total amount of triterpenoids may be in the range of about 5% to about 35%. In some embodiments, the amount of the 3-OAc-masticadienolic acid of the total amount of triterpenoids may be in the range of about 10% to about 26%. In some embodiments, the amount of the 3-OAc-masticadienolic acid of the total amount of triterpenoids may be in the range of about 20% to about 26%.

In some embodiments, when 3-OAc-epimasticadienolic acid is one of the ingredients in the composition the amount of the 3-OAc-epimasticadienolic acid of the total composition may be in the range of about 0% to about 99%. In some embodiments, when 3-OAc-epimasticadienolic acid is one of the ingredients in the composition the amount of the 3-OAc-epimasticadienolic acid of the total composition may be in the range of about 0% to about 75%. In some embodiments, when 3-OAc-epimasticadienolic acid is one of the ingredients in the composition the amount of the 3-OAc-epimasticadienolic acid of the total composition may be in the range of about 0% to about 50%. In some embodiments, when 3-OAc-epimasticadienolic acid is one of the ingredients in the composition the amount of the 3-OAc-epimasticadienolic acid of the total composition may be in the range of about 0% to about 25%. In some embodiments, the amount of the 3-OAc-epimasticadienolic acid of the total composition may be in the range of about 0% to about 10%. In some embodiments, the amount of the 3-OAc-epimasticadienolic acid of the total composition may be in the range of about 0% to about 5%. In some embodiments, the amount of the 3-OAc-epimasticadienolic acid of the total composition may be in the range of about 0% to about 2.5%. In some embodiments, the amount of the 3-OAc-epimasticadienolic acid of the total composition may be in the range of about 0.5% to about 1%. In some embodiments, the amount of the 3-OAc-epimasticadienolic acid of the total amount of triterpenoids may be in the range of about 0% to about 50%. In some embodiments, the amount of the 3-OAc-epimasticadienolic acid of the total amount of triterpenoids may be in the range of about 5% to about 35%. In some embodiments, the amount of the 3-OAc-epimasticadienolic acid of the total amount of triterpenoids may be in the range of about 10% to about 26%. In some embodiments, the amount of the 3-OAc-epimasticadienolic acid of the total amount of triterpenoids may be in the range of about 20% to about 26%.

In some embodiments, when 3-OAc-isomasticadienolic acid is one of the ingredients in the composition the amount of the 3-OAc-isomasticadienolic acid of the total composition may be in the range of about 0% to about 99%. In some embodiments, when 3-OAc-isomasticadienolic acid is one of the ingredients in the composition the amount of the 3-OAc-isomasticadienolic acid of the total composition may be in the range of about 0% to about 75%. In some embodiments, when 3-OAc-isomasticadienolic acid is one of the ingredients in the composition the amount of the 3-OAc-isomasticadienolic acid of the total composition may be in the range of about 0% to about 50%. In some embodiments, when 3-OAc-isomasticadienolic acid is one of the ingredients in the composition the amount of the 3-OAc-isomasticadienolic acid of the total composition may be in the range of about 0% to about 25%. In some embodiments, the amount of the 3-OAc-isomasticadienolic acid of the total composition may be in the range of about 0% to about 10%. In some embodiments, the amount of the 3-OAc-isomasticadienolic acid of the total composition may be in the range of about 0% to about 5%. In some embodiments, the amount of the 3-OAc-isomasticadienolic acid of the total composition may be in the range of about 0% to about 2.5%. In some embodiments, the amount of the 3-OAc-isomasticadienolic acid of the total composition may be in the range of about 0.5% to about 1%. In some embodiments, the amount of the 3-OAc-isomasticadienolic acid of the total amount of triterpenoids may be in the range of about 0% to about 50%. In some embodiments, the amount of the 3-OAc-isomasticadienolic acid of the total amount of triterpenoids may be in the range of about 5% to about 35%. In some embodiments, the amount of the 3-OAc-isomasticadienolic acid of the total amount of triterpenoids may be in the range of about 10% to about 26%. In some embodiments, the amount of the 3-OAc-isomasticadienolic acid of the total amount of triterpenoids may be in the range of about 20% to about 26%.

In some embodiments, when 3-OAc-epi-isomasticadienolic acid is one of the ingredients in the composition the amount of the 3-OAc-epi-isomasticadienolic acid of the total composition may be in the range of about 0% to about 99%. In some embodiments, when 3-OAc-epi-isomasticadienolic acid is one of the ingredients in the composition the amount of the 3-OAc-epi-isomasticadienolic acid of the total composition may be in the range of about 0% to about 75%. In some embodiments, when 3-OAc-epi-isomasticadienolic acid is one of the ingredients in the composition the amount of the 3-OAc-epi-isomasticadienolic acid of the total composition may be in the range of about 0% to about 50%. In some embodiments, when 3-OAc-epi-isomasticadienolic acid is one of the ingredients in the composition the amount of the 3-OAc-epi-isomasticadienolic acid of the total composition may be in the range of about 0% to about 25%. In some embodiments, the amount of the 3-OAc-epi-isomasticadienolic acid of the total composition may be in the range of about 0% to about 10%. In some embodiments, the amount of the 3-OAc-epi-isomasticadienolic acid of the total composition may be in the range of about 0% to about 5%. In some embodiments, the amount of the 3-OAc-epi-isomasticadienolic acid of the total composition may be in the range of about 0% to about 2.5%. In some embodiments, the amount of the 3-OAc-epi-isomasticadienolic acid of the total composition may be in the range of about 0.5% to about 1%. In some embodiments, the amount of the 3-OAc-epi-isomasticadienolic acid of the total amount of triterpenoids may be in the range of about 0% to about 50%. In some embodiments, the amount of the 3-OAc-epi-isomasticadienolic acid of the total amount of triterpenoids may be in the range of about 5% to about 35%. In some embodiments, the amount of the 3-OAc-epi-isomasticadienolic acid of the total amount of triterpenoids may be in the range of about 10% to about 26%. In some embodiments, the amount of the 3-OAc-epi-isomasticadienolic acid of the total amount of triterpenoids may be in the range of about 20% to about 26%.

In some embodiments, when MLA is one of the ingredients in the composition, the amount of the MLA of the total composition may be in the range of about 0% to about 25%. In some embodiments, when MLA is one of the ingredients in the composition, the amount of the MLA of the total composition may be in the range of about 0% to about 10%. In some embodiments, the amount of the MLA of the total composition may be in the range of about 0% to about 3%. In some embodiments, the amount of the MLA of the total composition may be in the range of about 0% to about 1%. In some embodiments, the amount of the MLA of the total composition may be in the range of about 0% to about 0.5%. In some embodiments, the amount of the MLA of the total composition may be in the range of about 0% to about 0.2%. In some embodiments, the amount of the MLA of the total composition may about 0.2%. In some embodiments, the amount of the MLA of the total amount of triterpenoids may be in the range of about 0% to about 25%. In some embodiments, the amount of the MLA of the total amount of triterpenoids may be in the range of about 0% to about 15%. In some embodiments, the amount of the MLA of the total amount of triterpenoids may be in the range of about 0% to about 4%. In some embodiments, the amount of the MLA of the total amount of triterpenoids may about 4%.

In some embodiments, when IMLA is one of the ingredients in the composition, the amount of the IMLA of the total composition may be in the range of about 0% to about 25%. In some embodiments, when IMLA is one of the ingredients in the composition, the amount of the IMLA of the total composition may be in the range of about 0% to about 10%. In some embodiments, the amount of the IMLA of the total composition may be in the range of about 0% to about 3%. In some embodiments, the amount of the IMLA of the total composition may be in the range of about 0% to about 1%. In some embodiments, the amount of the IMLA of the total composition may be in the range of about 0% to about 0.5%. In some embodiments, the amount of the IMLA of the total composition may be in the range of about 0% to about 0.2%. In some embodiments, the amount of the IMLA of the total composition may about 0.2%. In some embodiments, the amount of the IMLA of the total amount of triterpenoids may be in the range of about 0% to about 25%. In some embodiments, the amount of the IMLA of the total amount of triterpenoids may be in the range of about 0% to about 15%. In some embodiments, the amount of the IMLA of the total amount of triterpenoids may be in the range of about 0% to about 4%. In some embodiments, the amount of the IMLA of the total amount of triterpenoids may about 4%.

In some embodiments, the amount of the masticadienonic acid (MDA) may be in the range of about 0.05% to about 20%. In some embodiments, the amount of the isomasticadienonic acid (IMDA) may be in the range of about 0.05% to about 20%. In some embodiments, the amount of the oleanonic acid (OA) may be in the range of about 0.05% to about 20%. In some embodiments, the amount of the masticadienonic acid (MDA) may be in the range of about 0.1% to about 10%. In some embodiments, the amount of the isomasticadienonic acid (IMDA) may be in the range of about 0.1% to about 10%. In some embodiments, the amount of the oleanonic acid (OA) may be in the range of about 0.1% to about 10%. In some embodiments, the amount of the masticadienonic acid (MDA) may be in the range of about 0.5% to about 12%. In some embodiments, the amount of the isomasticadienonic acid (IMDA) may be in the range of about 0.5% to about 12%. In some embodiments, the amount of the oleanonic acid (OA) may be in the range of about 0.5% to about 12%. In some embodiments, the amount of the masticadienonic acid (MDA) may be in the range of about 0.5% to about 15%. In some embodiments, the amount of the isomasticadienonic acid (IMDA) may be in the range of about 0.5% to about 15%. In some embodiments, the amount of the oleanonic acid (OA) may be in the range of about 0.5% to about 15%.

In some embodiments, when NF-1 is one of the ingredients in the composition, the amount of the NF-1 of the total composition may be in the range of about 0% to about 75%. In some embodiments, when NF-1 is one of the ingredients in the composition, the amount of the NF-1 of the total composition may be in the range of about 0% to about 25%. In some embodiments, the amount of the NF-1 of the total composition may be in the range of about 0% to about 10%. In some embodiments, the amount of the NF-1 of the total composition may be in the range of about 0% to about 5%. In some embodiments, the amount of the NF-1 of the total composition may be in the range of about 0% to about 1%. In some embodiments, the amount of the NF-1 of the total composition may about 0.5%. In some embodiments, the amount of the NF-1 of the total amount of triterpenoids may be in the range of about 0% to about 50%. In some embodiments, the amount of the NF-1 of the total amount of triterpenoids may be in the range of about 5% to about 25%. In some embodiments, the amount of the NF-1 of the total amount of triterpenoids may be in the range of about 9% to about 13%.

In some embodiments, when NF-2 is one of the ingredients in the composition, the amount of the NF-2 of the total composition may be in the range of about 0% to about 75%. In some embodiments, when NF-2 is one of the ingredients in the composition, the amount of the NF-2 of the total composition may be in the range of about 0% to about 25%. In some embodiments, the amount of the NF-2 of the total composition may be in the range of about 0% to about 10%. In some embodiments, the amount of the NF-2 of the total composition may be in the range of about 0% to about 5%. In some embodiments, the amount of the NF-2 of the total composition may be in the range of about 0% to about 1%. In some embodiments, the amount of the NF-2 of the total composition may about 0.5%. In some embodiments, the amount of the NF-2 of the total amount of triterpenoids may be in the range of about 0% to about 50%. In some embodiments, the amount of the NF-2 of the total amount of triterpenoids may be in the range of about 5% to about 25%. In some embodiments, the amount of the NF-2 of the total amount of triterpenoids may be in the range of about 9% to about 13%.

In some embodiments, when NF-3 is one of the ingredients in the composition, the amount of the NF-3 of the total composition may be in the range of about 0% to about 75%. In some embodiments, when NF-3 is one of the ingredients in the composition, the amount of the NF-3 of the total composition may be in the range of about 0% to about 25%. In some embodiments, the amount of the NF-3 of the total composition may be in the range of about 0% to about 10%. In some embodiments, the amount of the NF-3 of the total composition may be in the range of about 0% to about 5%. In some embodiments, the amount of the NF-3 of the total composition may be in the range of about 0% to about 1%. In some embodiments, the amount of the NF-3 of the total composition may about 0.5%. In some embodiments, the amount of the NF-3 of the total amount of triterpenoids may be in the range of about 0% to about 50%. In some embodiments, the amount of the NF-3 of the total amount of triterpenoids may be in the range of about 5% to about 25%. In some embodiments, the amount of the NF-3 of the total amount of triterpenoids may be in the range of about 9% to about 13%.

In some embodiments, when NF-4 is one of the ingredients in the composition, the amount of the NF-4 of the total composition may be in the range of about 0% to about 75%. In some embodiments, when NF-4 is one of the ingredients in the composition, the amount of the NF-4 of the total composition may be in the range of about 0% to about 25%. In some embodiments, the amount of the NF-4 of the total composition may be in the range of about 0% to about 10%. In some embodiments, the amount of the NF-4 of the total composition may be in the range of about 0% to about 5%. In some embodiments, the amount of the NF-4 of the total composition may be in the range of about 0% to about 1%. In some embodiments, the amount of the NF-4 of the total composition may about 0.33%. In some embodiments, the amount of the NF-4 of the total amount of triterpenoids may be in the range of about 0% to about 50%. In some embodiments, the amount of the NF-4 of the total amount of triterpenoids may be in the range of about 2.5% to about 25%. In some embodiments, the amount of the NF-4 of the total amount of triterpenoids may be in the range of about 6% to about 9%.

In some embodiments, when NF-P is one of the ingredients in the composition, the amount of the NF-P of the total composition may be in the range of about 0% to about 25%. In some embodiments, when NF-P is one of the ingredients in the composition, the amount of the NF-P of the total composition may be in the range of about 0% to about 15%. In some embodiments, the amount of the NF-P of the total composition may be in the range of about 0% to about 7.5%. In some embodiments, the amount of the NF-P of the total composition may be in the range of about 0% to about 2.5%. In some embodiments, the amount of the NF-P of the total composition may be in the range of about 0% to about 1%. In some embodiments, the amount of the NF-P of the total composition may be in the range of about 0% to about 0.33%. In some embodiments, the amount of the NF-P of the total composition may about 0.33%. In some embodiments, the amount of the NF-P of the total amount of triterpenoids may be in the range of about 0% to about 50%. In some embodiments, the amount of the NF-P of the total amount of triterpenoids may be in the range of about 0% to about 25%. In some embodiments, the amount of the NF-P of the total amount of triterpenoids may be in the range of about 0% to about 7%. In some embodiments, the amount of the NF-P of the total amount of triterpenoids may be in the range of about 6% to about 7%.

In some embodiments, when NF-A is one of the ingredients in the composition, the amount of the NF-A of the total composition may be in the range of about 0% to about 25%. In some embodiments, when NF-A is one of the ingredients in the composition, the amount of the NF-A of the total composition may be in the range of about 0% to about 10%. In some embodiments, the amount of the NF-A of the total composition may be in the range of about 0% to about 3%. In some embodiments, the amount of the NF-A of the total composition may be in the range of about 0% to about 1%. In some embodiments, the amount of the NF-A of the total composition may be in the range of about 0% to about 0.5%. In some embodiments, the amount of the NF-A of the total composition may be in the range of about 0% to about 0.25%. In some embodiments, the amount of the NF-A of the total composition may about 0.25%. In some embodiments, the amount of the NF-A of the total amount of triterpenoids may be in the range of about 0% to about 25%. In some embodiments, the amount of the NF-A of the total amount of triterpenoids may be in the range of about 0% to about 15%. In some embodiments, the amount of the NF-A of the total amount of triterpenoids may be in the range of about 0% to about 6%. In some embodiments, the amount of the NF-A of the total amount of triterpenoids may be in the range of about 4% to about 6%.

In some embodiments, when NF-B is one of the ingredients in the composition, the amount of the NF-B of the total composition may be in the range of about 0% to about 25%. In some embodiments, when NF-B is one of the ingredients in the composition, the amount of the NF-B of the total composition may be in the range of about 0% to about 10%. In some embodiments, the amount of the NF-B of the total composition may be in the range of about 0% to about 3%. In some embodiments, the amount of the NF-B of the total composition may be in the range of about 0% to about 1%. In some embodiments, the amount of the NF-B of the total composition may be in the range of about 0% to about 0.5%. In some embodiments, the amount of the NF-B of the total composition may be in the range of about 0% to about 0.25%. In some embodiments, the amount of the NF-B of the total composition may about 0.25%. In some embodiments, the amount of the NF-B of the total amount of triterpenoids may be in the range of about 0% to about 25%. In some embodiments, the amount of the NF-B of the total amount of triterpenoids may be in the range of about 0% to about 15%. In some embodiments, the amount of the NF-B of the total amount of triterpenoids may be in the range of about 0% to about 6%. In some embodiments, the amount of the NF-B of the total amount of triterpenoids may be in the range of about 4% to about 6%.

In some embodiments, the pharmaceutically acceptable carrier may include a hydrophobic carrier. In some embodiments, the hydrophobic carrier may include at least one oil. In some embodiments, the oil may be selected from the group consisting of a mineral oil, a vegetable oil and combinations thereof. In some embodiments, the vegetable oil may be selected from the group consisting of cottonseed oil, olive oil, almond oil, canola oil, coconut oil, corn oil, grape seed oil, peanut oil, saffron oil, sesame oil, soybean oil, and combinations thereof. In some embodiments, the mineral oil may be light mineral oil. In some embodiments, the hydrophobic carrier may include at least one wax. In some embodiments, the hydrophobic carrier may include a combination of at least one oil and at least one wax.

In some embodiments, the pharmaceutically acceptable carrier may be a phospholipid.

In some embodiments, the composition may be in a form suitable for administration by a route selected from the group consisting of parenteral, transdermal, oral and topical.

In some embodiments, the composition may be in a form suitable for topical administration. In some embodiments, the composition may be in a form suitable for oral administration. In some embodiments, the composition is in a form suitable for parenteral administration. In some embodiments, the composition may be in a form suitable for administration by injection. In some embodiments, the composition is a parenteral formulation for administration by a route selected from the group consisting of subcutaneous, intravenous, intramuscular, intradermal, intraperitoneal, intraarterial, intracerebral, intracerebroventricular, intraosseous and intrathecal.

In some embodiments, the composition may be a parenteral formulation for administration by subcutaneous route. In some embodiments, the composition may be a parenteral formulation for administration by intramuscular route.

In various embodiments, the composition may be formulated for administration by a route selected from the group consisting of dermal, vaginal, rectal, inhalation, intranasal, ocular, auricular and buccal.

In some embodiments, the pharmaceutical composition may be in a form selected from the group consisting of a capsule, a tablet, a liposome, a suppository, a suspension, an ointment, a cream, a lotion, a solution, an emulsion, a film, a cement, a powder, a glue, an aerosol and a spray. In some embodiments, the capsule may be selected from the group consisting of a hard gelatin capsule and a soft gelatin capsule. In some embodiments, the emulsion is a nanoemulsion or a microemulsion.

In some embodiments, the formulation may include at least one of an inclusion complex, a nanoemulsion, a microemulsion, a powder, a lipid raft, a lipid microparticle, a dendrimer and a liposome. In some embodiments, the inclusion complex may include at least one cyclodextrin. In some embodiments, the at least one cyclodextrin may include hydroxypropyl-β-cyclodextrin. In some embodiments, the nanoemulsion may include droplets having average particle size of less than 800 nm. In some embodiments, the droplets may include droplets having average particle size of less than 500 nm. In some embodiments, the droplets may include droplets having average particle size of less than 200 nm. In some embodiments, the powder may include a spray dried powder. In some embodiments, the liposome may include a multilamellar vesicle. In some embodiments, the microemulsion may include a non-ionic surfactant. In some embodiments, the non-ionic surfactant may be selected from the group consisting of a polyoxyl castor oil, a polyoxyethylene sorbitan fatty acid ester (polysorbates), a poloxamer, a vitamin E derivative, a polyoxyethylene alkyl ether, a polyoxyethylene stearate, or saturated polyglycolyzed glyceride or combinations thereof.

In some embodiments, the composition may be disposed on the article of manufacture in the form of a coating. In some embodiments, the article of manufacture may include a vessel, wherein the composition may be disposed within the vessel. In some embodiments, the article of manufacture may be selected from the group consisting of a fabric article, a diaper, a wound dressing, a medical device, a needle or plurality of needles, a microneedle or plurality of microneedles, an injection device and a spray dispenser. In some embodiments, the article of manufacture may include a plurality of microneedles. In some embodiments, the medical device is selected from the group consisting of a prosthetic, an artificial organ or component thereof, a valve, a catheter, a tube, a stent, an artificial membrane, a pacemaker, a sensor, an endoscope, an imaging device, a pump, a wire and an implant. In some embodiments, the implant is selected from the group consisting of a cardiac implant, a cochlear implant, a corneal implant, a cranial implant, a dental implant, a maxillofacial implant, an organ implant, an orthopedic implant, a vascular implant, an intraarticular implant and a breast implant.

In some embodiments, the composition may be suitable for administration by a means selected from the group consisting of electroporation, sonication, radio frequency, pressurized spray and combinations thereof.

The pharmaceutical compositions of the invention may be manufactured in a manner which is itself known to one skilled in the art, for example, by means of conventional mixing, granulating, dragee-making, softgel encapsulation, dissolving, extracting, or lyophilizing processes. Pharmaceutical compositions for oral use may be obtained by combining the active compounds with solid and semi-solid excipients and suitable preservatives, and/or antioxidants. Optionally, the resulting mixture may be ground and processed. The resulting mixture of granules may be used, after adding suitable auxiliaries, if necessary, to obtain tablets, softgels, capsules, or dragee cores.

Suitable excipients are, in particular, fillers such as saccharides, e.g., lactose or sucrose, mannitol or sorbitol; cellulose preparations and/or calcium phosphates, e.g., tricalcium phosphate or calcium hydrogen phosphate; as well as binders, such as starch paste, using, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are flow-regulating agents and lubricants, e.g., silica, talc, stearic acid or salts thereof, such as magnesium stearate or calcium stearate, and/or polyethylene glycol. Dragee cores are provided with suitable coatings, which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropymethyl-cellulose phthalate, are used. Dye stuffs or pigments may be added to the tablets or dragee coatings, e.g., for identification or in order to characterize combinations of active compound doses.

Other pharmaceutical compositions for oral use include push-fit capsules made of gelatin, as well as soft, sealed capsules made of gelatin and a plasticizer, such as glycerol or sorbitol.

Formulations for parenteral administration include suspensions and microparticle dispersions of the active compounds as appropriate. In some embodiments, oily injection suspensions may be administered. Suitable lipophilic solvents or vehicles include fatty oils, e.g., sesame oil, or synthetic fatty acid esters, e.g., ethyl oleate, triglycerides, polyethylene glycol-400, cremophor, or cyclodextrins. Injection suspensions may contain substances which increase the viscosity of the suspension include, e.g., sodium carboxymethyl cellulose, sorbitol, and/or dextran. Optionally, the suspension may also contain stabilizers.

Pharmaceutical compositions can also be prepared using liposomes comprising the active ingredient. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolisable lipid capable of forming liposomes can be used. In general, the preferred lipids are phospholipids and the phosphatidyl cholines (lecithins), both natural and synthetic. Methods to form liposomes are known in the art, as disclosed for example, in Prescott, Ed., Methods in Cell Biology, Volume XIV, Academic Press, New York, N.Y. (1976) and in U.S. Pat. No. 7,048,943.

Formulations for topical administration include ointments. Suitable carriers include vegetable or mineral oils, white petrolatum, branched chain fats or oils, animal fats and waxes. The preferred carriers are those in which the active ingredient is soluble. Stabilizers, humectants and antioxidants may also be included, as well as agents imparting color or fragrance, if desired. Ointments may be formulated for example, by mixing a solution of the active ingredient in a vegetable oil such as almond oil with warm soft paraffin, and allowing the mixture to cool.

The pharmaceutical composition may comprise an oil-in-water emulsion or microemulsion in order to facilitate its formulation for oral, parenteral or topical use Such emulsions/microemulsions generally include lipids, surfactants, optionally humectants, and water. Suitable lipids include those generally known to be useful for creating oil-in-water emulsions/microemulsions, for example fatty acid glyceride esters. Suitable surfactants include those generally known to be useful for creating oil-in-water emulsions/microemulsions wherein lipids are used as the oil component in the emulsion. Non-ionic surfactants may be preferred, such as for example, ethoxylated castor oil, phospholipids, and block copolymers of ethylene oxide and propylene oxide. Suitable humectants, if used, include for example propylene glycol or polyethylene glycol.

The pharmaceutical composition may be formulated in the form of a gel, such as a hydrogel formed from a gel-forming polymer such as carrageenan, xanthan gum, gum karaya, gum acacia, locust bean gum, guar gum. A hydrogel may be combined with an oil-in-water emulsion comprising the active ingredient.

The pharmaceutical composition may be formulated in the form of a cement such as those comprising polymethylmethacrylate (PMMA) or calcium phosphate. In some embodiments, the pharmaceutical composition may be formulated in the form of a powder.

In some embodiments, the present invention provides therapeutic uses and methods of treating optic neuropathy condition in a subject in need thereof. The present invention provides therapeutic uses and methods of treating optic neuropathy condition in a subject in need thereof. In some embodiments, there is provided a method of treating optic neuropathy condition in a subject in need thereof, comprising administering to a subject a therapeutically effective amount of a composition comprising a combination of at least one triterpenoic acid and at least one neutral triterpenoid.

The step of administering the compositions may comprise any acceptable route including oral, topical, parenteral, and transdermal, such as, for example, parenteral administration includes intravenous, intramuscular, subcutaneous, intradermal, intraperitoneal, intraarterial, intrauterine, intraurethral, intracardial, intracerebral, intracerebroventricular, intrarenal, intrahepatic, intratendon, intraosseous, intrathecal, dermal, vaginal, rectal, inhalation, intranasal, ocular, auricular and buccal routes of administration.

In some embodiments, the method may be carried out prior to or following implantation of a medical device into the subject in order to prevent optic neuropathy condition. In some embodiments, the method may be carried out prior to or following implantation of a medical device into the subject in order to treat the implications/consequences of the condition. Medical devices include, but are not limited to a prosthetic, an artificial organ or component thereof, a valve, a catheter, a tube, a stent, an artificial membrane, a pacemaker, a sensor, an endoscope, an imaging device, a pump, a wire and an implant. Implants include, but are not limited to a cardiac implant, a cochlear implant, a corneal implant, a cranial implant, a dental implant, a maxillofacial implant, an organ implant, an orthopedic implant, a vascular implant, an intraarticular implant and a breast implant.

In some embodiments, the medical device is an organ implant, which may in certain cases comprise autologous cells of the subject.

In some embodiments, the step of contacting comprises a means selected from the group consisting of electroporation, sonication, radio frequency, pressurized spray and combinations thereof.

In some embodiments, the step of contacting comprises establishing contact between interstitial fluid and the composition. Contact between interstitial fluid and the composition may be accomplished by piercing and/or teasing the dermis with a needle, a microneedle, or an apparatus comprising a plurality of needles or microneedles. Such needles or microneedles are preferably non-hollow and may be fashioned in a plurality for example, on a comb or brush-like apparatus.

The method of the invention is suitable for application in humans and non-human mammals.

The method of the invention may encompass use of an article of manufacture which incorporates the composition comprising the combinations described herein.

In some embodiments, the step of administering the compositions disclosed herein may comprise any acceptable route including parenteral route. Parenteral administration includes, for example, intravenous, intramuscular, subcutaneous, intradermal, intraperitoneal, intraarterial, intrauterine, intraurethral, intracardial, intracerebral, intracerebroventricular, intrarenal, intrahepatic, intratendon, intraosseous. intraocular and intrathecal routes of administration. Each possibility is a separate embodiment.

In some embodiments, the compositions/formulations/combinations disclosed herein may be administered by any suitable administration route on any suitable administration regime at any suitable dose, depending on the subject characteristics (including, for example, age, gender, treated condition, severity of the condition, and the like). For example, administration may be performed 1-7 times a week. For example, administration may be performed more than once a day. For example, the compositions may be administered on a twice weekly schedule with even intervals. In some embodiments, the compositions may be administered on a schedule of every second day. In some embodiments, the compositions may be administered on a schedule of once every seventh day (once weekly). In some embodiments, the compositions may be administered once a day.

It is clear to a person skilled in the art that many variations of the above-indicated administration routes, schedules, doses and regimens can be envisaged and designed. It is to be understood that such variations in administration routes, schedules, doses and regimens are also within the scope of the current invention.

According to some embodiments, the methods disclosed herein for treating optic neuropathy are particularly advantageous for subjects afflicted with conditions resulting from or associated with damage to the optical nerve, such as, for example, glaucoma, Traumatic Neuropathy, Ischemic optic neuropathy (such as, for example, NAION and AION), Glaucoma, Neuropathy caused by tumors, Neuropathy caused by infections, Mitochondrial optic neuropathies, Nutritional optic neuropathies, Radiation optic neuropathy, Toxic optic neuropathy, Retinal diabetic complications, damage caused by deposition disease, and the like, or combinations thereof.

In some embodiments, the uses and methods disclosed herein for treating optic neuropathy are particularly advantageous for subjects afflicted with conditions resulting from or associated with damage to the optical nerve as a result of a deposition disease, such as, deposition of lipoproteinaceous substances in the optic nerve, deposition of lipofuscin.

In some embodiments, the uses and methods disclosed herein for treating optic neuropathy are particularly advantageous for subjects afflicted with conditions resulting from or associated with deposition of deposition of lipoproteinaceous substances in the optic nerve.

In some embodiments, the uses and methods disclosed herein for treating optic neuropathy are particularly advantageous for subjects afflicted with conditions resulting from or associated with damage to the optical nerve as a result of deposition of lipoproteinaceous substances in the optic nerve, wherein the deposition of lipoproteinaceous substances is the result of a storage disease.

In some embodiments, the uses and methods disclosed herein for treating optic neuropathy are particularly advantageous for subjects afflicted with conditions resulting from or associated with damage to the optical nerve as a result of deposition of lipoproteinaceous substances in the optic nerve, wherein the deposition of lipoproteinaceous substances is the result of a storage disease, and wherein the deposited lipoproteinaceous substance is lipofuscin.

In some embodiments, the uses and methods disclosed herein for treating optic neuropathy are particularly advantageous for subjects afflicted with conditions resulting from or associated with damage to the optical nerve as a result of deposition of mineral substances in the optic nerve, wherein the deposition of mineral substances is the result of a storage disease, and wherein the mineral substances deposited in the optic nerve contain calcium and/or iron.

In some embodiments, the uses and methods disclosed herein for treating optic neuropathy are particularly advantageous for subjects afflicted with Glaucoma.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

Isolation of Triterpenoic Acids and Neutral Triterpenoids from Mastic Gum

Many of the compositions disclosed in this application are prepared by mixing together individual triterpenoic acid(s) and neutral triterpene(s). These individual triterpenoic acid(s) and neutral triterpenoids can be extracted from a natural source such as for example Mastic gum. Alternatively, the compounds can be the product of a chemical synthesis. In other cases, mixtures obtained from partial purification from a natural source may also be a source of two or more compounds and such mixtures may be combined with one or more pure compounds obtained from a natural source or by chemical synthesis to provide compositions of the invention. A further possibility is the combination of two or more mixtures obtained from natural sources by partial purification from a natural source; and/or their combination with one or more pure compounds obtained by either chemical synthesis or isolation from a natural source. The actual origin of these individual compounds does not influence the properties of the prepared pharmaceutical compositions prepared using these individual compounds. It is therefore understood that the procedures given below for the isolation and synthesis of several individual triterpenoic acids and individual neutral triterpenes are only limited practical examples and that a person skilled in the art may use different isolation procedures and synthesis procedures for obtaining these individual compounds.

The current invention relates to the unexpected biological and pharmaceutical properties of the disclosed pharmaceutical compositions comprising triterpenoic acid(s) and neutral triterpenoid(s). The combination of triterpenoic acid(s) and neutral triterpenoid(s) results in an overall pharmaceutical activity which cannot be obtained by using only the triterpenoic acids or only the neutral triterpenoids.

Example 1A

Preparation of Isolated Acidic Fraction of Mastic Gum

To a 50 gram amount of mastic gum was added absolute ethanol (800 ML) and the mixture was left to stand for 24 hours. The mixture was shaken for 30 minutes at 150 rpm and left to stand for two hours. The obtained ethanol solution was decanted from insoluble material into a 3 L round bottom flask. To the insoluble material was added 400 ML of fresh ethanol and the mixture was shaken again 30 minutes at 150 rpm and was left to stand for 30 minutes. The obtained ethanol solution was decanted and added to the first ethanol solution. This step was repeated once more using 200 ML absolute ethanol. This gave 1.4 L of ethanol solution. The ethanol was evaporated using a rotary evaporator, and to the remaining material was added n-hexane (1.2 Liter) and the mixture was shaken at 150 rpm for 4 hours. It was then left to stand for 4 hours and the hexane solution was decanted from insoluble material into a 3 L Erlenmeyer. To the remaining insoluble material was added 800 ML fresh hexane and the mixture was shaken for 6 hours at 150 rpm and left to stand for 12 hours. The hexane solution was decanted into the 3 L Erlenmeyer flask containing the first 1.2 L of hexane solution. The hexane was evaporated in a clean 3 L roundbottom flask to give about 30 grams of extract. (Yields range typically from 50-70% depending on the age and particle size of the used Mastic gum.)

The obtained extracted material was subsequently dissolved in diethyl ether (500 ML) and extracted with a 5% aqueous sodium carbonate solution (4×100 ML), the basic aqueous layer and an oily/emulsion layer were carefully separated form the diethyl ether layer. The diethyl ether layer was then additionally extracted with 0.4 N aqueous sodium hydroxide (3×100 ML) and the basic aqueous layer and an oily/emulsion layer were again carefully separated from the diethyl ether layer. (This remaining diethyl ether layer is called diethyl ether layer Nr.I, and will be used below in Example 1B). The two basic aqueous extracts (including oily/emulsion layers) were separately acidified to pH 1-2 by slow addition of 10% aqueous hydrochloric acid and were subsequently extracted with fresh diethyl ether (3×200 ML). The thus obtained ethereal fractions were combined and dried over anhydrous sodium sulfate. After filtering off the sodium sulfate, the diethyl ether was removed using a rotary evaporator. This procedure gave ca. 15 gram of isolated acidic fraction of mastic gum as a white solid, corresponding to about 50% yield based on the intermediate extract obtained after the ethanol/hexane extraction. This particular isolated acidic fraction obtained from mastic gum as described hereinabove is termed "Acidic Mixture 1" or "Acidic-1".

Based on the starting 50 grams of Mastic gum, the yield for this acidic fraction is about 30%. Typical yields of this particular acidic fraction from mastic gum range from about 25% to about 35%. Without wishing to be bound to any theory or mechanism, these variations in yield can occur due to natural (e.g. seasonal) fluctuations in the composition of the Mastic gum and may also be influenced by age and storage conditions of the Mastic gum.

Example 1B

Isolation of the Neutral Fraction of Mastic Gum

The diethyl ether layer Nr. I obtained in Example 1A was transferred to a clean separatory funnel and washed with water (200 ML) and brine (150 ML). It was then dried over anhydrous sodium sulfate. The sodium sulfate was removed by filtration and the diethyl ether was evaporated using a rotary evaporator. This gave about 15 grams of isolated neutral fraction as a white to off-white sticky solid (which will become a very viscous liquid above 35-40° C.). This is about 50% yield based on the extract obtained after the ethanol/hexane extraction presented in Example 1A. This particular isolated neutral fraction obtained from mastic gum as described here is termed "Neutral Mixture 1" or "Neutral-1". Based on the starting 50 grams of Mastic gum, the yield for this neutral fraction ("Neutral Mixture 1") is about 30%. Typical yields of this neutral fraction from mastic gum range from about 25 to about 35%.

The mass-balance of this particular acid-base extraction described here is typically over 90% and often more than 95% based on the intermediate extract obtained after the ethanol/hexane extraction procedure. The ratio of the thus isolated acidic fraction ("Acidic Mixture 1") to isolated neutral fraction ("Neutral Mixture 1") is usually approaching 1:1 (and nearly always within the 0.8:1.2 to 1.2:0.8 range).

Isolation of individual triterpenoic acids and neutral triterpenoids from isolated acidic fractions and isolated neutral fractions can be accomplished using standard column chromatography and HPLC-methods as known to a person skilled in the art.

It is to be understood, and it is clear to a person skilled in the art, that other extraction protocols can be used to obtain different isolated acidic fractions and isolated neutral fractions from suitable plant materials. All such isolated acidic fractions and isolated neutral fractions can subsequently be used for the isolation of triterpenoic acids and neutral triterpenoids and/or preparation of compositions of the invention.

Example 1C

A further isolated acidic fraction of mastic gum was prepared according to the same method as Example 1A, but using methanol instead of ethanol as the polar solvent. Hexane was used as the non-polar solvent, and diethyl ether as the solvent for the acid-base extraction step.

Example 1D

A further isolated acidic fraction of mastic gum was prepared according to the same method as Example 1A, but using isopropanol as polar solvent. Hexane was used as the non-polar solvent, and diethyl ether as the solvent for the acid-base extraction step.

Example 1E

A further isolated acidic fraction of mastic gum was prepared according to the same method as Example 1A, but using n-heptane instead of hexane as the non-polar solvent. Ethanol was used as the polar solvent and diethyl ether as the solvent for the acid-base extraction.

Example 1F

A further isolated acidic fraction of mastic gum was prepared according to the same method as Example 1A, but using n-heptane instead of hexane as the non-polar solvent. Methanol was used as the polar solvent and diethyl ether as the solvent for the acid-base extraction.

Example 1G

A further isolated acidic fraction of mastic gum was prepared according to the same method as Example 1A, but using hexane as the non-polar solvent. Ethanol was used as the polar solvent and methyl-tert-butyl ether (MTBE) as the solvent for the acid-base extraction.

Example 1H

Isolated Acidic Fraction and Neutral Fraction of Mastic Gum Using Ion-Exchange Resin To a 50 gram amount of mastic gum was added absolute ethanol (800 ML) and the mixture was left to stand for 24 hours. The mixture was shaken for 30 minutes at 150 rpm and left to stand for two hours. The obtained ethanol solution was decanted from insoluble material into a 3 L round bottom flask. To the insoluble material was added 400 ML of fresh ethanol and the mixture was shaken again 30 minutes at 150 rpm and was left to stand for 30 minutes. The obtained ethanol solution was decanted and added to the first ethanol solution. This step was repeated once more using 200 ML absolute ethanol. This gave 1.4 L of ethanol solution. The ethanol was evaporated using a rotary evaporator, and to the remaining material was added n-hexane (1.2 Liter) and the mixture was shaken at 150 rpm for 4 hours. It was then left to stand for 4 hours and the hexane solution was decanted from insoluble material into a 3 L Erlenmeyer. To the remaining insoluble material was added 800 ML fresh hexane and the mixture was shaken for 6 hours at 150 rpm and left to stand for 12 hours. The hexane solution was decanted into the 3 L Erlenmeyer flask containing the first 1.2 L of hexane solution. The hexane was evaporated in a clean 3 L round bottom flask to give about 30 grams of extract. (Yields range typically from 50-70% depending on the age and particle size of the used Mastic gum.)

The obtained extract was dissolved in ethanol (0.5 L) and treated with 100 grams of a strongly basic ion-exchange resin (e.g. Dowex-1X8-400; Amberlite IRA 400; Diaion SA10A) on a shaker. The ion-exchange resin was filtered off and washed with methanol until TLC did not show any significant spots (the thus obtained ethanol solution and washings were combined, and used for Example 1I below). The resin was then treated with 10% ethanolic acetic acid solution in order to release the carboxylic acids from the resin. The ethanolic acetic acid mixture was evaporated to yield the isolated carboxylic acid fraction. Typical yields are around 50% of the starting extract (15 grams). This particular isolated acidic fraction obtained from mastic gum as described hereinabove is termed "Acidic Mixture 3" or "Acidic-3".

Example 1I

Isolated Neutral Fraction Obtained Via Ion-Exchange Resin

The combined ethanol filtrate and washings obtained from filtration of the ion-exchange resin in example 1H were evaporated to provide an isolated neutral fraction. This particular isolated neutral fraction obtained from mastic gum as described hereinabove is termed "Neutral Mixture 3" or "Neutral-3".

Example 2

Synthesis of Some Triterpenoic Acids and Some Neutral Triterpenoids

Synthesis A: Preparation of Oleanonic Acid

Oleanonic acid (also referred to herein as OA or OLN) was obtained in three steps from oleanolic acid.

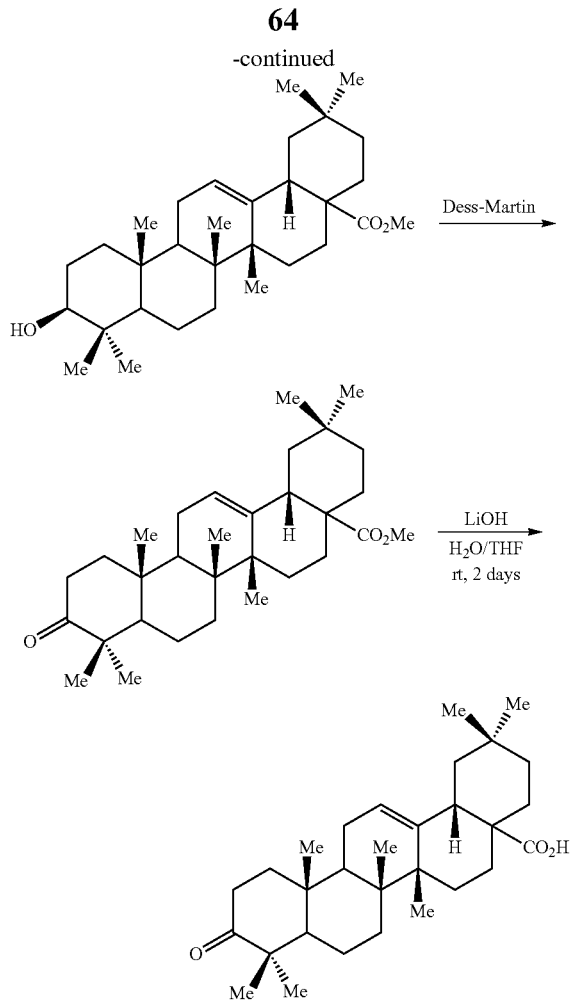

Oleanolic acid was first converted to the corresponding methyl ester by treatment with methyl iodide and potassium carbonate in dimethylformamide (DMF). Oxidation of oleanolic acid methyl ester to oleanonic acid methyl ester was performed using Dess-Martin periodane reagent in dichloromethane (DCM). Hydrolysis of oleanonic acid methyl ester with lithium hydroxide in aqueous THF gave upon acidification the desired oleanonic acid.

Synthesis B: Preparation of NF-A (Betulone)

NF-A was synthesized from betulin-28-acetate in two steps.

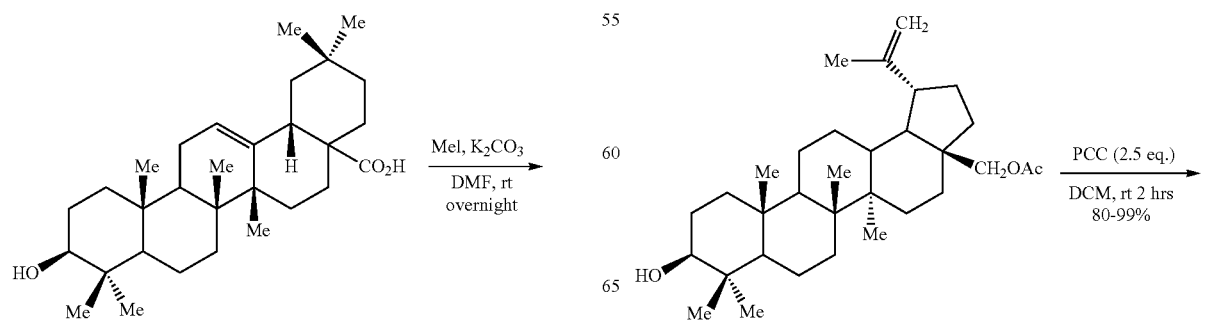

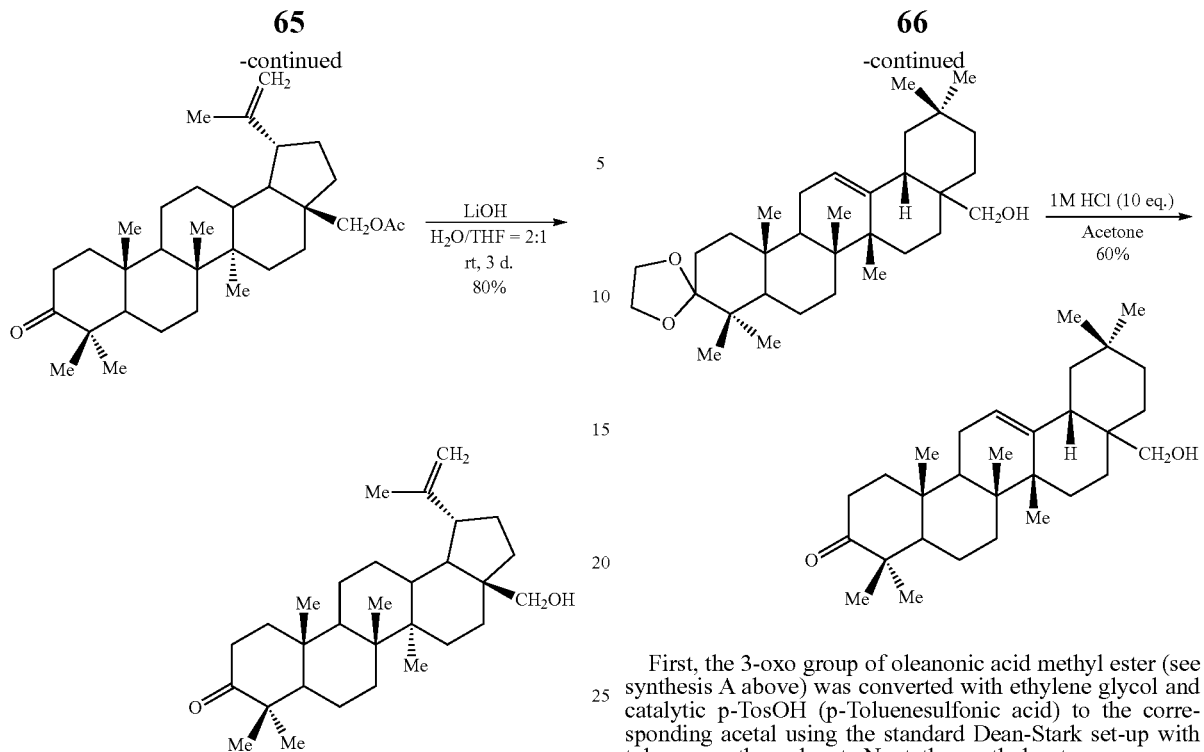

First the 3-hydroxyl-group was oxidized to the corresponding ketone with PCC in dichloromethane. This was followed by the hydrolysis of the C-28 acetate group to give the desired NF-A (Betulone).

Synthesis C: Preparation of NF-B (Oleanonic Alcohol; 28-hydroxy-beta-amyrone)

NF-B was synthesized from oleanonic acid methyl ester in three steps.

First, the 3-oxo group of oleanonic acid methyl ester (see synthesis A above) was converted with ethylene glycol and catalytic p-TosOH (p-Toluenesulfonic acid) to the corresponding acetal using the standard Dean-Stark set-up with toluene as the solvent. Next the methyl ester group was reduced to the corresponding alcohol with lithium aluminium hydride in THF. Hydrolysis of the acetal with diluted aqueous HCl in acetone gave the desired NF-B (oleanonic alcohol).

Synthesis D and E: Preparation of Oleanolic Alcohol (aka erythrodiol; 28-hydroxy-beta-amyrin) and NF-3 (oleanonic aldehyde)

It was found that oleanolic alcohol (aka erythrodiol) was most easily synthesized by reduction of oleanolic acid methyl ester (see synthesis A) with lithium aluminium hydride in THF. (Attempts to prepare this compound by direct reduction of oleanolic acid gave very low yields even after prolonged reaction times and using large excess of lithium aluminium hydride.)

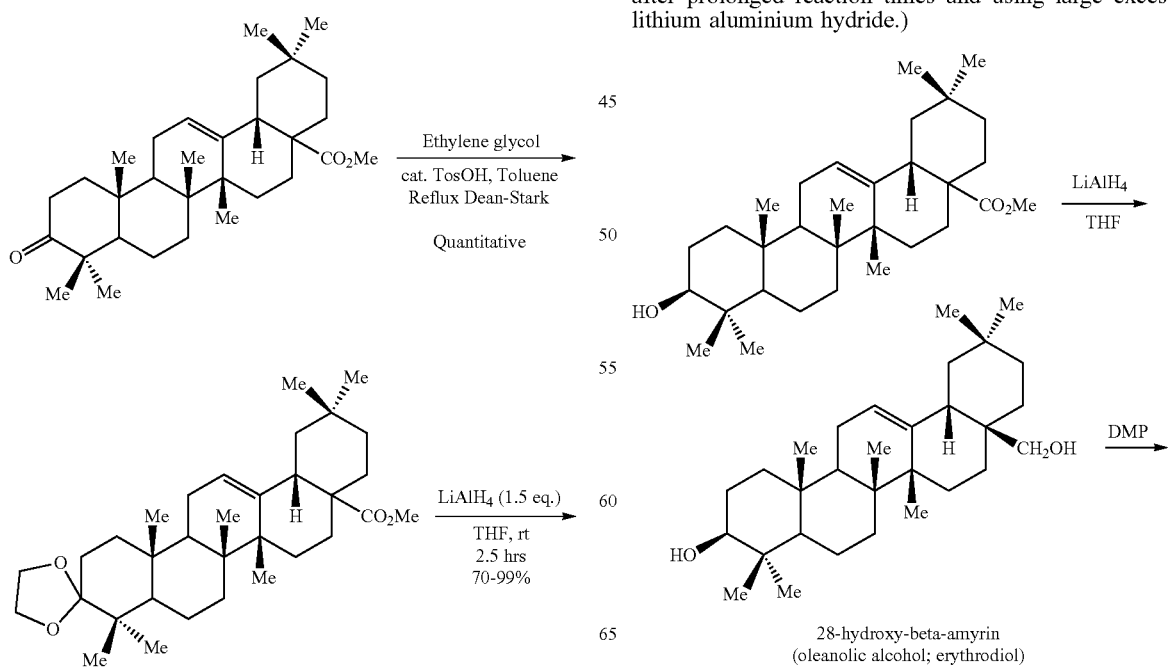

28-hydroxy-beta-amyrin
(oleanolic alcohol; erythrodiol)

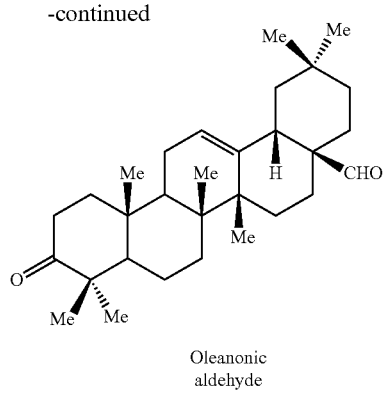

Oleanonic aldehyde

Oleanonic aldehyde (NF-3) was subsequently synthesized from oleanolic alcohol by oxidation using the Dess-Martin periodane reagent.

Synthesis F: Preparation of Masticadienonic Aldehyde

Masticadienonic aldehyde was prepared from masticadienonic acid in three steps. The methyl ester of masticadienonic acid was prepared using diazomethane. Reduction of the methyl ester with lithium aluminium hydride gave masticadienediol. The diol was then converted into masticadienonic aldehyde by oxidation with Dess-Martin Periodane reagent.

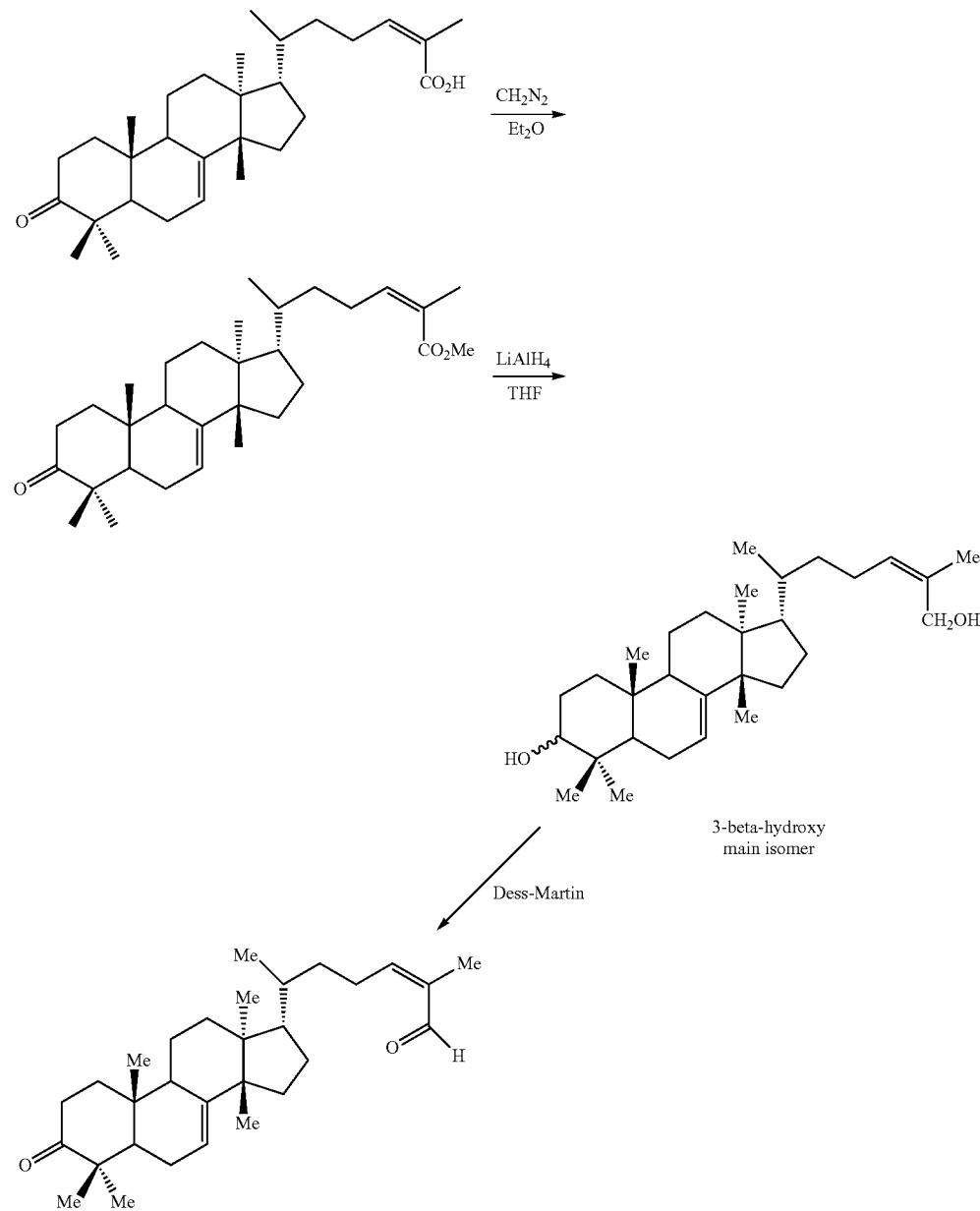

3-beta-hydroxy main isomer

Dess-Martin

Synthesis G: Preparation of Isomasticadienonic Aldehyde
Isomasticadienonic aldehyde was synthesized from isomasticadienonic acid using the same sequence of reactions as used for masticadienonic aldehyde in Synthesis E described above.
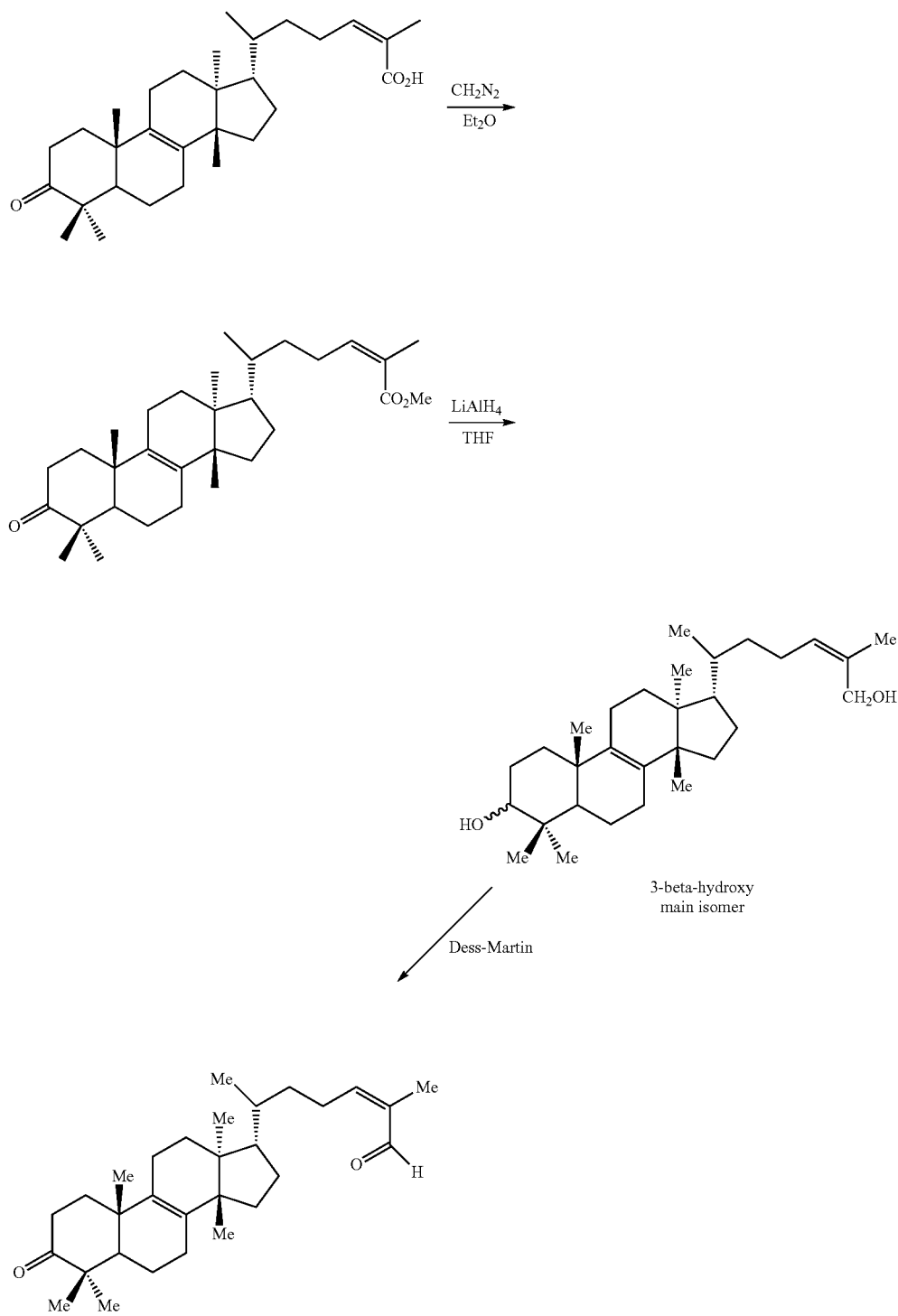
3-beta-hydroxy main isomer Synthesis H: Preparation of NF-2 ((8R)-3-Oxo-8-hydroxypolypoda-13E,17E,21-triene)

NF-2 was prepared from NF-1 by oxidation of the secondary hydroxyl group to the ketone using Dess-Martin periodane reagent.

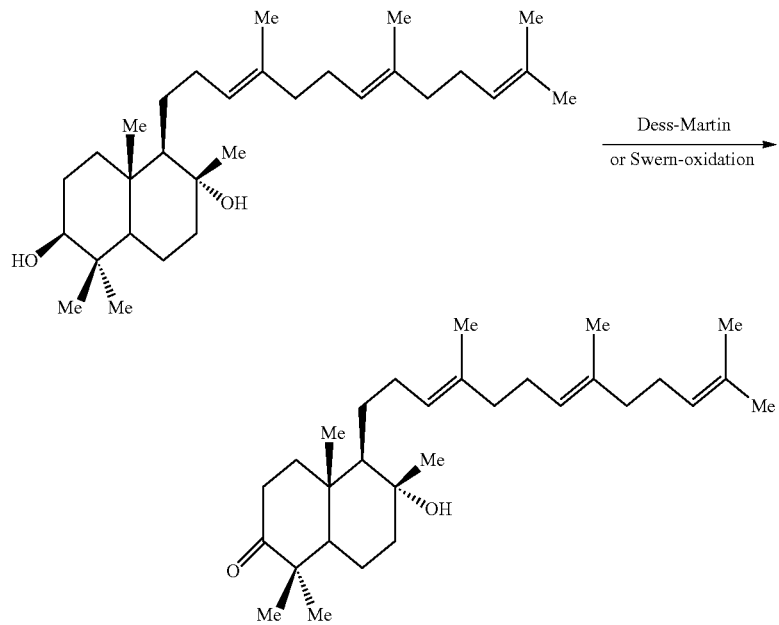

Other suitable oxidation methods for this reaction are the Swern-oxidation, pyridinium chlorochromate in DCM and the Oppenauer oxidation.

Synthesis I: Preparation of Beta-Amyrin

Beta-amyrin was prepared in five steps from oleanolic acid methyl ester.

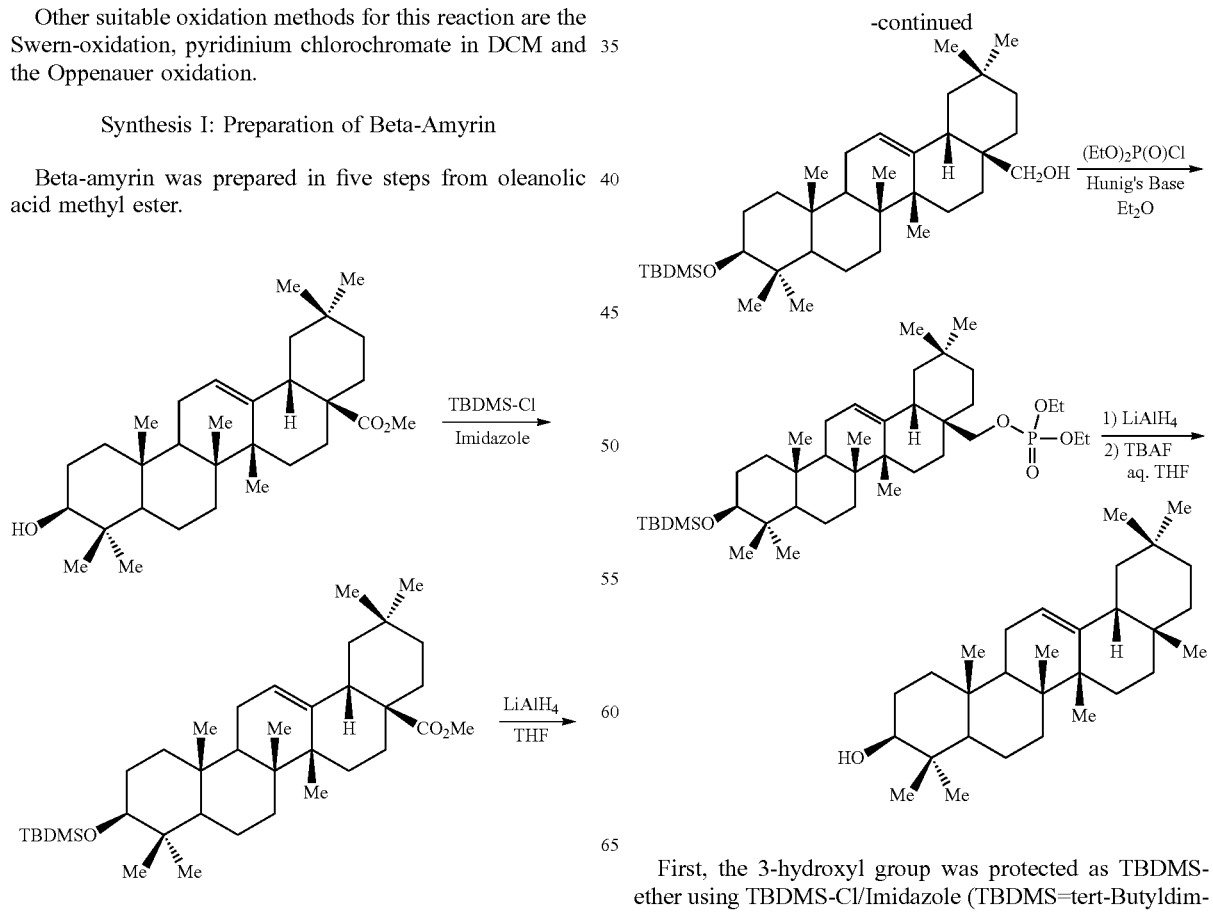

First, the 3-hydroxyl group was protected as TBDMS-ether using TBDMS-Cl/Imidazole (TBDMS=tert-Butyldimethylsilyl). This was followed by reduction of the methyl ester to the corresponding alcohol using lithium aluminium hydride, giving the monoprotected diol. The unprotected hydroxyl group was removed in a two-step sequence. First converting it into the corresponding diethylphosphate with diethyl chlorophosphate and Hunig's base. Thereafter, the phosphate was removed by reduction with lithium aluminium hydride resulting in the C-28 methyl group. Removal of the TBDMS protecting group with TBAF in aqueous THF gave the desired beta-amyrin.

Synthesis J: Preparation of Beta-Amyrone

Beta-amyrone was prepared from beta-amyrin by oxidation of the hydroxyl group to the corresponding ketone using either the Dess-Martin reagent or Swern oxidation.

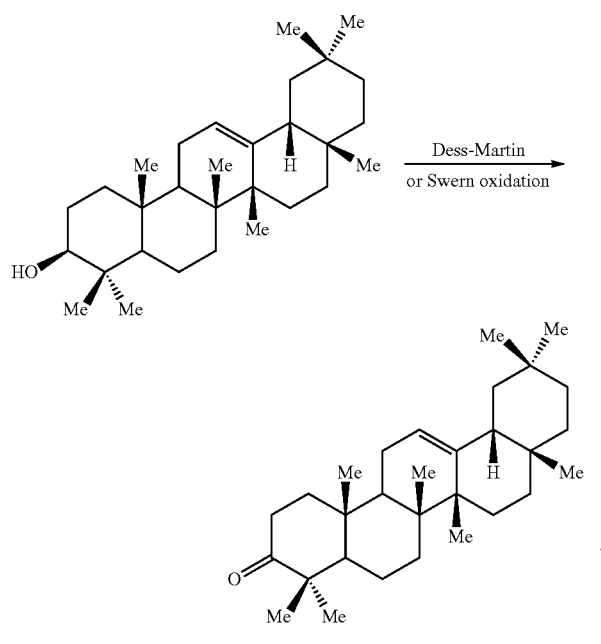

Other suitable oxidation methods for this reaction where the Swern-oxidation, pyridinium chlorochromate in DCM.

Synthesis L: Preparation of Oleanolic Aldehyde

Oleanolic aldehyde was prepared in two steps from the mono-protected diol intermediate from beta-amyrin Synthesis I.

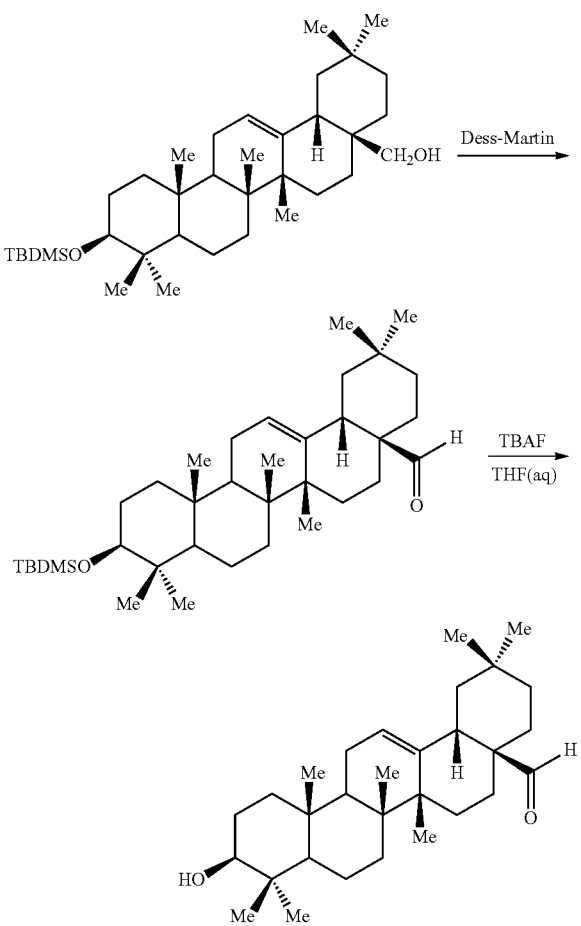

Synthesis K: Preparation of 28-oxo-lupen-3-one 28-oxo-lupen-3-one was synthesized from NF-A (betulone, see Synthesis B), by oxidation of the 28-hydroxyl group to the corresponding aldehyde with Dess-Martin periodane.

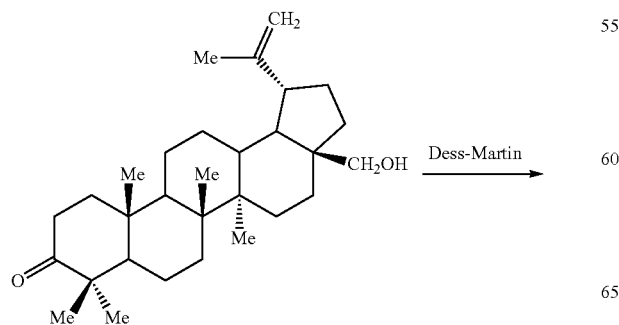

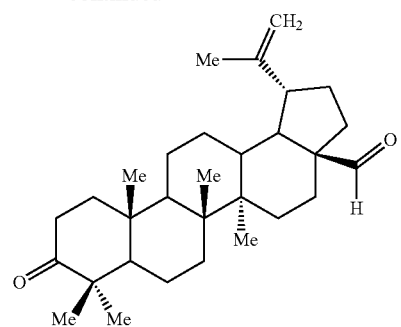

The free hydroxyl group was oxidized to the corresponding aldehyde using Dess-Martin Periodane. This was followed by removal of the TBDMS-group with TBAF in aqueous THF to give the desired oleanolic aldehyde.

Synthesis M: Preparation of 24-Z-Masticadienolic Acid (MLA)

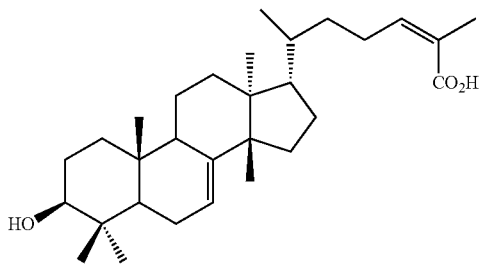

Masticadienonic acid (500 mg) was dissolved in methanol (30 ML) and cooled to 0° C. NaBH$_4$ (83 mg; 2.0 eq.) was added and the mixture was stirred overnight at room temperature. After TLC (hexane:ethylacetate) showed full conversion, the reaction mixture cooled to 0° C. and quenched by addition of 20 ML cold water. The methanol was evaporated from the mixture, which was then extracted with diethyl ether. The crude product was purified by column chromatography over silica gel (DCM:MeOH=95:5 to 90:10) to give MLA as white solid (400 mg; 80%).

Synthesis N: Preparation of 24-Z-Isomasticadienolic acid (IMLA)

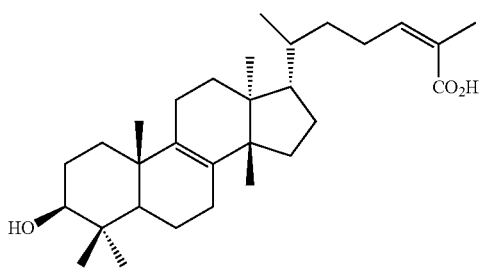

Isomasticadienonic acid (500 mg) was dissolved in methanol (30 ML) and cooled to 0° C. NaBH$_4$ (83 mg; 2.0 eq.) was added and the mixture was stirred overnight at room temperature. After TLC (hexane:ethylacetate) showed full conversion, the reaction mixture cooled to 0° C. and quenched by addition of 20 ML cold water. The methanol was evaporated from the mixture, which was then extracted with diethyl ether. The crude product was purified by column chromatography over silica gel (DCM:MeOH=95:5 to 90:10) to give IMLA as white solid (420 mg; 82%).

Synthesis O: Preparation of 24-Z-3-OAc-MLA (3-OAc-MLA)

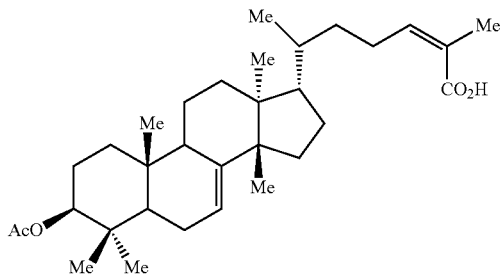

MLA (400 mg) was dissolved in anhydrous pyridine (5 ML), and acetic anhydride (160 mg; 3.55 eq.) was added in one portion. The mixture was stirred overnight at room temperature and monitored by TLC (hexane/ethylacetate). The reaction mixture was diluted with ethylacetate (15 ML) and 1M aqueous HCl (20 ML) and the mixture was stirred vigorously for 1 hour. The layers were separated, the organic layer was dried over MgSO$_4$ and evaporated. The crude product was purified by column chromatography over silicagel (hexane/ethylacetate=10:1 to 9:1) to yield 3-OAc-MLA as a white solid (220 mg; 55%).

Synthesis P: Preparation of 24-Z-3-OAc-IMLA (3-OAc-IMLA)

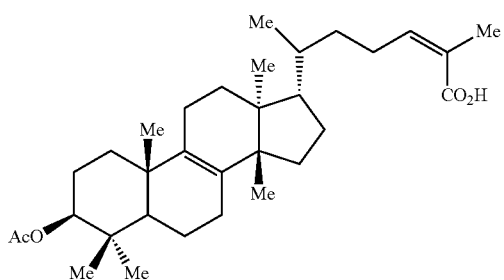

IMLA (400 mg) was dissolved in anhydrous pyridine (5 ML), and acetic anhydride (160 mg; 3.55 eq.) was added in one portion. The mixture was stirred overnight at room temperature and monitored by TLC (hexane/ethylacetate). The reaction mixture was diluted with ethylacetate (15 ML) and 1M aqueous HCl (20 ML) and the mixture was stirred vigorously for 1 hour. The layers were separated, the organic layer was dried over MgSO$_4$ and evaporated. The crude product was purified by column chromatography over silicagel (hexane/ethylacetate=10:1 to 9:1) to yield 3-OAc-IMLA as a white solid (190 mg; 47%).

Synthesis Q: Preparation of 24-Z-3-OAc-epi-MLA (3-OAc-epi-MLA)

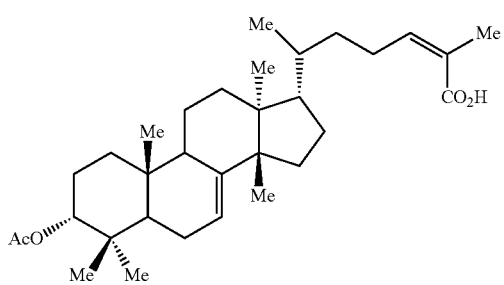

MLA (400 mg) was dissolved in anhydrous pyridine (5 ML), and acetic anhydride (160 mg; 3.55 eq.) was added in one portion, followed by 4-N,N-dimethylaminopyridine (DMAP; 20 mg). The mixture was stirred overnight at room temperature and monitored by TLC (hexane/ethylacetate). The reaction mixture was diluted with ethylacetate (15 ML) and 1M aqueous HCl (20 ML) and the mixture was stirred vigorously for 1 hour. The layers were separated, the organic layer was dried over MgSO$_4$ and evaporated. The crude product was purified by column chromatography over silicagel (hexane/ethylacetate=10:1 to 9:1) to yield a mixture of 3-OAc-MLA and 3-OAc-epi-MLA as a white solid (330 mg; %). The isomers were separated using preparative HPLC to provide 3-OAc-epi-MLA (120 mg) as a white solid.

Synthesis R: Preparation of 24-Z-3-OAc-epi-IMLA (3-OAc-epi-IMLA)

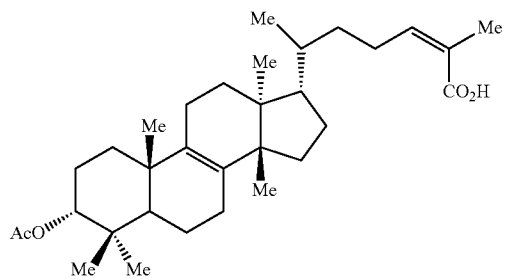

IMLA (400 mg) was dissolved in anhydrous pyridine (5 ML), and acetic anhydride (160 mg; 3.55 eq.) was added in one portion, followed by 4-N,N-dimethylaminopyridine (DMAP; 20 mg). The mixture was stirred overnight at room temperature and monitored by TLC (hexane/ethylacetate). The reaction mixture was diluted with ethylacetate (15 ML) and 1M aqueous HCl (20 ML) and the mixture was stirred vigorously for 1 hour. The layers were separated, the organic layer was dried over $MgSO_4$ and evaporated. The crude product was purified by column chromatography over silicagel (hexane/ethylacetate=10:1 to 9:1) to yield a mixture of 3-OAc-IMLA and 3-OAc-epi-IMLA as a white solid (310 mg; %). The isomers were separated using preparative HPLC to provide 3-OAc-epi-IMLA (110 mg) as a white solid.

Epi-MLA and epi-IMLA were prepared by hydrolysis of the corresponding acetates with LiOH in aqueous THF. Standard work-up provided the compounds in respective yields of 45% and 53% as white solids.

Dihydromasticadienonic acid and dihydroisomasticadienonic acid can be prepared according D. Barton et al. J. Chem. Soc. 1956, 4150.

Some suitable references for synthesis of several triterpenoids encountered in the current application are D. Barton et al. J. Chem. Soc. 1956, 4150 and 4158, V. Domingo et al. J. Org. Chem. 74, 6151, 2009, V. Domingo et al. Org. Biomol. Chem. 11, 559, 2013, and J. Justicia et al. Eur. J. Org. Chem. 10, 1778, 2004.

Example 3

Preparation of Pharmaceutical Compositions and Formulations

The pharmaceutical compositions as shown in Table 1 were prepared by mixing and dissolving the required amounts of triterpenoic acid(s) and neutral triterpenoid(s) in a suitable solvent (e.g. diethylether) followed by addition of the required amount of pharmaceutically acceptable carrier. The mixture was then shaken or stirred until a homogeneous clear solution was obtained, and the suitable solvent (e.g. diethyl ether) was removed using vacuum (e.g. a rotary evaporator). This gave the desired pharmaceutical composition.

Tables 1A and 1B show the pharmaceutical compositions that were prepared using diethyl ether as the suitable solvent, and pharmaceutical grade (NF-grade) cottonseed oil (stabilized with ca. 900 ppm BHT) as the pharmaceutically acceptable carrier.

TABLE 1A

| Cpd/Entry | A | B | C | D | E | F | G | H | I |
|---|---|---|---|---|---|---|---|---|---|
| 1 | Acidic-1 | Neutral-2 | | | | | | | |
| 2 | Acidic-1 | NF-1 | NF-2 | NF-3 | NF-4 | NF-A | NF-B | NF-P | |
| 3 | Acidic-1 | NF-1 | NF-2 | NF-3 | NF-4 | NF-A | NF-B | | |
| 4 | Acidic-1 | NF-1 | NF-2 | NF-3 | NF-4 | | | | |
| 5 | Acidic-1 | NF-1 | NF-2 | NF-3 | | | | | |
| 6 | Acidic-1 | NF-1 | NF-2 | | | | | | |
| 7 | Acidic-1 | NF-1 | | | | | | | |
| 8 | Acidic-1 | NF-2 | | | | | | | |
| 9 | Acidic-1 | NF-3 | | | | | | | |
| 10 | Acidic-2 | Neutral-1 | | | | | | | |
| 11 | Acidic-2 | Neutral-2 | | | | | | | |
| 12 | Acidic-2 | NF-1 | NF-2 | NF-3 | NF-4 | NF-A | NF-B | NF-P | |
| 13 | Acidic-2 | NF-1 | NF-2 | NF-3 | NF-4 | NF-A | NF-B | | |
| 14 | Acidic-2 | NF-1 | NF-2 | NF-3 | NF-4 | | | | |
| 15 | Acidic-2 | NF-1 | NF-2 | NF-3 | | | | | |
| 16 | Acidic-2 | NF-1 | NF-2 | | | | | | |
| 17 | Acidic-2 | NF-1 | NF-3 | | | | | | |
| 18 | Acidic-2 | NF-1 | NF-4 | | | | | | |
| 19 | Acidic-2 | NF-1 | | | | | | | |
| 20 | Acidic-2 | NF-2 | | | | | | | |
| 21 | Acidic-2 | NF-3 | | | | | | | |
| 22 | Acidic-2 | NF-4 | | | | | | | |
| 23 | Acidic-2 | NF-A | | | | | | | |
| 24 | Acidic-2 | NF-B | | | | | | | |
| 25 | MDA | IMDA | NF-1 | NF-2 | NF-3 | NF-4 | NF-A | NF-B | |
| 26 | MDA | IMDA | NF-1 | NF-2 | NF-A | NF-B | NF-P | | |
| 27 | MDA | IMDA | NF-1 | NF-2 | NF-A | NF-B | | | |
| 28 | MDA | IMDA | NF-3 | NF-4 | NF-A | NF-B | | | |
| 29 | MDA | IMDA | NF-1 | NF-2 | NF-3 | | | | |
| 30 | MDA | IMDA | NF-1 | NF-2 | NF-4 | | | | |
| 31 | MDA | IMDA | NF-1 | NF-2 | | | | | |
| 32 | MDA | IMDA | NF-1 | | | | | | |
| 33 | MDA | IMDA | NF-2 | | | | | | |
| 34 | MDA | IMDA | NF-3 | | | | | | |
| 35 | MDA | IMDA | NF-4 | | | | | | |
| 36 | MDA | IMDA | OA | MA | NF-1 | NF-2 | | | |
| 37 | MDA | IMDA | OA | MA | NF-1 | | | | |
| 38 | MDA | IMDA | OA | MA | NF-2 | | | | |
| 39 | MDA | IMDA | OA | MA | NF-3 | NF-4 | NF-A | NF-B | NF-P |
| 40 | MDA | IMDA | OA | MA | NF-3 | NF-4 | | | |
| 41 | MDA | IMDA | OA | NF-1 | NF-2 | | | | |
| 42 | MDA | IMDA | OA | NF-1 | | | | | |
| 43 | MDA | IMDA | OA | NF-2 | | | | | |
| 44 | MDA | IMDA | NF-1 | NF-2 | NF-3 | NF-4 | | | |

TABLE 1B

| Entry | | | | | | |
|---|---|---|---|---|---|---|
| 1 | 3-OAc-MLA | 3-OAc-IMLA | MDA | IMDA | NF-3 | NF-4 |
| 2 | 3-OAc-MLA | 3-OAc-epi-IMLA | MDA | IMDA | NF-3 | NF-4 |
| 3 | 3-OAc-epi-MLA | 3-OAc-IMLA | MDA | IMDA | NF-3 | NF-4 |
| 4 | 3-OAc-MLA | 3-OAc-IMLA | NF-3 | NF-4 | | |
| 5 | 3-OAc-MLA | 3-OAc-epi-IMLA | NF-3 | NF-4 | | |
| 6 | MDA | NF-3 | NF-4 | | | |
| 7 | MDA | NF-4 | | | | |
| 8 | IMDA | NF-3 | NF-4 | | | |
| 9 | IMDA | NF-4 | | | | |

The terms "Acidic-1", "Acidic-2" refer to the "Acidic Mixture 1" and "Acidic Mixture-2" respectively as described in Example 1A and Example 4. The terms "Neutral-1" and "Neutral-2" refer to the "Neutral Mixture 1" and "Neutral Mixture 2" respectively as described in Example 1B and Example 4.

A mixture of one of the Acidic Mixtures with one of the Neutral Mixtures is designated herein by the abbreviation AxNy, with x and y respectively denoting the number of the particular Acidic Mixture and Neutral Mixture in equal parts by weight. For example, A1N2 will stand for a 1:1 by weight mixture of Acidic Mixture 1 (Acidic-1) with Neutral Mixture 2 (Neutral-2).

Example 4

Effect of Various Compositions on Retinal Ganglion Cells (RGC) Upon Optic Nerve Axotomy Axotomy of the optic nerve is performed on the right eye of deeply anesthetized rats (19 rats per group). The test groups receive a sub-dermal injection in the posterior neck area of the compositions (0.025 ml/injection), and the control group is similarly injected with the same volume of vehicle (for example, cottonseed oil). The first injection is given to all the animals directly after surgery. Subsequent injections (same dosage and method of administration) are administered twice a week, every 3 to 4 days.

Fourteen days after axotomy, a fluorescent retrograde neurotracer (Di-Asp) is inserted into the axotomized optic nerve in order to stain surviving Retinal Ganglion Cells (RGC), and 24 hours later, the rats are sacrificed in a $CO_2$ saturated chamber and the injured right eye is enucleated. The retinas are isolated, and flattened on a slide and fixed with xylene based mounting medium.

Whole-mount retinas are evaluated with a fluorescent microscope. Dyed cells are counted manually.
Compositions Used Include:

"Acidic Mixture 1" (or "Acidic-1") means the isolated acidic fraction of Mastic gum as prepared according to Example 1A. "Acidic Mixture 1" contains as main compounds the following:
MA: Moronic acid (12-15%)
OA: Oleanonic acid (18-20%)
MDA: 24-Z-Masticadienonic acid (20-22%)
IMDA: 24-Z-Isomasticadienonic acid (22-26%)
3-beta-OAc-24-Z-masticadienolic acid (4-7%)
3-beta-OAc-24-Z-isomasticadienolic acid (4-7%)

It may further contain a number of other triterpenoic acids in small amounts, typically less than 5%. Possible triterpenoic acids that it may contain are:
MLA: 3-beta-masticadienolic acid
IMLA: 3-beta-isomasticadienolic acid
3-OAc-epimasticadienolic acid
3-OAc-epi-isomasticadienolic acid
Epimasticadienolic acid (3-alpha-masticadienolic acid)
Epi-isomasticadienolic acid (3-alpha-isomasticadienolic acid)
Dihydromasticadienonic acid
Dihydroisomasticadienonic acid "Acidic Mixture 2" (or "Acidic-2") Contains the Following Compounds in % (w/w):
MA: Moronic acid (15%)
OA: Oleanonic acid (15%)
MDA: 24-Z-Masticadienonic acid (25%)
IMDA: 24-Z-Isomasticadienonic acid (30%)
3-beta-OAc-24-Z-masticadienolic acid (8%)
3-beta-OAc-24-Z-isomasticadienolic acid (7%)

In Table 2, "Acidic Mixture 1 (2.5%)" means a 2.5% (w/w) formulation of the acidic fraction as isolated in Example 1A in cottonseed oil. Likewise, "Acidic Mixture 2 (or "Acidic-2") (2.5%)" means a 2.5% (w/w) formulation of "Acidic Mixture 2" as defined above, "Neutral Mixture 1" (or "Neutral-1") is the neutral fraction as prepared according to Examples 1A,B;

"Neutral Mixture 2" (or "Neutral-2") contains the following neutral triterpenoids:

NF-1: (8R)-3-beta, 8-dihydroxypolypoda-13E,17E,21-triene
NF-2: (8R)-3-Oxo-8-hydroxypolypoda-13E,17E,21-triene
NF-3: Oleanonic aldehyde
NF-4: Tirucallol
NF-P: Dipterocarpol (20-hydroxydammar-24-en-3-one)
NF-A: (Betulon), 28-hydroxylup-20(29)-en-3-one
NF-B: Oleanonic alcohol; (28-hydroxy-beta-amyrone)
3-beta-hydroxy-13-alpha-malabarica-14(26),17E,21-triene
20-hydroxy-lupan-3-one
28-Nor-17-hydroxylupen-3-one
28-oxo-lupen-3-one
28-nor-beta-amyrone
Isomasticadienonic aldehyde
Isomasticadienediol
Masticadienediol
Oleanolic aldehyde (28-oxo-beta-amyrin),
3-beta-20-dihydroxylupane
Masticadienonic aldehyde
3-oxo-malabarica-14(26),17E,21-triene
Beta-amyrone
Beta-amyrin
Germanicol.

A mixture of one of the Acidic Mixtures with one of the Neutral Mixtures is designated herein by the abbreviation AxNy, with x and y respectively denoting the number of the particular Acidic Mixture and Neutral Mixture in equal parts by weight. For example, Composition A1N2 in Table-2 stands for a 1:1 by weight mixture of Acidic Mixture 1 (Acidic-1) with Neutral Mixture 2 (Neutral-2).

The concentrations (in cottonseed oil) of each compound/fraction in the different compositions used are presented in Table 2.

TABLE 2

| Composition | Administered fraction/compound(s) | Concentrations (% w/w) |
|---|---|---|
| Composition A | MDA; IMDA; NF-(1,2,3,4,A,B) | MDA, IMDA: 1% each. NF-(1,2,3): 0.5% each NF-4: 0.33% NF-(A,B): 0.25% each |
| Composition B | MDA; IMDA; NF-(1,2,3,4) | MDA, IMDA: 1% each. NF-(1,2,3): 0.5% each NF-4: 0.33% |
| Composition C | MDA; IMDA; NF-(1,2) | MDA, IMDA: 1% each. NF-(1,2): 0.5% each |
| Composition (A1N2) | Acidic-1; Neutral-2 | Acidic-1: 2.5% Neutral-2: 2.5% |
| Composition F | Acidic Mixture 1 + NF-(1,2,3,4) | Acidic Mixture 1: 2.5% NF-(1,2,3): 0.5% each NF-4: 0.33% |
| Composition G | MDA+ IMDA + NF-(1,2,3,4,P,A,B) + MLA+ IMLA | MDA, IMDA: 1% each NF-(1,2,3): 0.5% each NF-(4,P): 0.33% each NF-(A,B): 0.25% each MLA, IMLA: 0.2% each |
| Composition H | Acidic Mixture 1 + NF-(1,2,3,4,P,A,B) | Acidic Mixture 1: 2.5%; NF(1,2,3): 0.50% each. NF(4,P): 0.33% each. NF(A,B): 0.25% each |
| Composition I | MDA+ IMDA+ NF-(1,2,3,4,P,A,B) | MDA; IMDA 1% each NF-(1,2,3): 0.5% each NF-(4,P): 0.33% each NF-(A,B): 0.25% each |

Example 5

Retinal Detachment (RD) Model—Effect of Various Compositions

Retinal detachment (RD) is performed on the right eye of deeply anesthetized animals (xylazine 50 mg/kg and ketamine 35 mg/kg) following dilatation of the pupil with Tropicamide drops 0.5%. RD is induced through the generation of a small opening in the retina at the ora serata followed by a sub-retinal injection of 5 µl saline with a 30G syringe needle. Approximately half of the retinal area is detached by this procedure.

Rats with RD are divided into nine experimental groups, eight test groups (Table 2; Example 4) receiving a sub-dermal injection in the posterior neck area of the indicated pharmaceutical compositions (0.025 ml/injection, Table 2), and the control group injected is administered with the same volume of cottonseed oil vehicle. The first injection is given to all the animals directly after surgery. The second injection (same dosage and method of administration) is administered 48 hours after surgery.

On days 3 and 14 days after RD, the operated rats are euthanized in a $CO_2$ saturated chamber. The injured right eye and the untreated left eye are enucleated. The retinas are isolated, frozen on dry ice and processed for Western blot analysis or immunohistochemical analysis. The left eye retinas serve as non-operated controls.

The expression levels of Semaphorin3A (Sema3A), Neuropilin1 (NP1), and GAP43 are determined. Caspase3 is used as an apoptotic marker, and morphological changes in Müller and microglial cells are examined.

The morphological changes of the Muller cells are studied by staining for glial fibrillary acidic protein (GFAP). GFAP labels Muller cells in the retina, and is commonly used as a stress indicator. Microglial invasion and activation are regarded as harmful or beneficial to neurons. Microglial activation after acute injury is primarily a reactive and adaptive glial cell response, which is triggered by injured neurons and which is designed to ameliorate primary tissue damage and to promote subsequent repair and gliosis (glial scar) as a result. Microglia become activated in the retina usually after injury, stimulate and recruit endothelial cells and fibroblasts Immunohistochemical analysis of sections of detached and non-injured retinas labeled with IB4 and stained with the nuclear dye PI are used to identify any signs of activated microglial cells in the retina.

Example 6 rAION, a Rodent Model of NAION (Nonarteritic Anterior Ischemic Optic Neuropathy)—Effect of Various Compositions Optic nerve ischemia effected by NAION results in myelin and axonal damage. In the rodent model of NAION (rAION), the optic nerve ischemia (in anesthetized rats) is laser-induced using a nd-YAG laser at 532 nm with 500 micron spot size and 50 mW power with 1 second pulses. This results in optic nerve ischemia without causing direct thermal damage. The induction results in postinfarct demyelation and oligodendricyte death in the following days. Demyelation results in the release of soluble factors that can inhibit axonal regeneration. These factors include myelin-associated glycoprotein (MAG) and NOGO66. These factors activate the axonal membrane protein complex (LINGO-1), which in turn activates the axonal kinase RAS homolog A (RhoA) via phosphorylation. Activated RhoA inhibits cytoskeleton polymerization, which results in axonal growth cone collapse.

Animals are divided over several groups with 10-12 animals per group.

Three days post-induction, treatment of the animal groups with the different compositions of the invention and placebo control (Table 2, above) is commenced. A twice-weekly regimen with 50 microliter subcutaneous injections is applied. Treatment is elicited for 28 days or 56 days.

Improvement of axonal regeneration is detected by GAP43 immunostaining. Optic nerve ultrastructure is evaluated after treatment in order to detect myelation profiles of different axon fiber sizes. Results of treatment and placebo groups are compared.

Example 7

In Vitro Glaucoma Model—Effect of Various Compositions

Primary acutely dissociated retinal cell culture are prepared from adult Wistar rats. The neuroprotective effects of the test compositions (combinations) on RGC survival is determined by pre-treatment prior to trophic factor withdrawal. Cell viability is assessed by double-label immunocytochemistry.

Adult Wistar rats are euthanized and retinal cell suspensions are prepared by dissecting the retinas and incubating (37° C., 30 min) in digestion buffer containing neurobasal medium supplemented with 2 mg/mL papain, 0.4 mg/mL dl-cysteine, and 0.4 mg/mL bovine serum albumin (BSA).

Retinas are processed in order obtain a suspension of single cells. Retinal cells are seeded on poly-d-lysine- and laminin-coated 8-well culture slides at a density of approximately $1 \times 10^6$ cells/well with 0.5 mL/well RGC culture medium and cultured in 95% air and 5% $CO_2$ at 37° C. for 3 days.

Cells are treated with either test composition or vehicle (control) immediately after dissociation and exposed to RGC culture medium as above, but without BDNF, CNTF, and bFGF (TFW RGC medium).

TABLE 3

| Condition | Media | Drug treatment |
|---|---|---|
| Control (3 technical replicates) | Complete RGC medium | N/A |
| Test compound (12 compounds, 3 technical replicates each) | Complete RGC medium | Test compound |
| Control (3 technical triplicates) | TFW RGC medium | N/A |
| Test compounds (12 compounds, 3 technical replicates and 2 concentrations each) | TFW RGC medium | Test compound |
| Test compound specific vehicle (3 technical replicates per vehicle) | TFW RGC medium | Vehicle |

On Day 3, cultures of retinal cells are subjected to double-label immunocytochemistry. Cultures are immunoreacted with primary antibodies against Thy-1 and neurofilament-1 68 kDa. Cells are co-labelled with DAPI to visualize nuclei.

Healthy RGCs are identified based on double-positive immunoreactivity for both Thy-1 and neurofilament-1 68 kDa, as well as the following four morphological criteria: presence of continuous membranes; no signs of vacuolation;

no signs of perikaryal swelling; and no signs of nuclear pyknosis or fragmentation. Cells are counted manually.

Example 8

Treatment of Glaucoma Using Various Compositions of the Invention

Various compositions (as listed in Table 2, above) are tested for their efficacy in Glaucoma treatment in rats. Glaucoma symptoms are induced in rats by intraocular (intravitreal) injection of excitotoxic agents such as N-methyl-d-aspartate (NMDA), alpha-amino-3-hydroxy-5-methyl-4-isoxazoleproprionic acid (AMPA) or kainic acid, or by physical means, such as, photocoagulation, for example, by irradiation with a laser beam. These agents induce degenerative conditions in the eye that are similar to glaucoma. The extent to which the compositions of the invention are able to ameliorate and/or reverse the degenerative symptoms caused by the excitotoxic agents is a measure of their effect in the treatment of glaucoma.

Degeneration of retinal ganglion cells (RGCs) in human and experimental glaucoma is accompanied by a neuroinflammatory process involving retinal microglial cells and increased production of inflammatory mediators. In addition, early and exacerbated activation of retinal microglial cells has been proposed to contribute to the degenerative process, suggesting that the control of microglia reactivity can prevent the glaucomatous loss of RGCs. A wide variety of animal models of glaucoma including pigs, dogs, monkeys and rodents, most of these models involve optic nerve damage mediated through ocular hypertension. Other established models available to study glaucoma rely on RGC induced-death upon genetic mutations, mechanical trauma to the optic nerve, toxic insult to retinal neurons, or the induction of retinal ischemia.

In this study the rat laser photocoagulation (GL) model is used in order to evaluate the neuroprotective and neuroregenerative effects of the tested compositions.

Study Design:

Briefly, high IOP is unilaterally induced by laser photocoagulation of episcleral veins on day 0 and day 7. The contralateral eye serves as control. The compositions are delivered subcutaneously (s.c) twice a week starting on day 1 only in animals with IOP of 16 mmHg or higher. IOP is monitored on the next day after the lasering (study day 1), on day 4, day 7 and once a week afterwards. The function of retinal ganglion cells (RGCs) is evaluated in vivo using pattern electroretinography (pERG) at the baseline, on day 14 and on day 28. Measurements at day 28 serve as milestone decision for an optional follow-up period of 2-4 weeks, at the end of which an additional pERG measurement is performed. The retinas and optic nerves are collected and processed for retinal ganglion cell counts and optic nerve axon counts. In addition, immunohistochemical evaluation of retinal tissue is performed for markers of inflammation.

The following treatment arms (n=12 rats in each arm) are used:
  Group 1: Naïve rats (n=12); (Naïve)
  Group 2: Vehicle—treated GL model (n=12); (Vehicle)
  Group 3: Test composition 1—treated GL model (n=12); Composition A (MDA, IMDA, NF-1,2,3,4,A,B. As detailed in Table 2)
  Group 4: Test composition 2—treated GL model (n=12); Composition B (MDA, IMDA, NF-1,2,3,4 As detailed in Table 2)
  Group 5: Test composition 3—treated GL model (n=12); Composition "Acidic-1+Neutral-2" (A1N2 with "Acidic-1" and "Neutral-2" as described in Example 4, Table 2.)

Materials and Methods

Rat Glaucoma Model

Experimental increase in IOP was induced unilaterally by laser photocoagulation of episcleral veins as previously described (Kalesnykas et al., 2007, Neuroscience 150: 692-704). The contralateral eye serves as control. Five-to-seven months old Long Evans rats are used. The intraocular pressure (IOP) was monitored at the baseline, on the first day after lasering (day 1), day 4, day 7 and once a week for the remaining follow-up period. Only rats with IOP of 16 mmHg or higher as assessed on day 1 are admitted to the study groups.

Administration

The test compounds are administered subcutaneously (s.c.) twice a week starting from day 1.

pERG Measurements

Recordings were performed using Celeris system (Diagnosys LLC). A single drop of drop oxybuprocaine (Oftanucain®, Santen, Finland) was applied to the cornea for local anesthesia Animals were placed on a controlled heating-pad to maintain body temperature at approximately 37° C.

Animal Sacrifice and Tissue Collection

At the end of the study, the rats were sacrificed by transcardial perfusion first with 0.9% NaCl solution, then with 4% paraformaldehyde in 0.1M phosphate buffer solution, pH 7.4. The eyeballs and optic nerves (n=4 rats from each group, collected in a randomized manner) were collected and embedded into optimal cutting temperature (OCT) for cryosectioning/retinal wholemounts (n=8 rats from each group) were prepared for further estimation of the total number of RGCs.

Morphological Assessment of Optic Nerves

After the optic nerves (from 8 rats/treatment group) were postfixed in 4% PFA (in 0.1M phosphate buffer, pH 7.4) solution, they were placed in 1% osmium, dehydrated in ascending alcohol concentration and placed in 1% uranyl acetate in 100% ethanol for 1 hour (Cone et al., 2012. Exp Eye Res. June; 99:27-35; Ragauskas et al., 2014, PLoS One. 3; 9(12)). Then the optic nerves were embedded in epoxy resin mixture at 60° C. for 48 hours and semi-thin sections (1 μm-thick) of optic nerves were serially sectioned through the optic nerve damage site. Optic nerve damage/number of axons was estimated under the light microscope.

Results:

pERG measurements (recordings) that reflect functionality of RGCs were performed at follow-up day 28. The results presented below in Table 4 and in the bar graphs shown in FIG. 1, demonstrate that treatment with the indicated combinations exhibit an increase in mean amplitude as compared to the vehicle-treated group.

TABLE 4

Lasered eye relative increase in mean amplitudes at the follow-up day 28 adjusted to baseline.

| Treatment group | Relative increase in mean amplitude on day 28, % (Compared to Vehicle) |
|---|---|
| A | 9.53% |
| B | 23.20% |
| Acidic-1 + Neutral 2 (A1N2) | 14.72% |

Figure 2:
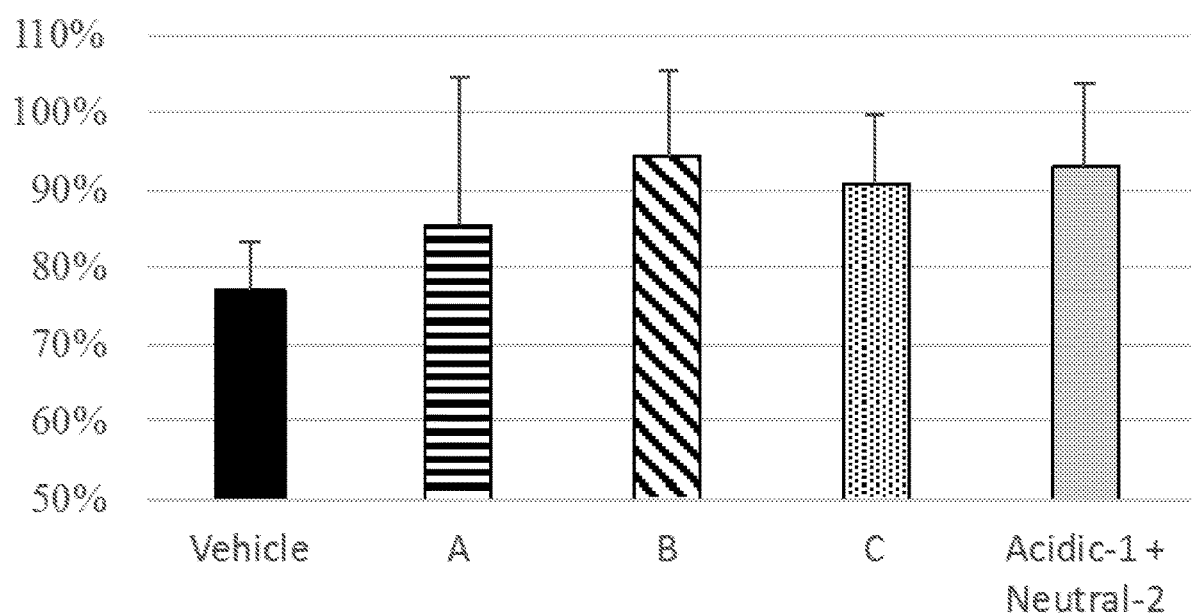
FIG. 2—Bar graphs showing number of optic nerve axons per optic nerve area in various treated rats, compared to naïve rats (%). Tested compositions include composition A-C and A1N2.

Next, optic nerve axon in samples from the tested rats were counted under the light microscope, to estimate the optic nerve damage. The results are presented in FIG. 2. As shown, administration of test combinations A, B, C and "Acidic-1+Neutral 2" (A1N2) tend to protect axons from degeneration triggered by Laser photocoagulation.

Figure 3:
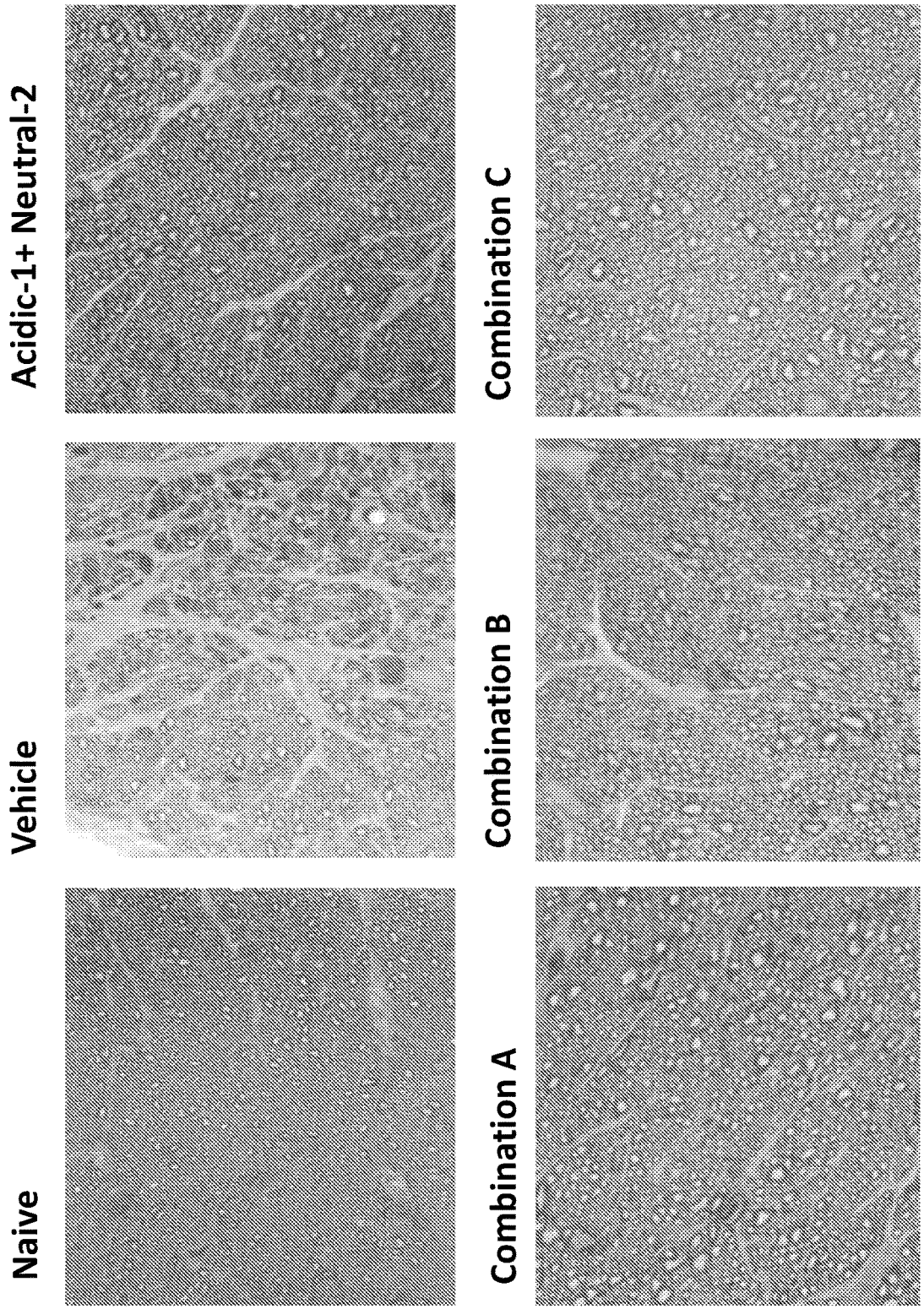
FIG. 3—Images of semi-thin cross-sections of optic nerves obtained from rats treated with the indicated combinations of compounds (Combinations A-C and A1N2), vehicle treated or non-treated rats (Naïve).

Further supporting results demonstrating the protective effect of the teste compounds can be seen in FIG. 3, which show representative images of semi thin sections of the optic nerves. The results clearly demonstrate differences in the degeneration processes between the treated groups and vehicle treated group (FIG. 3).

Conclusions: The study presented herein demonstrates the neuroprotective and neurodegenerative effect of the tested compositions in treating glaucoma.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What we claim is:

1. A method of treating an optic neuropathy condition in a subject in need thereof, the method comprising administering a composition comprising a combination of at least one triterpenoic acid and at least one neutral triterpenoid and a pharmaceutically acceptable carrier.

2. The method of claim 1, wherein said triterpenoic acid is selected from masticadienonic acid (MDA), isomasticadienonic acid (IMDA), masticadienolic acid (MLA), isomasticadienolic acid (IMLA), 3-O-acetyl masticadienolic acid, 3-O-acetyl epimasticadienolic acid, 3-O-acetyl isomasticadienolic acid (3-O-acetyl-IMLA), 3-O-acetyl epi-isomasticadienolic acid, oleanonic acid (OA) and moronic acid (MA).

3. The method of claim 2, wherein at least one of said triterpenoic acids is selected from MDA, IMDA, 3-O-acetyl-MLA and 3-O-acetyl-IMLA.

4. The method of claim 1, wherein said neutral triterpenoid is selected from (8R)-3-beta, 8-dihydroxypolypoda-13E,17E,21-triene (NF-1), (8R)-3-Oxo-8-hydroxypolypoda-13E,17E,21-triene (NF-2), Oleanonic aldehyde (NF-3), Tirucallol (NF-4), 28-hydroxylup-20(29)-en-3-one (NF-A), 28-hydroxy-beta-amyrone (NF-B), and 20-hydroxydammar-24-en-3-one (NF-P).

5. The method of claim 4, wherein at least one of said neutral triterpenoids is selected from NF-1, NF-2, NF-3 and NF-4.

6. The method of claim 1, wherein the composition comprises at least two triterpenoic acids.

7. The method of claim 1, wherein the composition comprises at least four neutral triterpenoids.

8. The method of claim 1, wherein said neutral triterpenoid comprises at least (8R)-3-beta, 8-dihydroxypolypoda-13E,17E,21-triene (NF-1).

9. The method of claim 1, wherein said neutral triterpenoid comprises at least (8R)-3-Oxo-8-hydroxypolypoda-13E,17E,21-triene (NF-2).

10. The method of claim 1, wherein neutral triterpenoid comprises at least (8R)-3-beta, 8-dihydroxypolypoda-13E, 17E,21-triene (NF-1) and (8R)-3-Oxo-8-hydroxypolypoda-13E,17E,21-triene (NF-2).

11. The method of claim 1, wherein said neutral triterpenoid comprises at least Tirucallol (NF-4).

12. The method of claim 1, wherein said neutral triterpenoid comprises at least Oleanonic aldehyde (NF-3).

13. The method of claim 1, wherein the composition is substantially devoid of essential oils.

14. The method of claim 1, wherein the at least one triterpenoic acid and the at least one neutral triterpenoid are obtained from a plant source.

15. The method of claim 1, wherein said pharmaceutically acceptable carrier comprises a hydrophobic carrier, wherein said hydrophobic carrier comprises at least one oil.

16. The method according to claim 1, wherein the optic neuropathy condition is selected from traumatic neuropathy, ischemic optic neuropathy; Radiation optic neuropathy (RON), Glaucoma, Optic neuritis, Compressive optic neuropathy, Infiltrative optic neuropathy, Mitochondrial optic neuropathy, Nutritional optic neuropathies, toxic optic neuropathies, Hereditary optic neuropathy and combinations thereof.

17. The method according to claim 16, wherein the ischemic optic neuropathy is selected from: Nonarteritic Ischemic optic neuropathy (NAION), Anterior ischemic optic neuropathy (AION) and Posterior ischemic optic neuropathy.

18. The method according to claim 1, wherein the optic neuropathy condition results from a storage disease.

19. The method according to claim 18, wherein the storage disease causes the deposition of lipoprotenaceous substances in the optical nerve.

20. The method according to claim 1, wherein the composition is administered by parenteral route selected from the group consisting of intravenous, intramuscular, subcutaneous, intradermal, intraperitoneal, intraarterial, intrauterine, intraurethral, intracardial, intracerebral, intracerebroventricular, intrarenal, intrahepatic, intratendon, intraosseous, intraocular and intrathecal.

* * * * *

UNITED STATES PATENT AND TRADEMARK OFFICE
CERTIFICATE OF CORRECTION

PATENT NO.         : 11,207,333 B2                        Page 1 of 9
APPLICATION NO.    : 16/330486
DATED              : December 28, 2021
INVENTOR(S)        : Zadik Hazan et al.

It is certified that error appears in the above-identified patent and that said Letters Patent is hereby corrected as shown below:

In the Specification

In Column 12, Line 37, replace " 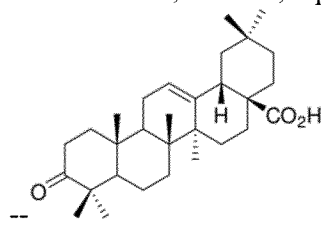 Oleanonic acid (OLN or OA)" with

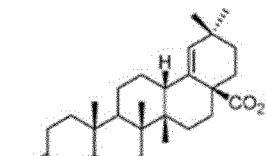 Oleanonic acid (OLN or OA)--;

In Column 12, Line 55, replace " 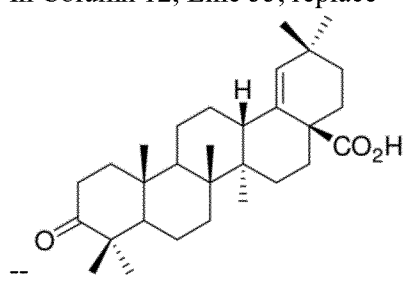 Moronic acid (MA)" with

-- 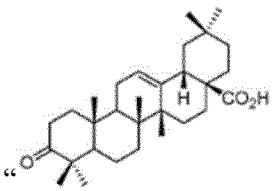 Moronic acid (MA)--;

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*

In Column 15, Line 50, replace " 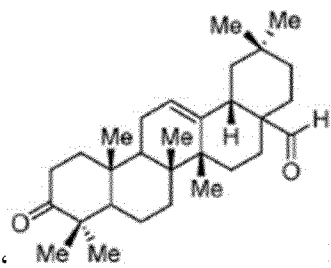 NF-3" with
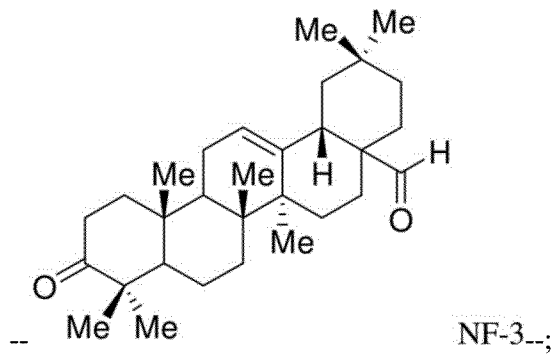 NF-3 --;
In Column 16, Line 50, replace " 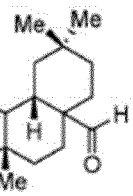 NF-B" with
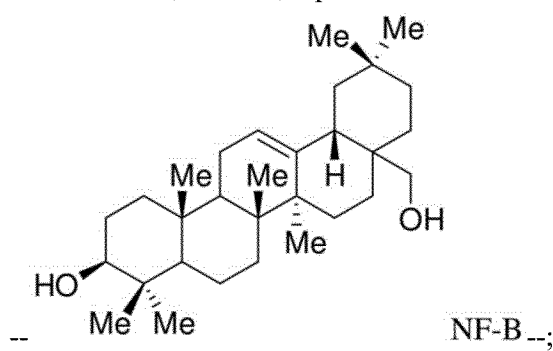 NF-B --;
In Column 18, Line 37 to Column 19, Line 48, replace "Name: Beta-amyrin
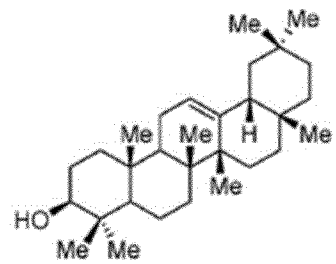
Beta-amyrin
Name: Beta-amyrone

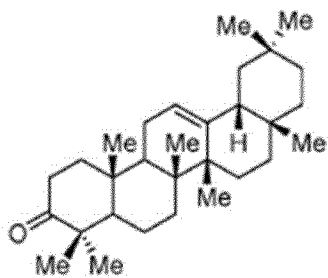
Beta-amyrone
Name: Germanicol
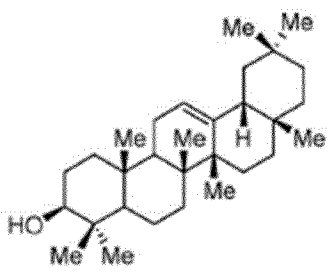
Germanicol
Name: 28-nor-beta-amyrin
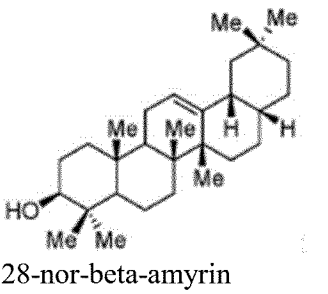
28-nor-beta-amyrin
Name: 28-nor-beta-amyrone
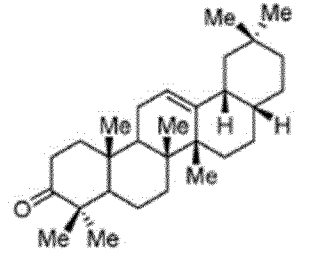
28-nor-beta-amyrone" with
--Name: Beta-amyrin

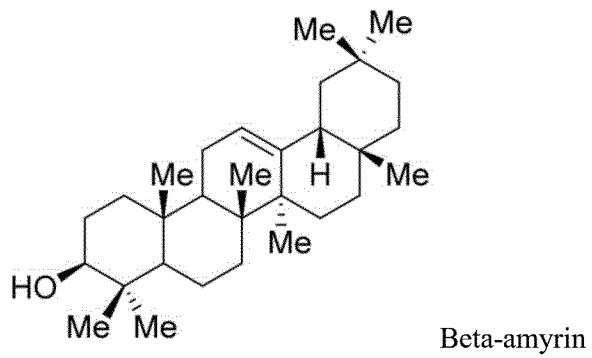
Beta-amyrin
Name: Beta-amyrone
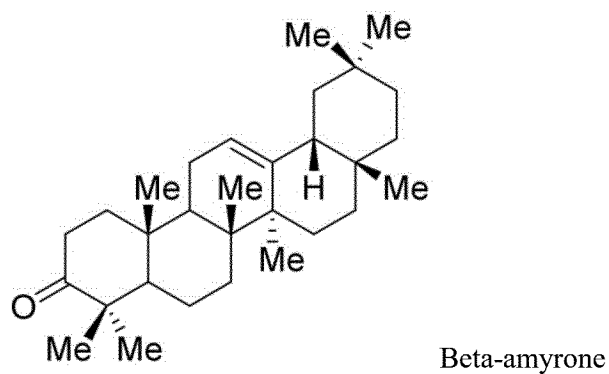
Beta-amyrone
Name: Germanicol
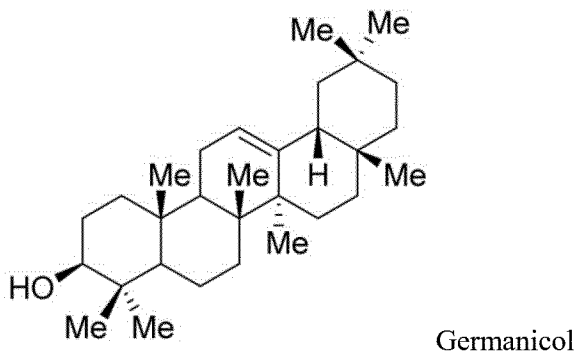
Germanicol
Name: 28-nor-beta-amyrin

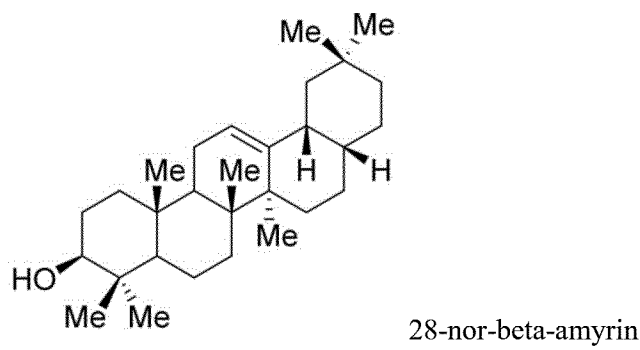
28-nor-beta-amyrin
Name: 28-nor-beta-amyrone
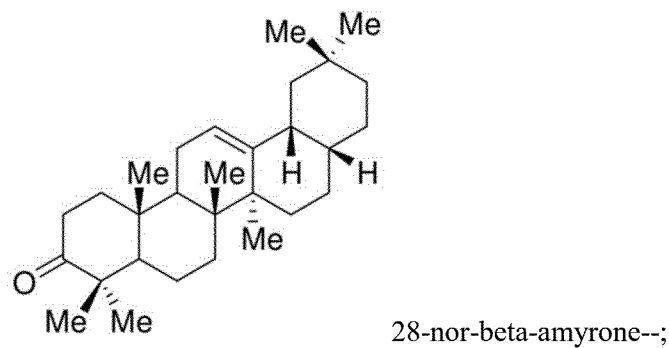
28-nor-beta-amyrone--;
In Column 63, Line 55 to Column 64, Line 38, replace
"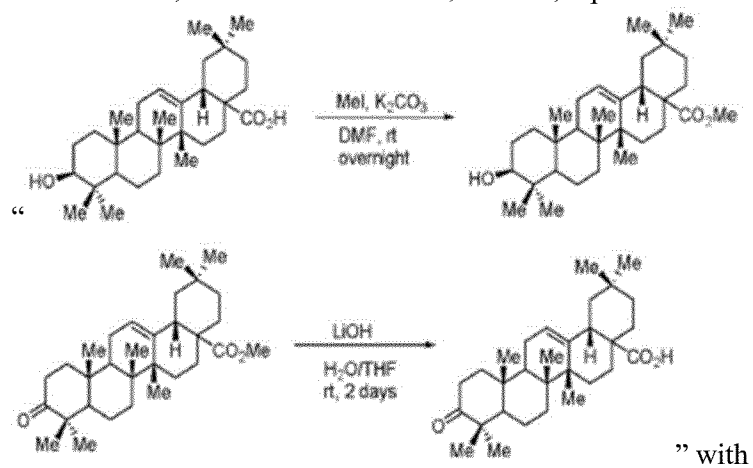" with

CERTIFICATE OF CORRECTION (continued)
U.S. Pat. No. 11,207,333 B2

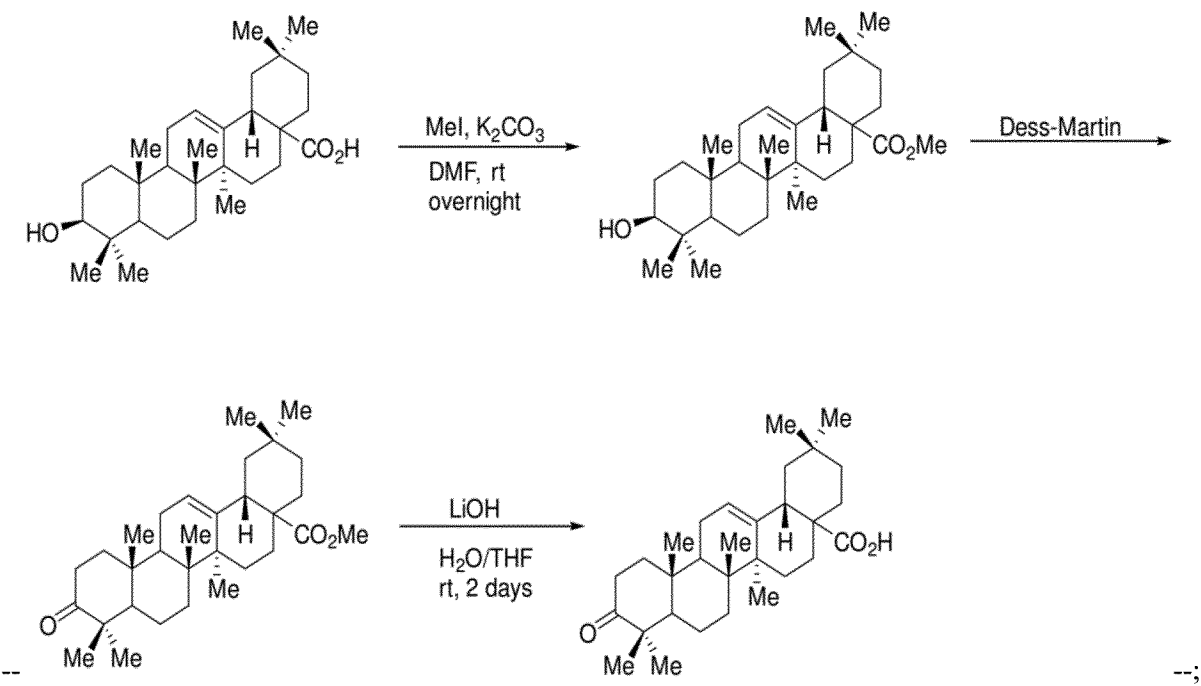

--;

In Column 65, Line 41 to Column 66, Line 22, replace "

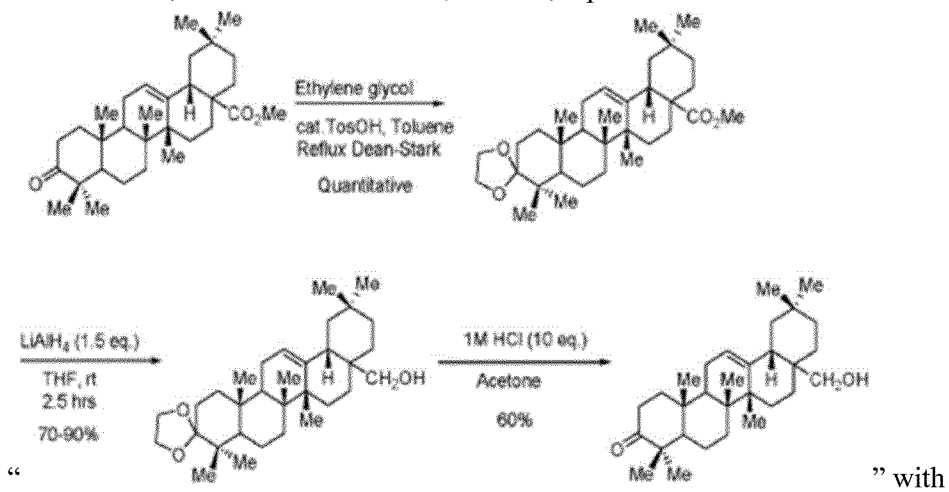

" with

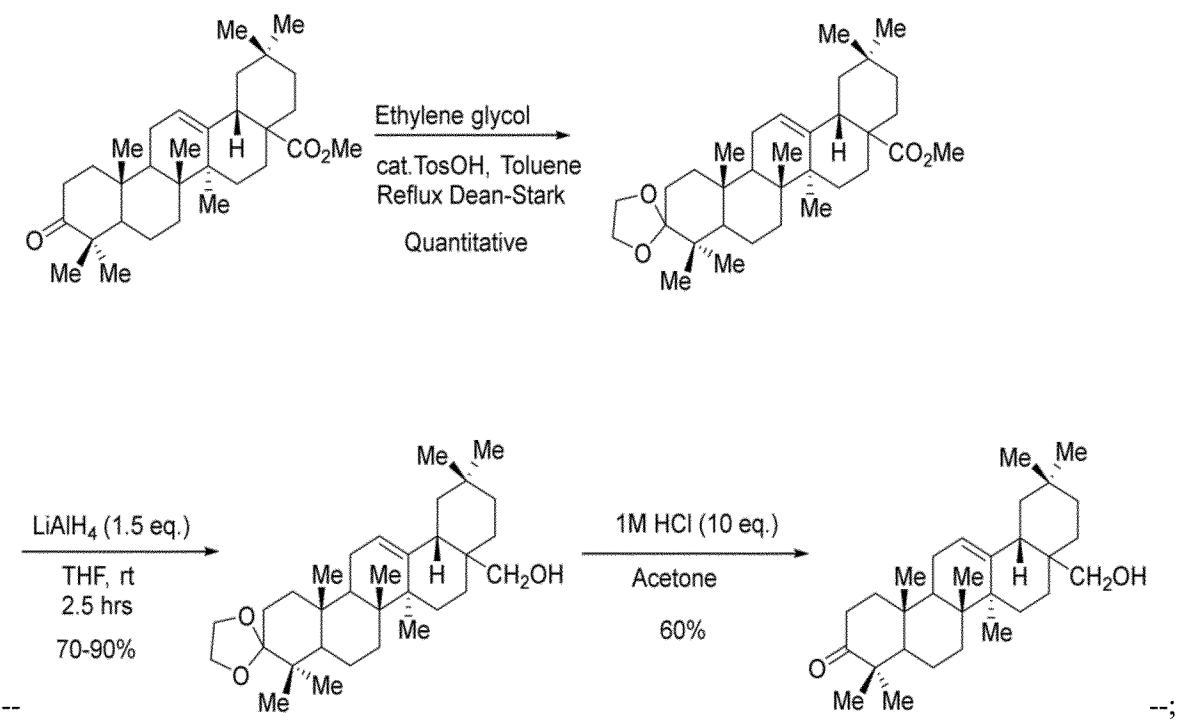
In Column 66, Line 45 to Column 67, Line 12, replace
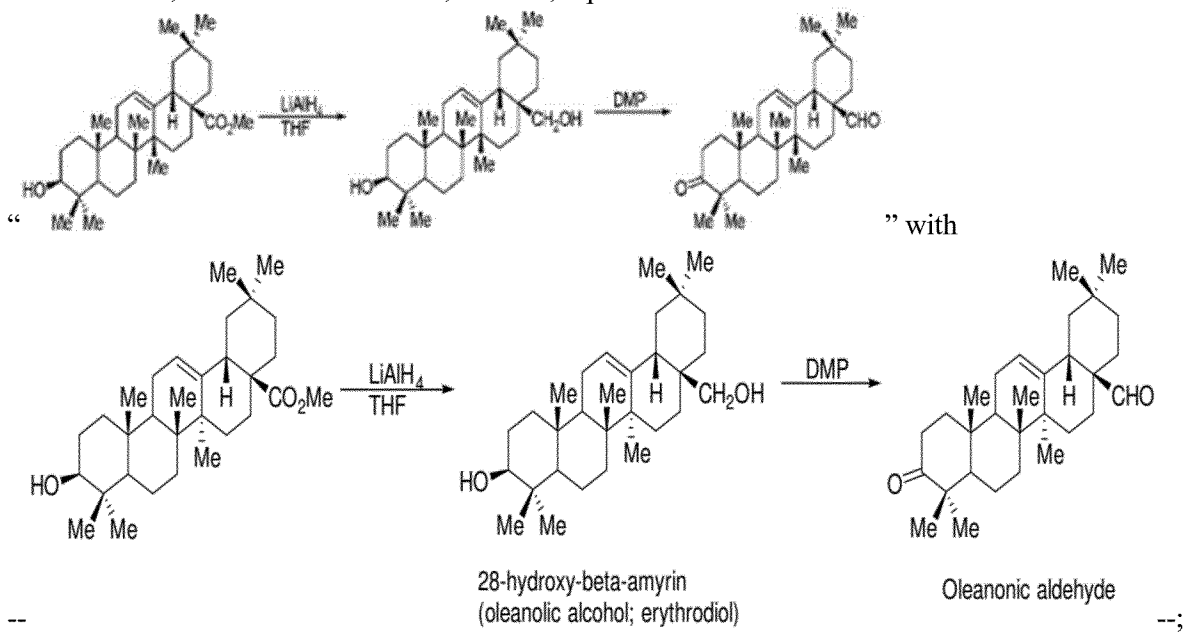

CERTIFICATE OF CORRECTION (continued)
U.S. Pat. No. 11,207,333 B2

In Column 71, Line 42 to Column 72, Line 64, replace

"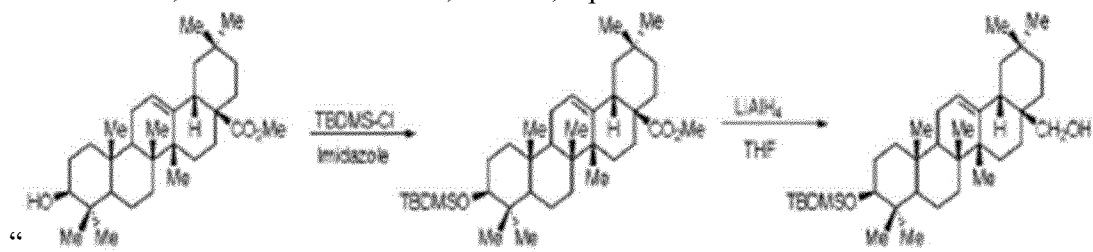

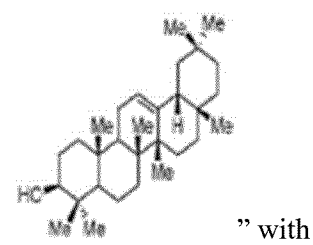" with

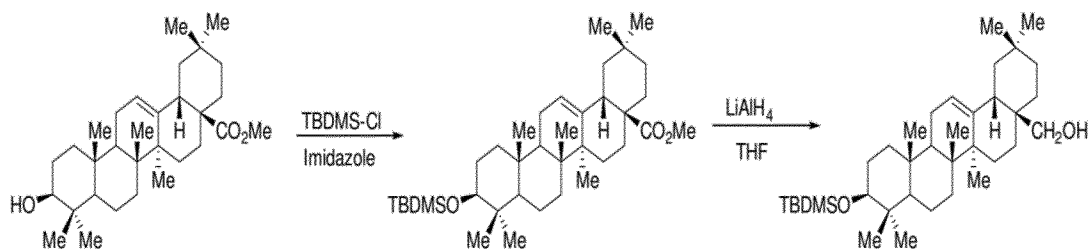

--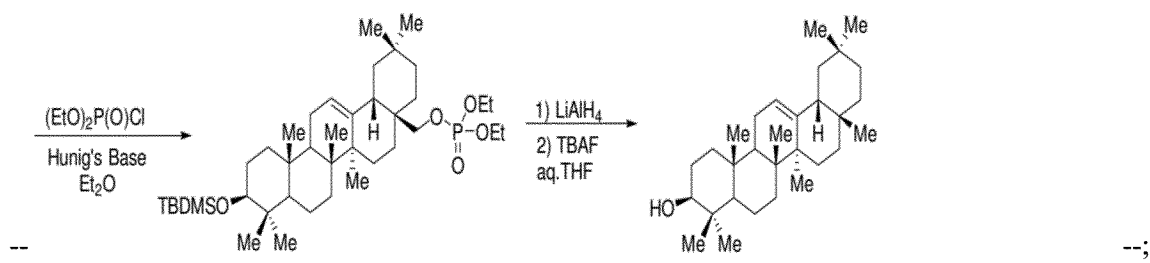--;

In Column 73, Line 19 to Column 73, Line 43, replace

"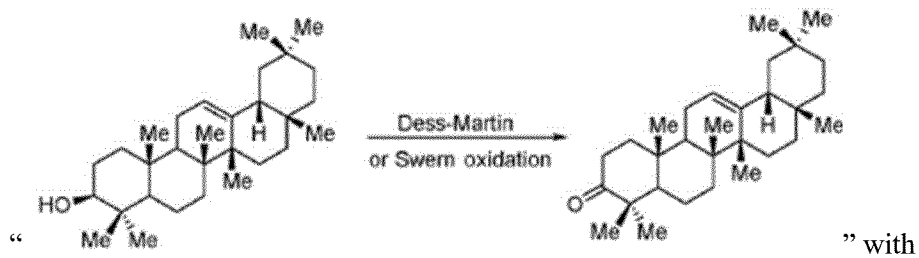" with

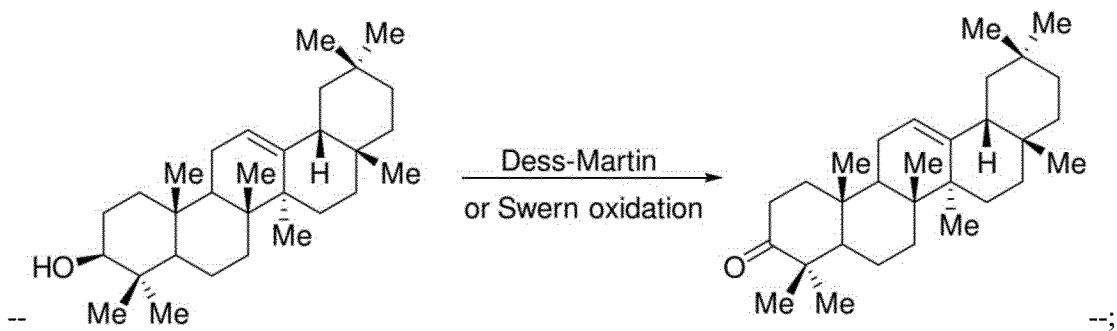
--;
In Column 74, Line 26 to Column 74, Line 63, replace
" 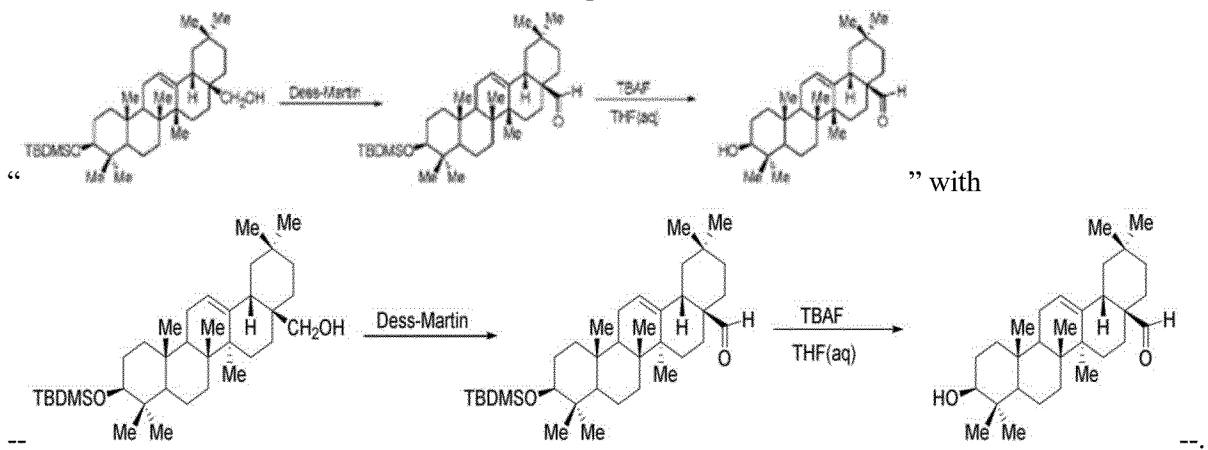 " with
--.